(12) United States Patent
Schneider et al.

(10) Patent No.: US 12,065,392 B2
(45) Date of Patent: Aug. 20, 2024

(54) ROOT EXUDATE-ACTIVATED SYSTEM FOR AGROCHEMICAL DELIVERY

(71) Applicants: Carleton University, Ottawa (CA); Her Majesty the Queen in Right of Canada, as represented by The Minister of Agriculture and Agri-Food, Ottawa (CA); The Governors of the University of Alberta, Edmonton (CA); Juan Schneider, Laval (CA)

(72) Inventors: Juan Schneider, Laval (CA); Carlos Monreal, Ottawa (CA); Maria Derosa, Ottawa (CA); Phillip Choi, Edmonton (CA); Emily Mastronardi, Ottawa (CA); Phepafatso Tsae, Ottawa (CA); Francisco Matus, Temuco (CL)

(73) Assignees: Carleton University, Ontario (CA); Her Majesty the Queen in Right of Canada, as represented by The Minister of Agriculture and Agri-Food, Ontario (CA); The Governors of the University of Alberta, Alberta (CA)

( * ) Notice: Subject to any disclaimer, the term of this patent is extended or adjusted under 35 U.S.C. 154(b) by 677 days.

(21) Appl. No.: 17/276,302

(22) PCT Filed: Sep. 16, 2019

(86) PCT No.: PCT/CA2019/051306
§ 371 (c)(1),
(2) Date: Mar. 15, 2021

(87) PCT Pub. No.: WO2020/051717
PCT Pub. Date: Mar. 19, 2020

(65) Prior Publication Data
US 2022/0033322 A1 Feb. 3, 2022

Related U.S. Application Data

(60) Provisional application No. 62/731,454, filed on Sep. 14, 2018.

(51) Int. Cl.
C05G 5/30 (2020.01)
A01G 29/00 (2006.01)
(Continued)

(52) U.S. Cl.
CPC ............... *C05G 5/37* (2020.02); *A01G 29/00* (2013.01); *C05C 9/005* (2013.01); *C12N 15/115* (2013.01); *A01G 22/00* (2018.02); *C12N 2310/16* (2013.01)

(58) Field of Classification Search
None
See application file for complete search history.

(56) References Cited

FOREIGN PATENT DOCUMENTS

| | | | | |
|---|---|---|---|---|
| CN | 105821046 A | * | 8/2016 | ........... C07C 227/40 |
| WO | 2019060903 A1 | | 3/2019 | |

OTHER PUBLICATIONS

Badri, D. V., et al., "Regulation and Function of Root Exudates." Plant, Cell and Environment, 2009, 32: 666-681.
(Continued)

*Primary Examiner* — Wayne A Langel
(74) *Attorney, Agent, or Firm* — SALIWANCHIK, LLOYD & EISENSCHENK

(57) ABSTRACT

A system for delivering fertilizer to the roots of a plant includes coated fertilizer particles. The coating can include a cellulose derivative, optionally a fatty acid, and a component, such as an aptamer, which binds specifically to a
(Continued)

material, such as serine, which is released by the roots of the plant when the plant is actively taking up nutrients from the soil. The permeability of the coating increases when the coated particles are exposed to the material released by the roots of the plant. Thus, nutrient release from the coated fertilizer particles is synchronized with uptake of the nutrients by the plant during active growth. Advantages of the system may include one or more of improved nitrogen use efficiency by the plant, improved crop productivity, and/or reduced leaching of fertilizer from the soil.

14 Claims, 14 Drawing Sheets

Specification includes a Sequence Listing.

(51) Int. Cl.
      C05C 9/00      (2006.01)
      C09D 101/08      (2006.01)
      C12N 15/115      (2010.01)
      A01G 22/00      (2018.01)

(56) References Cited

OTHER PUBLICATIONS

Bayati, F., et al., "Diffusion Behavior of Water at Infinite Dilution in Hydroxypropyl Xylan Films with Sorbitol and Cellulose Nanocrystals." ACS Sustainable Chemistry & Engineering, 2014, 2: 1305-1311.
Bayati, F., et al., "Inverse Gas Chromatography Study of the Permeability of Aroma through Hydroxypropyl Xylan Films." ACS Sustainable Chemistry & Engineering, 2015, 3: 3114-3122.
Bayati, F., et al., "Effect of Humidity on the Permeability of Alcohols in Hydroxypropyl Xylan Films." ACS Sustainable Chemistry & Engineering, 2016, 4: 2578-2583.
Bremner, J. M., "Determination of Nitrogen in Soil by the Kjeldahl Method." Journal of Agricultural Science, 1960, 55 (1): 11-33.
Bremner, J. M., "Nitrogen-Urea." Methods of Soil Analysis: Part 2, Chemical and Microbiological Properties—Agronomy Monograph No. 9 (2nd Edition), 1982, 699-709.
Campos, E. V. R., "Polysaccharides as Safer Release Systems for Agrochemicals." Agronomy for Sustainable Development, 2015, 35: 47-66.
Caruthers, M. H., et al., "Chemical Synthesis of Deoxyoligonucleotides by the Phosphoramidite Method." Methods in Enxymology, 1987, 154: 287-313.
Foster, A., et al., "Development of a Biocompatible Layer-by-Layer Film System Using Aptamer Technology for Smart Material Applications." Polymers, 2014, 6: 1631-1654.
Hoinka, J., et al., "AptaCluster—A Method to Cluster HT-SELEX Aptamer Pools and Lessons from its Application." Research in Computational Molecular Biology, 2014, 8394: 115-128.
Hoinka, J., et al., "Large Scale Analysis of the Mutational Landscape in HT-SELEX Improves Aptamer Discovery." Nucleic Acids Research, 2015, 43(12): 5699-5707.
Mastronardi, E., "Development of Aptamers and Aptamer-Based Materials for Agricultural Applications." Thesis, Carlton University, Ottawa, Ontario, 2017, 1-219.
Mastronardi, E., "139 Development and Application of Crop Exudate Specific Aptamers." Journal of Biomolecular Structure and Dynamics, 2013, 31: Sup1, doi: 10.1080/07391102.2013.786381.
Matus, F., et al., "Producing Isotopically Enriched Plant, Soil Solution, and Rhizosphere Soil Materials over a Few Hours." Communications in Soil Science and Plant Analysis, 2014, 45: 865-880.
McKeague, M., et al., "Development of a DNA Aptamer for Direct and Selective Homocysteine Detection in Human Serum." The Royal Society of Chemistry, 2013, 3: 24415-24422.
McRae, G., et al., "LC-MS/MS Quantitative Analysis of Reducing Carbohydrates in Soil Solutions Extracted from Crop Rhizospheres." Analytical and Bioanalytical Chemistry, 2011, 400: 2205-2215.
Mulvaney, R. L., et al., "A Modified Diacetyl Monoxime Method for Colorimetric Determination of Urea in Soil Extracts." Communications in Soil Science and Plant Analysis, 1979, 10(8): 1163-1170.
Reuter, J. S., et al., "RNAstructure: Software for RNA Secondary Structure Prediction and Analysis." BMC Bioinformatics, 2010, 11(129): 1-9.
Shipley, R., et al., "Compartment Analysis: A Single Pool, Real or by Lumping." Tracer methods for in vivo kinetics. Theory and applications. Academic Press, New York, New York, 10003, USA, 1972, 1-20.
Stoltenburg, R., et al., "FluMag-SELEX as an Advantageous Method for DNA Aptamer Selection." Analytical and Bioanalytical Chemistry, 2005, 383: 83-91.
Sultan, Y., et al., "Preparation of Functional Aptamer Films Using Layer-by-Layer Self-Assembly." Biomacromolecules, 2009, 10: 1149-1154.
Sultan, Y., et al., "Target Binding Influences Permeability in Aptamer-Polyelectrolyte Microcapsules." Small, 2011, 7 (9): 1219-1226.
Dell'Mour, M., "Development of novel methods for the analysis of root exudates." Thesis, University of Natural Resources and Life Sciences, Vienna, Nov. 2010, pp. 1-60.
Tawaraya, K., et al., "Metabolite profiling of soybean root exudates under phosphorus deficiency." Soil Science and Plant Nutrition, 2014, pp. 1-16, http://dx.doi.org/10.1080/00380768.2014.945390.
Zhang, X., "Aptamer Based Targeted Delivery System: Developing Aptamer Encapsulated Polyelectrolyte Microcapsules by the Layer-by-Layer Technique." Thesis, Carlton University, Ottawa, Ontario, Canada, 2011, pp. 1-129.

\* cited by examiner

ROOT EXUDATE-ACTIVATED SYSTEM FOR AGROCHEMICAL DELIVERY

CROSS REFERENCE TO RELATED APPLICATIONS

This application is a National Stage Application of International Application Number PCT/CA2019/051306, filed Sep. 16, 2019; which claims priority to U.S. Patent Application No. 62/731,454, filed Sep. 14, 2018.

The Sequence Listing for this application is labeled "pctca2019051306-seq1.txt", which was created on Sep. 14, 2018, and is 11 KB. The entire content is incorporated herein by reference in its entirety.

BACKGROUND

The present application is directed to systems for delivering agrochemicals to plants. More specifically, the present application is directed to systems for delivering agrochemicals such as fertilizer to the roots of plants when activated by the presence of a root exudate.

Agricultural cultivation of crops often involves the use of fertilizers and other agrochemicals. For example, fertilizers are commonly used to supply plants with additional nutrients beyond those available from natural sources, thereby improving crop yields. However, the efficiency with which agronomic crops use fertilizer nutrients is often low. For example, the efficiency of macronutrient use from fertilizer can be only 30-50% for nitrogen, and less than 15% for phosphorus, while the efficiency of use of micronutrients such as zinc can be less than 3%. Inefficient fertilizer use results in increased costs for farmers and can have deleterious effects on the environment. For example, unused nutrients in the applied fertilizer can be leached from the soil and pollute water sources, leading to eutrophication. In addition, unused nutrients can be converted by soil microorganisms into gaseous products such as nitrogen oxides which act as greenhouse gases, potentially contributing to global warming.

Enhanced efficiency fertilizers can release nutrients in a controlled way to reduce waste of nutrients. For example, slow release fertilizers can release nutrients in response to biochemical modification of nutrient precursors at rates at which the released nutrient can be taken up more efficiently by a plant, decreasing the amount of the nutrient which is lost to the environment. In addition, a controlled release fertilizer such as ESN™ Smart Nitrogen (Nutrien Ltd.), can release nutrients at rates which vary with environmental conditions such as soil temperature. However, it is desirable to develop alternative systems which could improve the efficiency with which nutrients from fertilizers and other agrochemicals are delivered to, and can be used by, plants. Advantageously, such systems might also improve crop productivity.

SUMMARY

In one aspect, the present application provides a delivery system for delivering an agrochemical to a root of a plant. The system includes particles which can release the agrochemical. In at least one embodiment, the particles are particles of a fertilizer which can release one or more nutrients to the root of the plant. In at least one embodiment, the nutrients include nitrogen. In at least one embodiment, the fertilizer is urea.

The particles are coated with a coating, such that when the coated particles are exposed to a root exudate, the permeability of the coating increases and the rate at which the agrochemical is released from the coated particles increases. In at least one embodiment, an increase in the rate of release of the root exudate from the plant corresponds temporally to an increase in the demand of the plant for one or more nutrients.

In at least one embodiment, the coating comprises a cellulose derivative. In at least one such embodiment, the coating further comprises a fatty acid. In at least one embodiment, the cellulose derivative is ethyl cellulose. In at least one embodiment, the fatty acid is palmitic acid. In at least one embodiment, the coating includes an aptamer which binds specifically to the root exudate. In at least one embodiment, the plant is canola and the root exudate comprises L-serine. In at least one embodiment, the aptamer has a sequence selected from SEQ ID NO:20, SEQ ID NO:21, SEQ ID NO:22, SEQ ID NO:23, SEQ ID NO:24, SEQ ID NO:25, SEQ ID NO:30, SEQ ID NO:31, SEQ ID NO:32, SEQ ID NO:33 and SEQ ID NO:34.

A further aspect of the application provides a method of preparing a delivery system as described herein, including coating particles of the fertilizer with the coating.

Still another aspect of the present application provides an aptamer configured to bind specifically to a root exudate. In at least one embodiment, the root exudate comprises L-serine. In at least one embodiment, the aptamer has a sequence selected from SEQ ID NO:20, SEQ ID NO:21, SEQ ID NO:22, SEQ ID NO:23, SEQ ID NO:24, SEQ ID NO:25, SEQ ID NO:30, SEQ ID NO:31, SEQ ID NO:32, SEQ ID NO:33 and SEQ ID NO:34.

In another aspect, the present application provides a coating for particles of a fertilizer, the coating comprising a cellulose derivative and an aptamer configured to bind specifically to a root exudate. In at least one embodiment, the coating further comprises a fatty acid.

BRIEF DESCRIPTION OF THE DRAWINGS

Further features of the present invention will become apparent from the following written description and the accompanying figures, in which.

Figure 11:
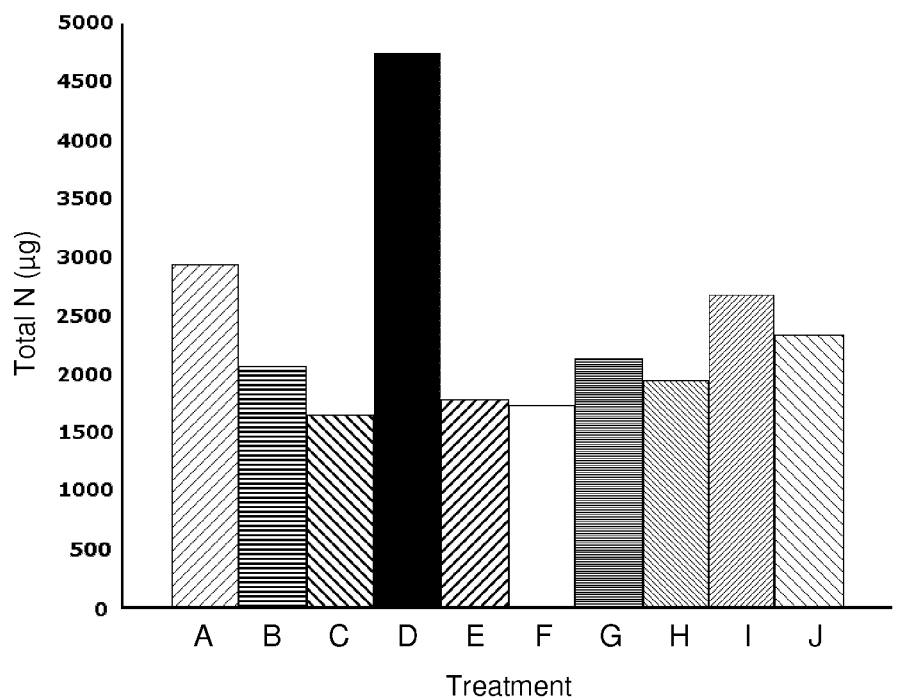
FIG. 11 is a bar graph showing the amount of total nitrogen leached from soil unplanted or planted with canola plants, and receiving one of the following treatments.
Figure 12:
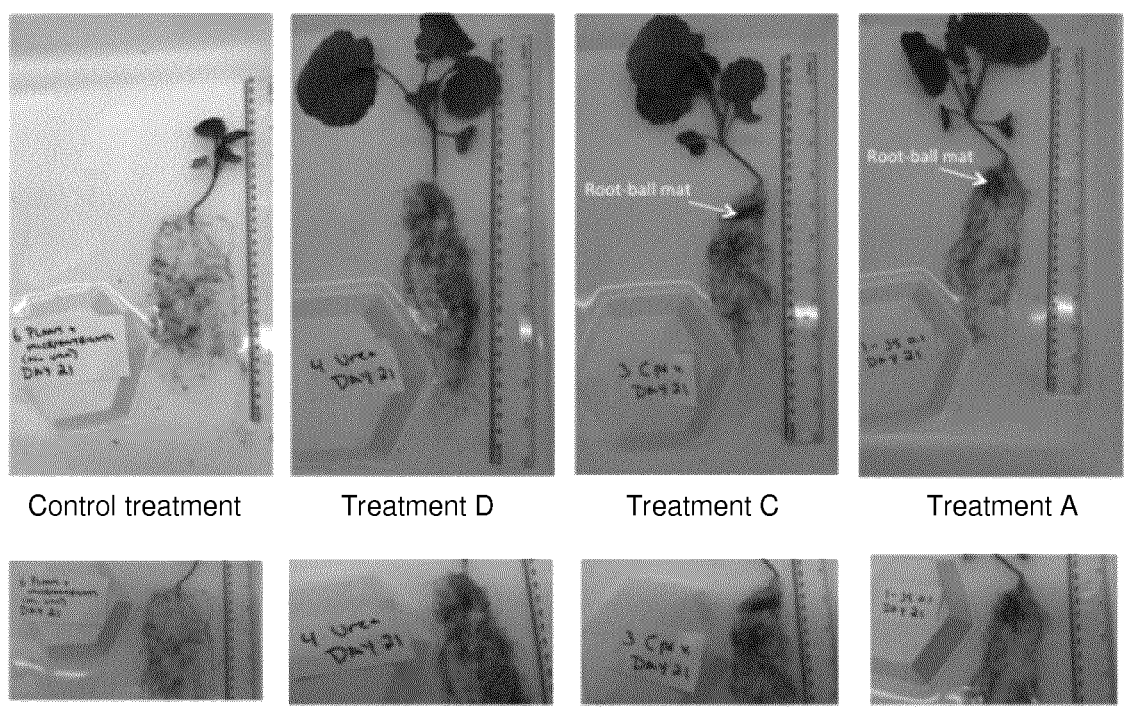
Figure 13:
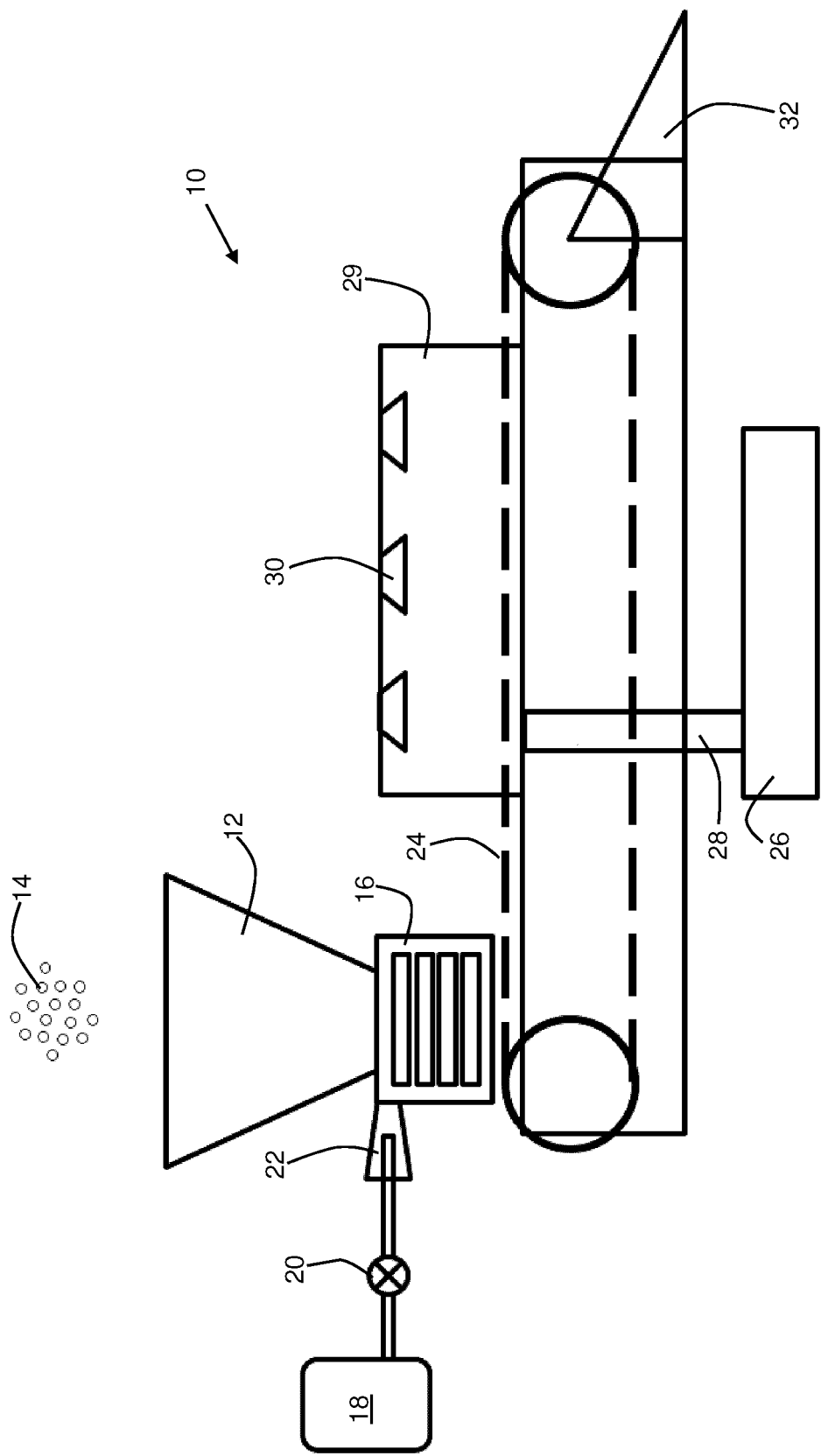
Figure 14:
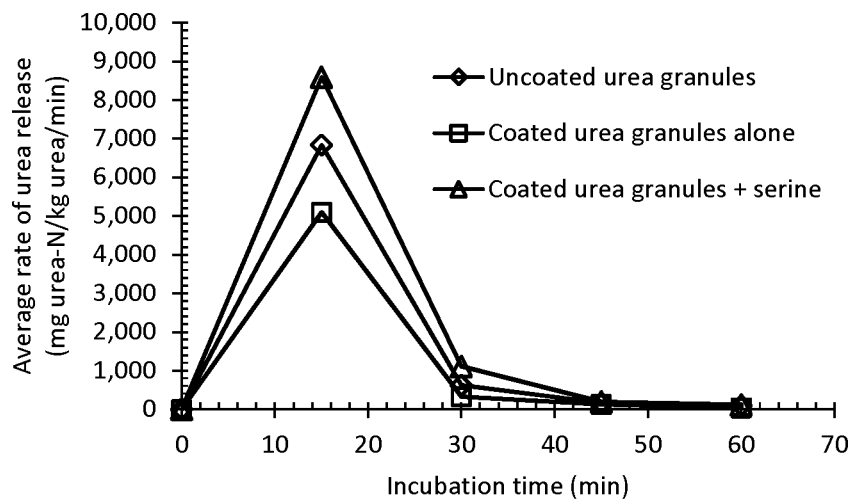
Figure 15:
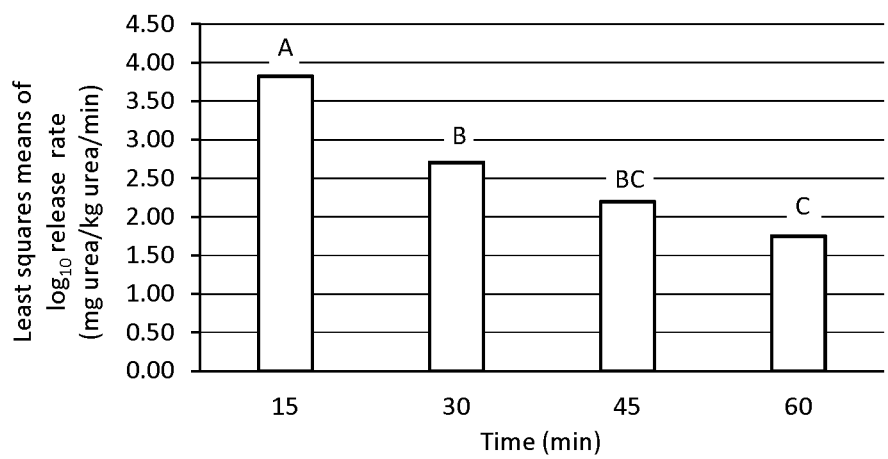
Figure 16:
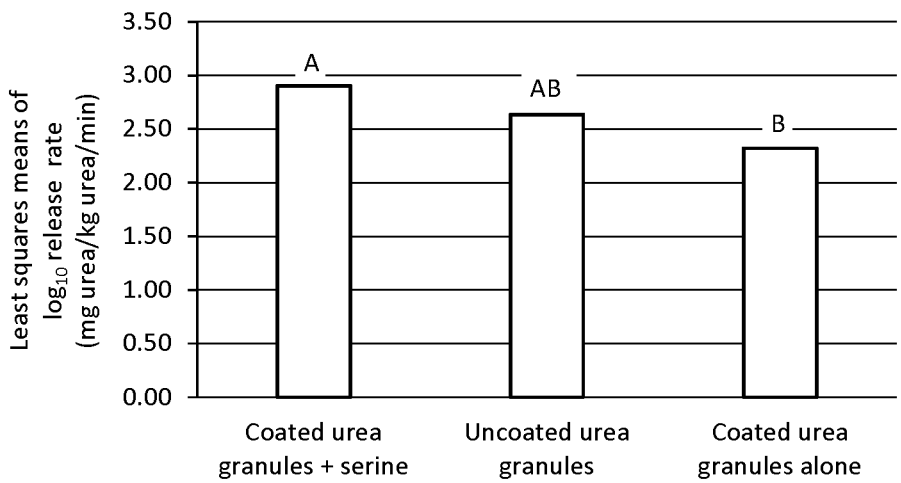

A Urea fertilizer coated with an embodiment of the present coating containing ethyl cellulose: palmitic acid (1:0.1 by weight);
B Urea fertilizer coated with an embodiment of the present coating containing ethyl cellulose: palmitic acid (1:0.5 by weight);
C Urea fertilizer coated with palmitic acid;
D Uncoated urea fertilizer;
E ESN™ Smart Nitrogen fertilizer;
F No fertilizer (soil planted with canola);
G Urea fertilizer coated with an embodiment of the present coating containing ethyl cellulose: palmitic acid (1:0.1 by weight) and a short random strand of DNA;
H Urea fertilizer coated with an embodiment of the present coating containing ethyl cellulose: palmitic acid (1:0.5 by weight) and a short random strand of DNA;
I Urea fertilizer coated with palmitic acid and a short random strand of DNA; and
J No fertilizer (soil alone, not planted);

FIG. 12 is a photograph showing the presence or absence of root-ball mat formation in canola plants treated with treatments A, C or D of FIG. 11, or a control treatment;

FIG. 13 is a diagrammatic representation of a coating system useful in preparing at least one embodiment of coated particles according to the invention;

FIG. 14 is a graph showing the relationship between incubation time in sand and average rate of urea nitrogen release from uncoated granules and an embodiment of coated granules according to the present invention in the presence and absence of L-serine;

FIG. 15 is a bar graph showing the relationship between the least squares means of logo-transformed urea nitrogen release rate from the granules of FIG. 14 and incubation time. Statistically significant differences between data as determined by Tukey's test are indicated by different letters (A, B, C); and FIG. 16 is a bar graph showing the relationship between the least squares means of logo-transformed urea nitrogen release rate from the granules of FIG. 14 and the presence or absence of granule coating and L-serine. Statistically significant differences between data as determined by Tukey's test are indicated by different letters (A, B).

BRIEF DESCRIPTION OF SEQUENCES

SEQ ID NOs: 1-40 are sequences useful according to the subject invention.

DETAILED DESCRIPTION

The present application provides a delivery system for delivering one or more agrochemicals to a root of a plant. In at least one embodiment, the agrochemicals include one or more fertilizers which can release one or more nutrients to the root of the plant. In at least one embodiment, the one or more nutrients include but are not limited to nitrogen, phosphorus, potassium, sulfur and micronutrients, including but not limited to iron, zinc, molybdenum, copper and other micronutrients well known in the art. In at least one embodiment, the one or more nutrients include nitrogen. In at least one such embodiment, the fertilizer is urea. In at least one embodiment, the agrochemicals, including but not limited to fertilizers, are particulate in form, including but not limited to in the form of pellets, granules, or any other granular form known to the skilled person.

The particles of the agrochemicals are coated with a coating. In at least one embodiment, the thickness of the coating on the particles is in a range from about 50 nm to about 5 µm. In at least one embodiment, the coating comprises a hydrophobic polymer. In at least one embodiment, the permeability of water through the hydrophobic polymer ranges from about $10^{-9}$ to about $10^{-10=3}$ [STP]/cm·atm·s. In at least one embodiment, the hydrophobic polymer is a cellulose derivative. In at least one embodiment, the hydrophobic polymer is ethyl cellulose.

In at least one embodiment, the coating comprises a cellulose derivative and a fatty acid. In at least one embodiment, the cellulose derivative is ethyl cellulose. In at least one embodiment, the fatty acid is palmitic acid. In at least one embodiment, the ratio by weight of palmitic acid to ethyl cellulose ranges from about 1:10 to about 5:10.

In at least one embodiment, the coating further includes an aptamer which binds specifically to a root exudate. As used herein, the term "root exudate" is intended to refer to material exuded from the roots of plants into the surrounding soil or other medium. Root exudates include but are not limited to water, ions, oxygen, primary and secondary metabolites including but not limited to sugars, amino acids, polysaccharides and proteins, secondary metabolites, hormones, vitamins, other root exudates well known in the art and mixtures thereof. Root exudates can have a variety of functions, including but not limited to attracting, repelling or signalling microorganisms and other organisms, including but not limited to neighbouring plants; providing a defense against pathogenic, predatory or competing organisms and microorganisms; and changing the properties of the soil, including but not limited to the resilience of the soil, or the ability of the soil to resist a disturbance or recover its fertility or other properties following a disturbance. The identity and concentration of compounds in root exudates may be affected by many factors, including but not limited to internal factors, including but not limited to genetic factors, biochemical factors and the identity, condition and stage of growth of the plant producing the root exudate, and environmental factors, including but not limited to the proximity of other organisms or microorganisms, levels of water and nutrients, pH, and temperature, light and other soil conditions.

In at least one embodiment, the root exudate is released when the plant is actively taking up nutrients from the soil and demand by the plant for the nutrients is increased. In at least one embodiment, when the plant is canola, the root exudate comprises L-serine. In such embodiments, the aptamer binds selectively to L-serine. In at least one such embodiment, the aptamer binds to L-serine at concentrations in the range of about 50 ng/mL to about 300 ng/mL, or in the range of about 100 ng/mL to about 300 ng/mL, or in the range of about 150 ng/mL to about 300 ng/mL, or in the range of about 200 ng/mL to about 300 ng/mL. In at least one such embodiment, the aptamer binds to L-serine at concentrations in the range of about 0.5 µmol/L to about 3 µmol/L, or in the range of about 1 µmol/L to about 3 µmol/L, or in the range of about 1.5 µmol/L to about 3 µmol/L, or in the range of about 2 µmol/L to about 3 µmol/L. It has been found that L-serine is present in the soil solution of the rhizosphere near the root of a canola plant at such concentrations when the canola plant is producing the root exudate.

Suitable aptamers can be prepared and identified using methods well known in the art, including but not limited to the SELEX (Systematic Evolution of Ligands by EXponential enrichment) method. As is known in the art, the SELEX method involves exposing a library of polynucleotide sequences to a target ligand immobilized on a solid support. Sequences which bind to the target under the conditions of the exposure are retained on the solid support, while sequences which do not bind under these conditions are washed away. The sequences which bind to the solid support can be eluted by contacting the solid support with the target ligand, and amplified by polymerase chain reaction (PCR) methods. Additional rounds of selection, including exposing the eluted sequences to the solid support bearing the immobilized ligand under increasingly stringent binding conditions, washing away unbound sequences and eluting bound sequences, can provide sequences which bind to the target ligand with the desired binding affinity. In light of the teaching herein, the person skilled in the art would be aware of methods which can be used to identify suitable aptamers.

In at least one embodiment, the aptamer is a DNA aptamer. In at least one embodiment, the DNA aptamer comprises D-deoxyribonucleotide residues. In at least one embodiment, the DNA aptamer comprises one or more L-deoxyribonucleotide residues. In at least one embodiment, the DNA aptamer is a spiegelmer comprising L-deoxyribonucleotide residues. In at least one embodiment, the aptamer is an RNA aptamer. In at least one embodiment, the RNA aptamer comprises D-ribonucleotide residues. In at least one embodiment, the RNA aptamer comprises one or more L-deoxyribonucleotide residues. In at least one embodiment, the RNA aptamer is a spiegelmer comprising L-ribonucleotide residues. In at least one embodiment, the aptamer is a peptide nucleic acid.

In at least one embodiment, suitable aptamers have a sequence which comprises one or more common structural motifs, each selected from CCTATGCGTGCTACCGTGAA (SEQ ID NO:2), AGATAGTAAGTGCAATCT (SEQ ID NO:26), GGAAGAGCACACGTCTGAACTCCAGT-CACTTAGGCATC (SEQ ID NO:27), GGAAGAGCACACG (SEQ ID NO:28), CGATCTG, CGATC, -GATC- -, -TGGATAT, -TGGA- - -, GGAGA, TGAA, GAAG, TGAT, ACGT, CTGA, CATC, AGTG- -, AGCACA, GTGC, TACC, ATCT, GATA, TATT, CGTG, GTGA, and ACCG.

In at least one embodiment, the one or more common structural motifs are each selected from GATC, AGATAGTAAGTGCAATCT (SEQ ID NO:26) and GGAAGAGCACACG (SEQ ID NO:28).

In at least one embodiment, suitable aptamers include but are not limited to the aptamers in Table 1 below.

TABLE 1

| Aptamer | Sequence | Identifier |
|---|---|---|
| A-1 | AGCAGCACAGAGGTCAGATGCCTATGCGTGCTACCG TGAAACCGATCGGAAGAGCACACGCCTATGCGTGCT ACCGTGAA | SEQ ID NO: 20 |
| A-2 | AGCAGCACAGAGGTCAGATGCGATCTGGATATTATTT TTGATACCCCTTTGGGGAGACATCCTATGCGTGCTAC CGTGAA | SEQ ID NO: 21 |

TABLE 1-continued

| Aptamer | Sequence | Identifier |
|---|---|---|
| B-1 | ATACCAGCTTATTCAATTAGATAGTAAGTGCAATCTAG<br>ATCGGAAGAGCACACGTCTGAACTCCAGTCACTTAG<br>GCATCAGATAGTAAGTGCAATCT | SEQ ID NO: 22 |
| B-2 | ATACCAGCTTATTCAATTGGCCGTGTAGATAGTAAGT<br>GCAATCTGATCGGAAGAGCACACGTCTGAACTCCAG<br>TCACCGAGATAGTAAGTGCAATCT | SEQ ID NO: 23 |
| C-1 | ATACCAGCTTATTCAATTAGATAGTAAGTGCAATCTTG<br>ATCGGAAGAGCACACGTCTGAACTCCAGTCACTTAG<br>GCATCAGATAGTAAGTGCAATCT | SEQ ID NO: 24 |
| C-2 | ATACCAGCTTATTCAATTGTATACGGAGTGGATATCG<br>ATCTGTAACGTGAGTGAGATAATGTGATGCATAGTCG<br>TGGAGAGATAGTAAGTGCAATCT | SEQ ID NO: 25 |
| B-1A | ATACCAGCTTATTCAATTAGATAGTAAGTGCAATCTAG<br>ATCGGAAGA | SEQ ID NO: 30 |
| B-1B | GCACACGTCTGAACTCCAGTCACTTAGGCATCAGATA<br>GTAAGTGCAATCT | SEQ ID NO: 31 |
| B-1C | AGATAGTAAGTGCAATCTAGATCGGAAGAGCACACG<br>TCTGAACTCCAGTCACTTAGGCATC | SEQ ID NO: 32 |
| B-1D | ATACCAGCTTATTCAATTAGATAGTAAGTGCAATCTAG<br>ATCGGAAGAGCACACGTCTGAACTCCAGTCACTTAG<br>GCATC | SEQ ID NO: 33 |
| B-1CL | AGATAGTAAGTGCAATCTAGATCGGAAGAGCACACG<br>TCTGAACTCCAGTCACTTAGGCATC<br>(spiegelmer comprising L-deoxyribonucleotides) | SEQ ID NO: 34 |

Without being bound by theory, it is contemplated that in at least one embodiment, when the coated particles comprising an aptamer which selectively binds to the root exudate are exposed to the root exudate, the permeability of the coating can increase, thereby increasing the rate at which the one or more agrochemicals, including but not limited to one or more nutrients, are released from the coated particles. Aptamers have been shown to retain the ability to bind to their target molecules when incorporated into films, including but not limited to polyelectrolyte multilayer films, chitosan or hyaluronan, and to increase the permeability of such films once bound to the target molecules (for example, see Sultan, Y. et al, $Biomacromolecules$ (2009), 10(5): 1149-1154; Foster, A et al, $Polymers$ (2014), 6(5): 1631-1654). In addition, polyelectrolyte multilayer microcapsules including an aptamer embedded in the walls of the microcapsules have shown to exhibit increased permeability when exposed to the target binding partner of the aptamer (for example, see Sultan et al, $Small$ (2011), 7(9): 1219-1226).

It will be clear to the skilled person that other root exudates besides L-serine may be released when other plants besides canola are actively taking up nutrients from the soil, and that such root exudates, aptamers which bind specifically to these root exudates, and coatings containing such aptamers can be readily identified and prepared by the skilled person in view of the teaching herein.

Furthermore, the person of skill in the art will appreciate that, in alternative embodiments of the present invention, root exudates can be identified which are released under conditions other than when the plant is actively taking up nutrients. Again, such root exudates, aptamers which bind specifically to these root exudates, and coatings containing such aptamers can be readily identified and prepared by the skilled person in view of the teaching herein.

For example, in at least one embodiment, the root exudate may be released when the plant is under stress, which may be due to attack by predators or pathogens or in response to the presence of neighbouring plants which may compete for nutrients and other resources. In at least one embodiment, aptamers which bind specifically to those root exudates, coatings containing such aptamers, and particles coated with such coatings can be identified and prepared so as to allow the release from such coated particles, in the presence of appropriate concentrations of such root exudates, of agrochemicals which can act to counteract such stress, including but not limited to materials such as pesticides or herbicides which may repel or kill such predators, pathogens or competing plants.

In at least one embodiment, the coating is applied to the agrochemical particles using a coating apparatus. In at least one embodiment, the coating apparatus includes a particle feeder for delivering agrochemical particles into a coating chamber. In at least one embodiment, the particle feeder is a funnel or hopper, including but not limited to a V-shaped funnel, through which particles of fertilizer can be fed by gravity into the coating chamber.

In at least one embodiment, the coating apparatus includes an injection system for injecting a coating mixture into the coating chamber with a controlled droplet size. In at least one embodiment, the coating mixture is a solution of coating components in a suitable solvent. In at least one embodiment, the coating components comprise a cellulose derivative. In at least one embodiment, the coating components further comprise a fatty acid. In at least one embodiment, the cellulose derivative is ethyl cellulose. In at least one embodiment, the fatty acid is palmitic acid. In at least one embodiment, the ratio by weight of palmitic acid to ethyl cellulose ranges from about 1:10 to about 5:10.

In at least one embodiment, the coating mixture comprises ethyl cellulose at a concentration of about 0.5% weight/volume to about 10% weight/volume and palmitic acid at a concentration of about 0.1% weight/volume in the suitable solvent. Suitable solvents for use in the coating solution are well known in the art and include but are not limited to methanol, isopropanol, butanol, acetone, and other organic solvents. It will be clear to the person skilled in the art that a solvent should be chosen in which the agrochemical particles themselves are insoluble or at most only slightly soluble, and such solvents will be readily recognized and identified by those skilled in the art. In addition, the solvent will advantageously be capable of dissolving the coating components and be readily evaporated so as to deposit the coating components on the agrochemical particles.

In at least one embodiment, the injection system includes a system for delivering the coating mixture to an atomizing injector. In at least one embodiment, the atomizing injector is an ultrasonic atomizing injector. Such atomizing injectors are well known in the art and are commercially available from suppliers including but not limited to Sono-Tek (Milton, NY, USA). In at least one embodiment, the atomizing injector can inject the coating solution into the coating chamber such that the coating solution forms droplets having a diameter ranging from about 10 µm to about 100 µm.

In at least one embodiment, the coating chamber is a multi-stage coating chamber, comprising a series of sequential compartments. Such a chamber allows for successive layers of coating material to be deposited on the particles in a continuous process as the particles pass sequentially through the compartments, thus avoiding the need for a repetitive batch process in order to apply a number of layers of coating to the particles. In at least one embodiment, the coating chamber is a vibrating coating chamber, wherein the vibration can act to agitate the particles and facilitate even and consistent coating of the particles as they pass through successive compartments. In at least one embodiment, the coating chamber is a stackable coating chamber in which successive compartments are stacked upon each other vertically. In this way, the passage of particles from one compartment to the next successive compartment can be facilitated by the action of gravity.

In at least one embodiment, in use, the particles of fertilizer can enter the first compartment of the multi-stage chamber, where coating is applied to the particles. The coated particles can then pass sequentially from the first compartment to subsequent compartments, where additional coating material is applied in each successive compartment until sufficient coating has been applied to the particles. As will be understood by those skilled in the art, the conditions in each compartment, including but not limited to the time of residence of the particles, solvent vapour pressure, temperature, concentration of coating mixture and amount of coating mixture, can be selected and controlled so as to provide the desired thickness, evenness and consistency of coating on the particles. In at least one embodiment, the coating is applied to the particles so as to form a coating with a thickness in a range from about 50 nm to about 5 µm.

In at least one embodiment, the coating apparatus includes a drying chamber in which the coating on the coated particles is cured and/or dried. In at least one embodiment, the coated particles are transferred from the coating chamber to the drying chamber using a moving fluidized bed. As will be understood by the skilled person, heated air can be delivered through pores or micro-holes in the fluidized bed to aid in the drying or curing of the particles on the fluidized bed as the particles are transported to the drying chamber.

In at least one embodiment, the drying chamber includes a source of infrared and/or ultraviolet light to aid in the curing and/or drying of the coating In at least one embodiment, the drying chamber includes or is fluidly connected to a source of heated air. Such heated air can pass over the coated particles in the drying chamber to aid in the curing and/or drying of the coating. In at least one embodiment, the particles are cured and/or dried in the drying chamber under suitable conditions which can be readily identified and chosen by the skilled person, including but not limited to temperature, pressure, air flow, residence time, wavelength of infrared or ultraviolet light, and other conditions known to the skilled person.

In at least one embodiment, the coating apparatus includes an outlet through which the cured or dried coated particles can be discharged from the coating apparatus, for example for packaging or further use.

An embodiment of the present coating apparatus is shown in FIG. 13. The coating apparatus 10 includes a funnel 12 which can receive particles 14 to be coated and can direct the particles to multistage coating chamber 16. Coating material 18 is pumped by pump 20 to ultrasonic injector 22 and injected into the coating chamber 16, where the particles are coated as they pass through successive compartments of the coating chamber 16.

The apparatus 10 further includes a moving fluidized bed 24 which receives the coated particles from the multistage coating chamber. Heated air is fed to the moving fluidized bed 24 from heat exchanger 26 through inlet 28 to aid in curing and/or drying the coated particles. The coated particles are transported on the moving fluidized bed 24 to drying chamber 29, containing radiant elements 30, which can emit infrared or ultraviolet light to aid in curing and drying the coated particles. Once the coating has been cured and/or dried in the drying chamber, the dried particles are discharged through outlet 32.

Advantageously, the present delivery system may provide one or more of the following benefits:
  improved nitrogen use efficiency by crops;
  improved crop productivity; and
  reduced leaching of fertilizer from the soil.

As used herein, the terms "about" or "approximately" as applied to a numerical value or range of values are intended to mean that the recited values can vary within an acceptable degree of error for the quantity measured given the nature or precision of the measurements, such that the variation is considered in the art as equivalent to the recited values and provides the same function or result. For example, the degree of error can be indicated by the number of significant digits provided for the measurement, as is understood in the art, and includes but is not limited to a variation of ±1 in the most precise significant digit reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "substantially" refers to the complete or nearly complete extent or degree of an action, characteristic, property, state, structure, item, or result. For example, an object that is "substantially" aligned would mean that the object is either completely aligned or nearly completely aligned. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, terms indicating relative direction or orientation, including but not limited to "upper", "lower", "top", "bottom", "vertical", "horizontal", "outer", "inner", "front", "back", and the like, are intended to facilitate description of the present invention by indicating relative orientation or direction in usual use or as illustrated, and are not intended to limit the scope of the present invention in any way to such orientations or directions.

EXAMPLES

Other features of the present invention will become apparent from the following non-limiting examples which illustrate, by way of example, the principles of the invention.

Example 1: Temporal Correlation Between L-Serine Release from Roots and Nitrogen Uptake The procedure used is adapted from that described in McRae, G. and C. M. Monreal, *Anal. Bioanal. Chem.* (2011), 400: 2205-2215.

Growth of Canola Plants

A bulk soil sample was collected from the 0-20 cm depth of a fallowed field (uncropped for the last 15 years) located at the Central Experimental Farm of Agriculture and Agri-Food Canada in Ottawa, Ontario. The soil is sandy loam in texture and belongs to the Manotick series of the Haplorthods Great Group. The bulk soil sample was passed through a 1-cm sieve to remove stones and coarse plant fragments and then passed through a 2-mm diameter sieve, mixed thoroughly, and stored for a few days before being placed in plastic pots (20 cm diameter, 15 cm height) and seeded to canola (*Brassica napus*). A porous fabric pocket (8 cm diameter×15 cm height) containing 450 g of soil was placed at the center of each plastic pot, and then 3.8 kg of soil was poured around the pocket in each pot. The fabric pocket was used to help concentrate the root mass, thus facilitating the collection of soil solution resembling that of the crop rhizosphere.

Six to eight seeds of canola were planted inside each fabric pocket; after emergence, only four plants were grown to maturity per pot. Unfertilized canola (4 replicates) and canola fertilized with urea (equivalent of 100 kg N ha$^{-1}$) (4 replicates) were grown under controlled conditions of light (350 µEinstein·m$^{-2}$·s$^{-1}$) and temperature (22° C.) in a greenhouse. Unplanted and unfertilized soil (4 replicates) was kept under the same conditions as a control. Soil pots were kept moist at 80% field capacity throughout the crop's growing season.

Measurement of Nitrogen Uptake

Canola plant tissue samples (stems, leaves, roots) were collected weekly from planted pots, and total nitrogen content of plant tissue samples was determined using the Kjeldahl acid digestion method (Bremner, J. (1960) Determination of nitrogen in soil by the Kjeldahl method. *The Journal of Agricultural Science*, 55(1): 11-33). Standard curves for the accumulation of carbon and nitrogen and associated average weekly and daily rates of nitrogen uptake were determined as described in F. Matus, C. Monreal, M. Lefebvre, S. S. Wu, R. Desjardins and M. DeRosa. 2014. Producing isotopically enriched plant, soil solution and rhizosphere soil materials over a few hours. Commun. Soil Sci. Plant Anal. 45: 865-880.

Soil Solutions from Plant Rhizosphere

Planted and unplanted soil pots were destructively sampled weekly to obtain soil solutions. Roots and soil from the rhizosphere were handled and separated using gloves to minimize contact of soil with hands. Soil solutions were obtained after placing 50 g of moist rhizosphere soil in a Vivacell™ 70 ultrafiltration unit (Sartorius Stedim Biotech, USA) which was subsequently centrifuged at 2,000×g for 10 min at 4° C. The collected solution was placed in a 10-ml glass vial and kept frozen at −18° C. until chemical analysis. Prior to its use, the ultrafiltration unit was conditioned as indicated by the manufacturer.

Measurement of Serine Concentration in Soil Solutions

A thawed sample of soil solution (100 µL) was added to a microcentrifuge tube by pipette and 20 µL of an internal standard solution (2 µg/mL γ-amino butyric acid (GABA) in water) was added. Iodoacetic acid (10 µL; 2.0 mg/mL) was added, followed by saturated sodium bicarbonate buffer (pH 8.4, 50 µL) and the solution was mixed well by vortex after each addition. The solution was incubated in the dark at room temperature for 30 minutes and 5-dimethylaminonaphthalene-1-sulfonyl chloride (dansyl chloride, 50 µL, 4.0 mg/mL in acetone) was added to form the dansyl derivative. The solution was mixed well by vortex, incubated at 60° C. for 50 minutes, and again mixed well by vortex. The mixture was centrifuged at 13,000 rpm for 5 minutes and 150 µL of the supernatant was pipetted into a 96-well plate and analyzed by liquid chromatography-tandem mass spectrometry (LC-MS/MS; AB Sciex, Concord, ON, Canada).

Calibration standards and quality control samples of amino acids, including serine and GABA, were prepared from individual stock solutions (100 µg/mL in water, 25% methanol in water, or 25 mM NaHCO$_3$) over a concentration range of 5.0 to 500 ng/mL (20.0 to 500 ng/mL for serine, cysteine and tyrosine). Blanks were extracted prior to LC-MS/MS analysis, and dansyl derivatives were prepared as described above.

Reverse-phase chromatographic separation of dansyl amino acid derivatives was performed on a Shimadzu Prominence HPLC system (Shimadzu Corp, Kyoto, Japan) equipped with two LC-20AD pumps, a DGU-20A3 degasser, a SIL-20AC autosampler, a CBM-20A controller and a Thermo Betasil C18 column, 150×2.1 mm, 3 µm. The column was eluted with mobile phase A (Milli-Q water/formic acid (100:0.1)) and mobile phase B (acetonitrile/formic acid (100:0.1)). The chromatographic flow rate was set to 0.25 mL/min, and the gradient was programmed as follows: mobile phase B started at 77%, decreasing to 40% over 13 min, then decreased to 10% over 15 min, 15.5 min and 15.7 min, increased to 77% over 15.7 minutes and then 19.5 min. All gradient condition used a flow of 0.2 mL/min. The mobile phase eluant was directed from the HPLC column through a switch valve and diverted to waste for the first 5 min, and to the mass spectrometer ion source for the remainder of the chromatographic run. An injection volume of 10 μl was used.

Dansyl amino acid derivatives were infused directly into the mass spectrometer via an infusion pump. MS/MS parameters were established and optimized individually for each dansyl amino acid derivative. The turbo ion spray ionization source was operated at 4,500 V in positive mode. All MS/MS chromatographic data was collected in multiple-reaction monitoring (MRM) mode with a dwell time of 50 ms for each ion transition.

Results

Figure 1:
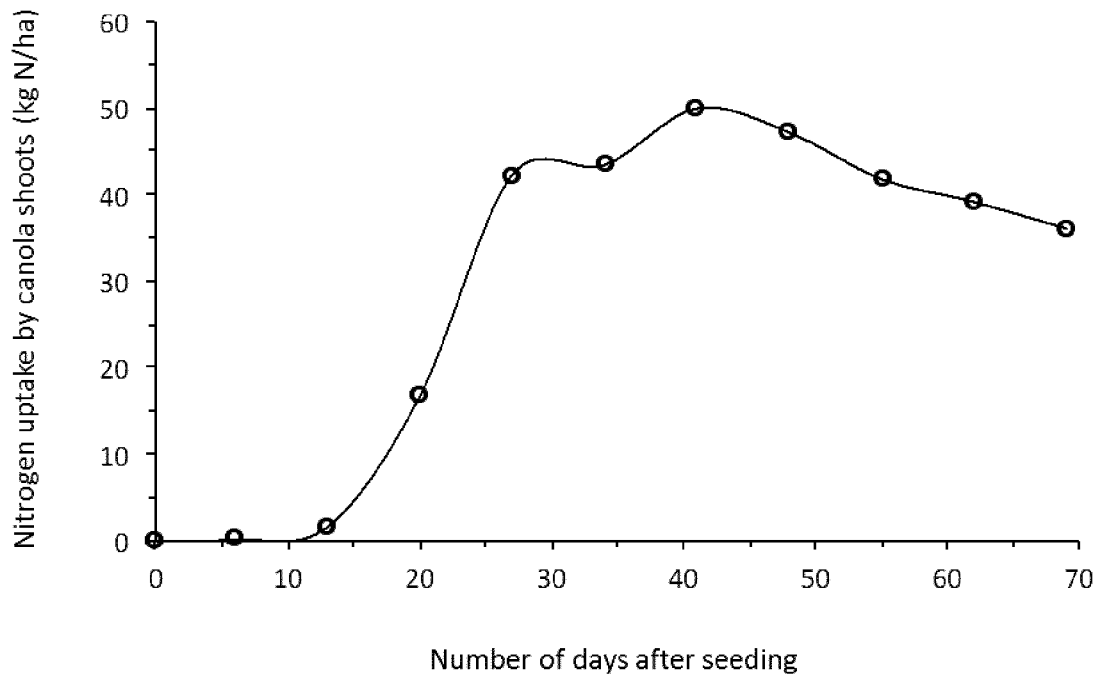
FIG. 1 is a graph showing cumulative uptake of nitrogen by canola shoots over time during growth.
Figure 3A:
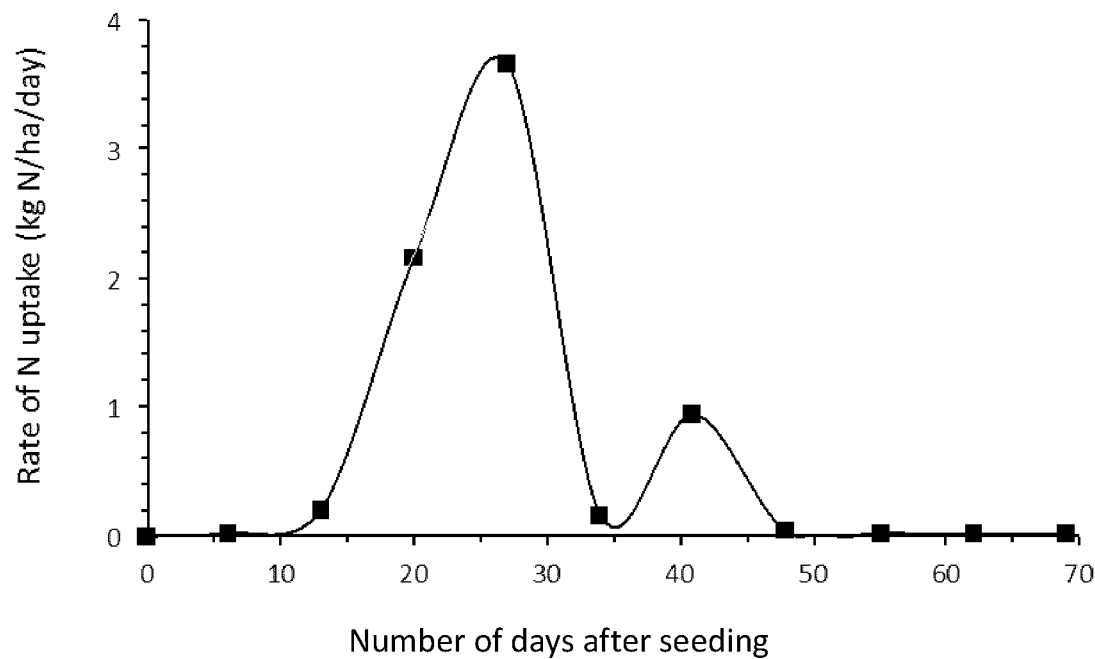
FIG. 3A is a graph showing the rate of nitrogen uptake by canola over time during growth.

FIG. 1 shows the cumulative uptake of nitrogen by unfertilized canola shoots over time after seeding and the data presented indicate that more than 90% of the nitrogen provided by urea fertilizer is taken up by canola in the first 40 days of growth. FIG. 3A shows the rate of nitrogen uptake by unfertilized canola plants over time after seeding, which ranged from a few grams of nitrogen per hectare per day to just under 4 kg of nitrogen per hectare per day. The rate of absorption of nitrogen by fertilized canola plants was more than twice the rate of absorption by unfertilized plants as seen from the data shown in Table 1-1 below.

TABLE 1-1

Rates of nitrogen absorption in fertilized and unfertilized canola plants

| Day of growth | Rate of nitrogen absorption (dN/dt (kg N ha$^{-1}$d$^{-1}$)) | |
|---|---|---|
| | Unfertilized (0 kg N) | Fertilized (100 kg N) |
| 0 | 0.00 | 0.00 |
| 6 | 0.02 | 0.02 |
| 13 | 0.20 | 0.23 |
| 20 | 2.16 | 2.26 |
| 27 | 3.66 | 9.29 |
| 34 | 0.16 | 1.59 |
| 41 | 0.94 | 0.59 |
| 48 | 0.03 | 0.02 |
| 55 | 0.02 | 0.33 |
| 62 | 0.01 | 0.01 |
| 69 | 0.01 | 0.01 |

Figure 2:
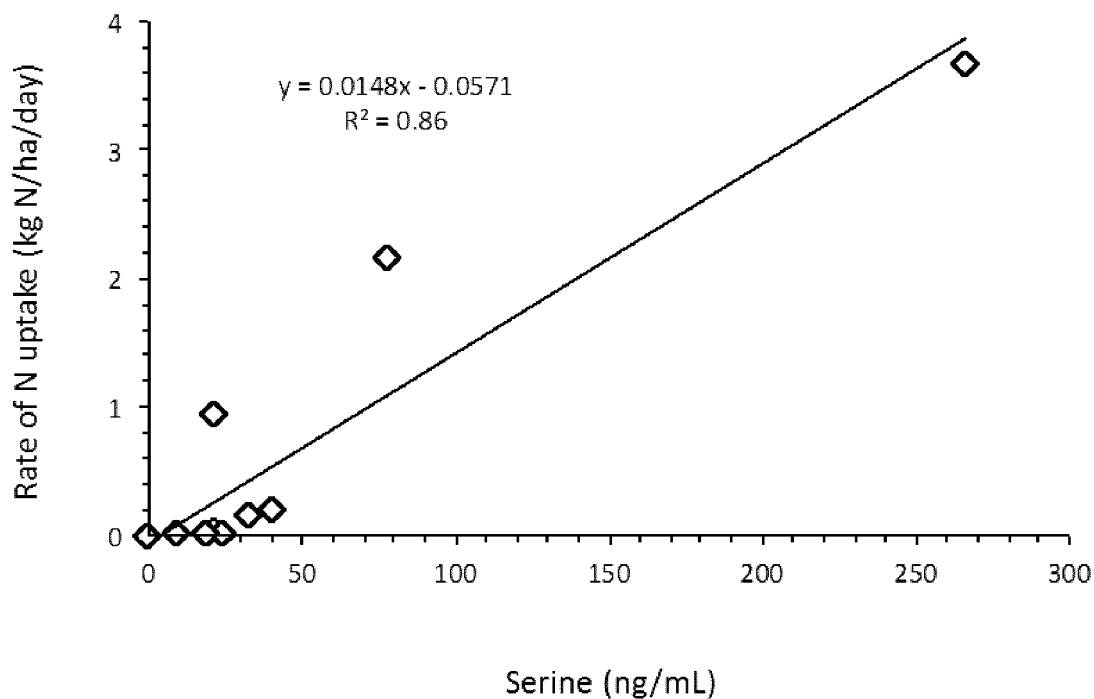
FIG. 2 is a graph showing the correlation between the rate of nitrogen uptake by canola and the concentration of serine in soil solution from the rhizosphere of the canola plants over time during growth.
Figure 3B:
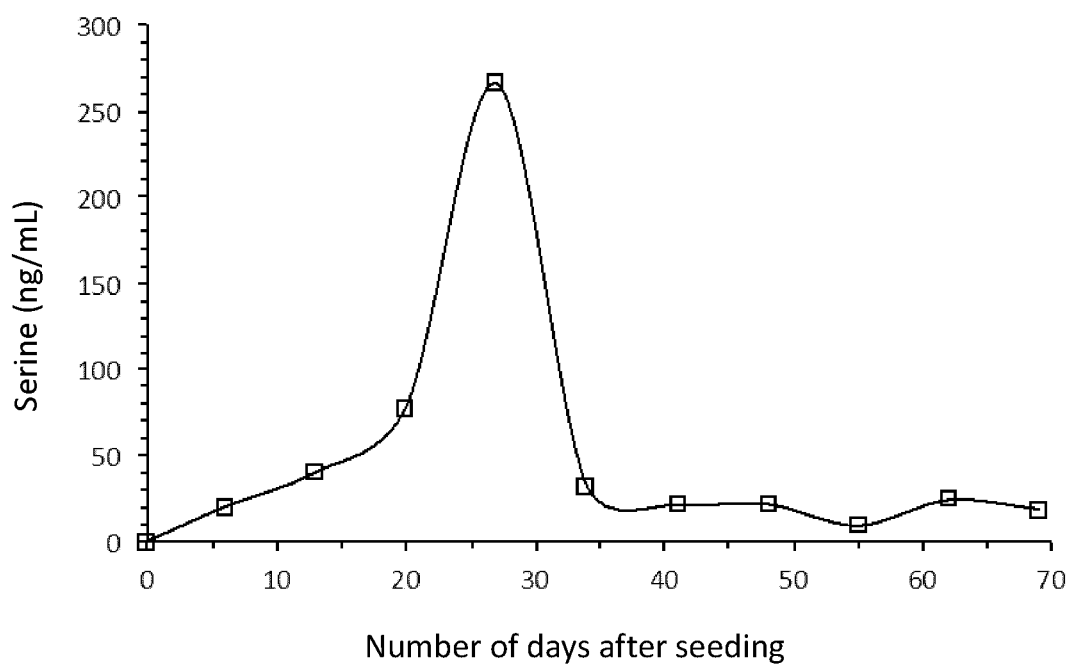
FIG. 3B is a graph showing the concentration of serine in soil solution collected from the rhizosphere of canola plants over time during growth.

FIG. 3B shows changes in the concentration of serine in soil solution samples obtained from the rhizosphere of unfertilized canola plants over time after seeding. The serine concentrations ranged from about 10 ng/mL to about 270 ng/mL. By comparison, the background concentration of serine in soil solution from unplanted soil before seeding and after harvest of the canola plants was found to be about 10 ng/mL. As seen from FIGS. 3A and 3B, both the rate of nitrogen uptake and the serine concentration peaked at about 28 days after seeding. FIG. 2 shows a plot of the rate of nitrogen uptake by unfertilized canola plants vs. soil serine concentration in the rhizosphere of the unfertilized canola plants over time after seeding, and indicates that there is a good correlation between these parameters ($r^2$=0.86).

Example 2: Preparation of DNA Libraries

DNA Synthesis

DNA synthesis was carried out on a MerMade™ 6 oligonucleotide synthesizer (BioAutomation Corporation) using standard phosphoramidite chemistry, as well known in the art (for example, see Caruthers, M. H., et al, Methods in Enzymology (1987), 154: 287-313). All nucleoside phosphoramidites, modifiers, and reagents were obtained from Glen Research, 1000 Å controlled pore glass (CPG) 1 μmol scale columns were obtained from BioAutomation, and synthesis grade acetonitrile was obtained from VWR. 28% ammonium hydroxide solution was obtained from Sigma-Aldrich (Oakville, ON, Canada).

Three DNA libraries were prepared as starting libraries for the SELEX procedure. The sequences of Library A have the sequence 5'-AGCAGCACAGAGGTCAGATG- (SEQ ID NO:1) followed by a randomized sequence of 40 nucleotides in which each nucleotide (A, T, C, G) has an equal chance of appearing at each position, followed by the sequence -CCTATGCGTGCTACCGTGAA-3' (SEQ ID NO:2). A forward primer for use in PCR amplification was prepared having the sequence 5'-AGCAGCACAGAGGTCAGATG-3' (SEQ ID NO:3), in which the 5' nucleoside is labeled with the fluorescent tag 6-FAM (6-carboxyfluorescein). A reverse primer was also prepared having the sequence TTCACGGTAGCACGCATAGG (SEQ ID NO:4), to the 5'-end of which a dA$_{20}$ sequence is attached by an 18-atom hexaethylene glycol spacer.

Libraries B and C are based on a DNA library previously used to identify aptamers with binding affinity to homocysteine (McKeague, M. et al, RSC Adv. (2013), 3(46): 24415). Library B includes the combined DNA pools from the last two rounds of selection of this library. The corresponding forward and reverse primers identified in McKeague, M. et al, RSC Adv. (2013), 3(46): 24415 were used for PCR amplification. Library C is a randomized library based on an aptamer selected from this DNA library and identified as having binding affinity to homocysteine and to serine, which has the sequence (SEQ ID NO: 5)
5'-ATACCAGCTTATTCAATTGTGGAAAGCCGAATGTGATTAGGGA

CCAGTGGAGAAGTAGTACGGACTGACCTCGCGTGTAAGATAGTAAG

TGCAATCT-3'.

Library C was prepared by introducing a 15% randomization into nucleotides 19 to 79 inclusive of SEQ ID NO:5 (identified above as bold, underlined text). Thus, as this portion of the oligonucleotide was being synthesized, the nucleotide originally found in any particular position of the sequence could be randomly replaced to an extent of up to 15% with one of an equimolar mixture of the other three nucleotides. A forward primer for use in PCR amplification was prepared having the sequence 5'-ATACCAGCTTATTCAATT-3' (SEQ ID NO:6) and labeled with the fluorescent tag 6-FAM (6-carboxyfluorescein) at the 5' end. A reverse primer was also prepared having the sequence AGATTGCACTTACTATCT (SEQ ID NO:7), to the 5' end of which a dA$_{20}$ sequence is attached by an 18-atom hexaethylene glycol spacer.

After DNA synthesis, the CPG beads were transferred from the synthesis columns to microfuge tubes using needles, and 1 mL of 28% ammonium hydroxide solution was added. The beads were vortexed, vented, and heated at 55° C. for 24 hours. After cooling to room temperature, the beads were centrifuged at 13000×g for 5 minutes, and the supernatant collected. The beads were washed with 1 mL of deionized water, centrifuged again, and the supernatant collected. The collected DNA solutions were dried down on a Savant AE2010 SpeedVac™.

Purification of DNA by Polyacrylamide Gel Electrophoresis (PAGE)

Polyacrylamide gel electrophoresis (PAGE) reagents (acrylamide/bis-acrylamide 40% solution, tris(hydroxymethyl)amino methane (Tris), boric acid, ethylenediamine tetraacetic acid (EDTA) and N,N,N',N'-tetramethylethylenediamine (TEMED)) were obtained from BioShop Canada (Burlington, ON, Canada). Formamide and 3 kDa cutoff Amicon™ Ultra centrifugal filter columns were obtained from Sigma-Aldrich (Oakville, ON, Canada).

The synthesized DNA libraries were purified using 12% denaturing PAGE gels. The gel solution is composed of 31.5 g urea, 23.5 mL acrylamide (acrylamide/bis-acrylamide 40% solution), 15 mL 5×TBE buffer (45 mM Tris, 45 mM boric acid, 1 mM EDTA), and 14 mL deionized water for 2 gels. This solution is heated to 37° C. with magnetic stirring and filtered through Whatman No. 1 filter paper. Once cooled to room temperature, 450 µL of 10% ammonium persulfate are added, and 35 µL of N,N,N',N'-tetramethylethylenediamine (TEMED). The solution is quickly poured between pre-assembled glass plates, and a plastic comb is added to form the loading well. The gels are left to polymerize at room temperature for approximately 30 minutes. After polymerization, the plastic combs are removed, and the wells rinsed with deionized water. The glass plates are transferred to a Hoefer™ SE 600 Chroma™ Standard Dual gel electrophoresis unit (Hoefer). The gels are pre-run at a constant current of 30 mA (~300 volts) for 20 minutes. The DNA to be purified is re-suspended in deionized water, mixed 1:1 with formamide, and heated to 90° C. prior to loading. The gels are run at a constant current of 30 mA (or ~300 volts) until an 18-base fluorescently tagged marker moves ¾ through the gel. The gels are imaged using an Alpha Innotech Alphalmager™ EC instrument, and the bands of interest excised from the gels. Each band is broken into pieces, and deionized water is added to extract the DNA from the gel pieces over 24 hours on a 37° C. shaking incubator. Following this incubation, the gel slurry is filtered through 0.22 µm cellulose acetate syringe filters to remove gel fragments. The DNA solution was frozen in liquid nitrogen and dried on a Labconco FreeZone™ lyophilizer. To remove salts, the DNA was resuspended in a minimum amount of deionized water and filtered using 3 kDa cutoff Amicon™ Ultra centrifugal filter columns. The DNA was then quantified at 260 nm using a Varian Cary 300 Bio UV-Vis spectrophotometer, and the synthesis was confirmed using ESI/LC/MS.

Example 3: Selection of Aptamers

Coupling of L-Serine to Sepharose™ Beads

For use in selection of selectively binding DNA aptamers from the DNA libraries discussed above, the small molecule L-serine was immobilized on Sepharose™ resin for consistency with the resin used in the original selection of Libraries B and C for binding to homocysteine, so as to minimize non-specific binding with DNA from those libraries.

All solutions used during coupling are cooled to 4° C. N-hydroxysuccinimide (NHS)-activated Sepharose™ 4 Fast Flow (Sigma-Aldrich) is washed with 10-15 medium volumes of 1 mM HCl. 115 mM L-serine in coupling buffer (0.2 M NaHCO₃, 0.5 M NaCl, pH 8.3) is mixed with the resin at a ratio of 0.5:1 coupling solution to resin. The coupling is allowed to take place for 4 hours on a shaker at room temperature. After coupling, the post-coupling solution is removed and set aside to verify coupling efficiency. Any unreacted groups are blocked using 0.1 M Tris-HCl on a shaker for 3 hours. After blocking, the resin is washed using 3× medium volumes of 0.1 M Tris-HCl, pH 8-9, followed by a wash with 0.1 M acetate, 0.5 M NaCl, pH 4-5. These buffers are used alternately for a total of 8 column washes. The column is then transferred to SELEX buffer (50 mM Tris-HCl, 500 mM NaCl, 5 mM $MgCl_2$, pH 7.4) and stored at 4° C. until use. This procedure was repeated to generate resin conjugated to glycine and Tris as controls.

Successful coupling of L-serine to the resin was determined by a colorimetric reaction of serine with ninhydrin. A range of L-serine concentrations (70-230 mM) were prepared in coupling buffer (0.2 M $NaHCO_3$, 0.5 M NaCl, pH 8.3) and mixed 1:1 with a ninhydrin solution prepared by adding 0.1 g of ninhydrin to 10 mL of glacial acetic acid and heating slightly until dissolved. Coupling buffer mixed with ninhydrin was used as a control. The solutions were left at room temperature 5-10 minutes before examining the colour change. A standard curve was generated by plotting serine concentration against the absorbance (570 nm) of the chromophore formed in the reaction. By comparing the serine concentrations of the pre-coupling and post-coupling solutions, the coupling efficiency of serine to the resin was determined to be 16-23 µmol/mL ligand density.

SELEX Identification of Aptamers

The SELEX (Systematic Evolution of Ligands by EXponential enrichment) procedure to identify aptamers specific for L-serine was carried out in separate experiments, each starting with one of the DNA pools (Library A, Library B or Library C) of Example 2. Before each round of selection, each DNA pool in SELEX buffer (50 mM Tris-HCl, 500 mM NaCl, 5 mM $MgCl_2$, pH 7.4) was denatured at 90° C. for 5 minutes, cooled at 4° C. for 10 minutes, and brought to room temperature for 15 minutes. A 5 µL sample of the DNA starting pool was set aside for fluorescence analysis. Sepharose™ beads coupled to Tris (herein referred to as a "negative column") or Sepharose™ beads coupled to L-serine prepared as described above (herein referred to as a "positive column") were placed in 0.22 µm Costar™ Spin-X™ cellulose acetate centrifuge filters (Corning Incorporated) and washed 3 times with SELEX buffer prior to beginning the SELEX procedure.

The starting DNA pool for each round of selection was incubated with a negative column of Sepharose™ beads coupled to Tris for 30 minutes shaking at room temperature in SELEX buffer, to remove DNA sequences which bind non-specifically to Sepharose™ or to Tris. The beads were centrifuged at 14000×g for 1 minute. The DNA solution for each library that passed through the negative column of Sepharose™ beads coupled to Tris was added to a positive column of Sepharose™ beads coupled to L-serine and incubated for 1 hour shaking at room temperature. The column was centrifuged at 5000×g for 1 minute, collecting the flow-through. Four additional washes using SELEX buffer were also collected. The fourth wash was centrifuged at 14000×g for 1 minute. DNA was eluted from the positive column by incubating the column with 100 mM L-serine for 10 minutes and centrifuging at 14000×g to collect filtrate. This was repeated for 5 elutions. Eluates from an additional 5 elutions were collected using 7M urea at 90° C. to ensure most DNA was removed from the positive column.

The fluorescence of the eluates as well as of the starting pool were measured using a Fluorolog™ Fluorescence Spectrophotometer (Horiba Jobin Yvon, USA) with an excitation wavelength of 490 nm, emission wavelength of 520 nm, and slit widths of 5 nm. The amount of DNA bound to the columns as a measure of round-to-round enrichment could be followed by calculating the % DNA bound as follows:

$$\% \text{ DNA Bound} = \frac{f \text{ elution}}{f \text{ pool}} \times 100\%$$

where "f elution" is the sum of the fluorescent intensities of all eluates, and "f pool" is the total fluorescent intensity of the starting pool of the SELEX round.

PCR Amplification of DNA Pools

The eluates were desalted using 3 kDa cutoff Amicon™ Ultra centrifugal filter columns before being amplified using the polymerase chain reaction (PCR). Reagents for PCR (25 mM MgCl$_2$, 10 mM dNTP mix, and Taq DNA polymerase) were obtained from BioShop Canada (Burlington, ON, Canada). PCR reactions were prepared to a volume of 100 µL by combining: 50 µL FluMag buffer (0.2 M Tris-HCl pH 9, 0.1 M KCl, 2% Triton™ X-100) (Stoltenburg, R.; Reinemann, C.; Strehlitz, B. *Anal. Bioanal. Chem.* 2005, 383 (1), 83-91), 37 µL deionized water, 8 µL 25 mM MgCl$_2$, 2 µL of dNTP mix, 0.5 µL of fluorescently labelled forward primer, 0.5 µL of polyA reverse primer, 1 µL of Taq DNA polymerase, and 1 µL of the DNA library to be amplified. Positive and negative control reactions were run by substituting 1 µL of control pool, or deionized water in place of the SELEX pool, respectively.

PCR was run on a Mastercycler™ ep gradient (Eppendorf, Hauppauge, NY, USA). The PCR conditions for Library A were: denaturation at 94° C. for 5 minutes; 25 cycles of (melting at 94° C. for 30 seconds, annealing at 54° C. for 30 seconds, extension at 74° C. for 20 seconds); final extension at 72° C. for 5 minutes. For Libraries B and C, the PCR conditions were: denaturation at 94° C. for 10 minutes; 25 cycles of (melting at 94° C. for 1 minute, annealing at 47° C. for 1 minute, extension at 72° C. for 1 minute); final extension at 72° C. for 10 minutes. The PCR conditions were optimized for each primer set.

After PCR, the reaction mixtures were dried down on a Savant™ AE2010 SpeedVac™. They were resuspended in a minimum volume of deionized water, mixed 1:1 with formamide, and run on 12% denaturing PAGE gels as described in Example 2, cutting out the fluorescent band. This DNA was eluted from the PAGE gels, and desalted using 3 kDa cutoff Amicon™ Ultra centrifugal filter columns as previously described. The DNA was quantified at 260 nm using a Varian Cary 300 Bio UV-Vis spectrophotometer, and used as the starting pool for the subsequent SELEX round.

The stringency of binding between the DNA aptamers and the target was increased in each round of selection by decreasing the amount of target and decreasing the incubation time of the pool and target. In addition, the L-serine-conjugated resin was diluted 100× to reduce the concentration of L-serine, and the concentration of the DNA library was increased to add selective pressure.

In the penultimate selection round for each SELEX experiment, counter selections against glycine and L-threonine were performed, to eliminate aptamers which do not selectively bind L-serine compared to glycine or L-threonine. Prior to eluting the positive column of Sepharose™ beads coupled to L-serine with L-serine, 100 µL solution of glycine and L-threonine (100 mM each) were added to positive column, incubated 10 minutes, centrifuged, and washed once with SELEX buffer. The eluate and wash of this counter selection were kept for high-throughput sequencing.

The target incubation step in the final round of each SELEX experiment was performed using a 1:1 mixture of soil solution (obtained from sandy loam soil, uncropped for 15 years) and SELEX buffer, to elute only aptamers which are capable of binding to L-serine when exposed to soil-like conditions.

The SELEX experimental conditions for each DNA library are provided below.

Library A SELEX experimental conditions:
Round 1: 5 nmol DNA
  500 µL bead slurry
  1 hour incubation time
  10 Elutions (500 µL) with 10 mM L-serine
  2 Elutions with 7M Urea
Round 2: 1 nmol DNA
  500 µL bead slurry
  1 hour incubation time
  10 Elutions (500 µL) with 10 mM L-serine
  2 Elutions with 7M Urea
Round 3: 200 µmol DNA
  500 µL bead slurry
  1 hour incubation time
  10 Elutions (500 µL) with 10 mM L-serine
  2 Elutions with 7M Urea
Round 4: 200 µmol DNA
  500 µL bead slurry
  30 min incubation time
  10 Elutions (500 µL) with 10 mM L-serine
  2 Elutions with 7M Urea
Round 5: 200 µmol DNA
  500 µL bead slurry
  30 min incubation time
  10 Elutions (500 µL) with 100 mM L-serine
  2 Elutions with 7M Urea
Round 6: 200 µmol DNA
  500 µL bead slurry
  30 min incubation time
  5 Elutions (500 µL) with 100 mM L-serine
  5 Elutions with 7M Urea
Round 7: 200 µmol DNA
  500 µL bead slurry
  20 min incubation time
  5 Elutions (500 µL) with 100 mM L-serine
  5 Elutions with 7M Urea
Round 8: 200 µmol DNA (125 µmol L-serine-eluted, 75 µmol urea-eluted)
  500 µL bead slurry
  20 min incubation time
  5 Elutions (500 µL) with 100 mM L-serine
  5 Elutions with 7M urea
Round 9: 200 µmol DNA (125 µmol L-serine-eluted, 75 µmol urea-eluted)
  500 µL bead slurry
  Extra negative column
  20 min incubation time
  5 Elutions (500 µL) with 100 mM L-serine
  5 Elutions with 7M urea
Round 10: 200 µmol DNA (125 µmol L-serine-eluted, 75 µmol urea-eluted)
  100× Diluted beads
  Extra negative column
  Counter selections with 100 mM glycine and L-threonine
  20 min incubation time
  5 Elutions (100 µL) with 100 mM L-serine
  5 Elutions with 7M urea
Round 11: 200 µmol DNA (125 µmol L-serine-eluted, 75 µmol urea-eluted)
  100× Diluted beads 20 min incubation time in 1:1 Soil Extract:SELEX buffer
5 Elutions (100 µL) with 100 mM L-serine
5 Elutions with 7M urea Library B SELEX Experimental Conditions:
Round 1: 1 nmol DNA
  250 µL bead slurry
  1 hour incubation time
  5 Elutions (100 µL) with 100 mM L-serine
  5 Elutions with 7M urea
Round 2: 200 µmol DNA
  250 µL bead slurry
  1 hour incubation time
  5 Elutions (100 µL) with 100 mM L-serine
  5 Elutions with 7M urea
Round 3: 200 µmol DNA (125 µmol L-serine-eluted, 75 µmol urea-eluted)
  250 µL bead slurry
  1 hour incubation time
  5 Elutions (100 µL) with 100 mM L-serine
  5 Elutions with 7M urea
Round 4: 200 µmol DNA (125 µmol L-serine-eluted, 75 µmol urea-eluted)
  100× Diluted beads
  Counter selections with 100 mM glycine and L-threonine
  20 min incubation time
  5 Elutions (100 µL) with 100 mM L-serine
  5 Elutions with 7M urea
Round 5: 200 µmol DNA (125 µmol L-serine-eluted, 75 µmol urea-eluted)
  100× Diluted beads
  20 min incubation time in 1:1 Soil Extract: SELEX buffer
  5 Elutions (100 µL) with 100 mM L-serine
  5 Elutions with 7M urea Library C SELEX Experimental Conditions:
Round 1: 1 nmol DNA
  100 µL bead slurry
  1 hour incubation time
  5 Elutions (100 µL) with 100 mM L-serine
  5 Elutions with 7M urea
Round 2: 200 µmol DNA
  100 µL bead slurry
  1 hour incubation time
  5 Elutions (100 µL) with 100 mM L-serine
  5 Elutions with 7M urea
Round 3: 200 µmol DNA (125 µmol L-serine-eluted, 75 µmol urea-eluted)
  100 µL bead slurry
  1 hour incubation time
  5 Elutions (100 µL) with 100 mM L-serine
  5 Elutions with 7M urea
Round 4: 500 µmol DNA (300 µmol L-serine-eluted, 200 µmol urea-eluted)
  100× Diluted beads
  30 minute incubation time
  5 Elutions (100 µL) with 100 mM L-serine
  5 Elutions with 7M urea
Round 5: 500 µmol DNA (125 µmol L-serine-eluted, 75 µmol urea-eluted)
  100× Diluted beads
  30 minute incubation time
  5 Elutions (100 µL) with 100 mM L-serine
  5 Elutions with 7M urea
Round 6: 500 µmol DNA (125 µmol L-serine-eluted, 75 µmol urea-eluted)
  100× Diluted beads
  30 minute incubation time
  5 Elutions (100 µL) with 100 mM L-serine
  5 Elutions with 7M urea
Round 7: 500 µmol DNA (125 µmol L-serine-eluted, 75 µmol urea-eluted)
  100× Diluted beads
  Counter selections with 100 mM glycine and L-threonine
  20 minute incubation time
  5 Elutions (100 µL) with 100 mM L-serine
  5 Elutions with 7M urea
Round 8: 500 µmol DNA (125 µmol L-serine-eluted, 75 µmol urea-eluted)
  100× Diluted beads
  20 min incubation time in 1:1 Soil Extract: SELEX buffer
  5 Elutions (100 µL) with 100 mM L-serine
  5 Elutions with 7M urea Example 4: High Throughput Sequencing of Aptamers Because a small proportion (less than 1%) of sequences in each DNA library were found to bind L-serine, high throughput sequencing of selected DNA pools formed during the SELEX procedures was carried out using a HiSeq™ 2000 PE100 sequencer (Illumina). This allowed identification of L-serine binding sequences which were found to occur with high frequency, or which were enriched over consecutive rounds of selection. In addition, non-specific binding sequences could be identified and eliminated.

A total of twelve DNA pools (four DNA pools generated from each DNA library (A, B and C) during the SELEX procedure) were selected for analysis by high throughput sequencing. The selected pools included each original starting DNA pool prior to selection (round 0), which was analyzed for sequence diversity and base distribution to provide a starting point to monitor enrichment in subsequent rounds. Also selected for high throughput sequencing were the DNA pools eluted with L-serine from the positive column of Sepharose™ beads coupled to L-serine in the penultimate round of selection after the column had been eluted with glycine and L-threonine and the DNA pools eluted from the positive column with L-serine after incubation of the column with soil extract in the final round of selection, to provide sequences which might bind selectively to serine under soil-like conditions. Finally, the combined DNA pools from elution of the positive column of Sepharose™ beads coupled to L-serine with glycine and L-threonine and the subsequent wash of the positive column in the penultimate round of selection, and from elution of the negative column of Sepharose™ beads coupled to Tris in the last round of selection with 7M urea were selected for high throughput sequencing, so that sequences binding unwanted targets such as Tris, Sepharose™, glycine and L-threonine could be identified and eliminated from further analysis.

Preparing DNA Libraries for Sequencing

Adapter sequences (IDT) having the sequences shown in Table 4-1 were selected and purified by PAGE-purified with mass confirmation by mass spectrometry. Index tags are underlined.

TABLE 4-1

Adapter sequences for high throughput sequencing

| Adapter | Sequence | Identifier |
|---|---|---|
| F1 | AATGATACGGCGACCACCGAGATCTACACTCTTT CCCTACACGACGCTCTTCCGATCTATACCAGCTT ATTCAATT | SEQ ID NO: 8 |
| F2 | AATGATACGGCGACCACCGAGATCTACACTCTTT CCCTACACGACGCTCTTCCGATCTNATACCAGCT TATTCAATT | SEQ ID NO: 9 |
| F3 | AATGATACGGCGACCACCGAGATCTACACTCTTT CCCTACACGACGCTCTTCCGATCTNNAGCAGCA CAGAGGTCAGATG | SEQ ID NO: 10 |
| F4 | AATGATACGGCGACCACCGAGATCTACACTCTTT CCCTACACGACGCTCTTCCGATCTNNNAGCAGC ACAGAGGTCAGATG | SEQ ID NO: 11 |
| R1 | CAAGCAGAAGACGGCATACGAGATCGTGATGTG ACTGGAGTTCAGACGTGTGCTCTTCCGATCAGAT TGCACTTACTATCT | SEQ ID NO: 12 |
| R2 | CAAGCAGAAGACGGCATACGAGATACATCGGTG ACTGGAGTTCAGACGTGTGCTCTTCCGATCAGAT TGCACTTACTATCT | SEQ ID NO: 13 |
| R3 | CAAGCAGAAGACGGCATACGAGATGCCTAAGTG ACTGGAGTTCAGACGTGTGCTCTTCCGATCNAG ATTGCACTTACTATCT | SEQ ID NO: 14 |
| R4 | CAAGCAGAAGACGGCATACGAGATTGGTCAGTG ACTGGAGTTCAGACGTGTGCTCTTCCGATCNAG ATTGCACTTACTATCT | SEQ ID NO: 15 |
| R5 | CAAGCAGAAGACGGCATACGAGATCACTGTGTG ACTGGAGTTCAGACGTGTGCTCTTCCGATCNNTT CACGGTAGCACGCATAGG | SEQ ID NO: 16 |
| R6 | CAAGCAGAAGACGGCATACGAGATATTGGCGTG ACTGGAGTTCAGACGTGTGCTCTTCCGATCNNTT CACGGTAGCACGCATAGG | SEQ ID NO: 17 |
| R7 | CAAGCAGAAGACGGCATACGAGATGATCTGGTG ACTGGAGTTCAGACGTGTGCTCTTCCGATCNNNT TCACGGTAGCACGCATAGG | SEQ ID NO: 18 |
| R8 | CAAGCAGAAGACGGCATACGAGATTCAAGTGTG ACTGGAGTTCAGACGTGTGCTCTTCCGATCNNNT TCACGGTAGCACGCATAGG | SEQ ID NO: 19 |

The adapters were added to DNA libraries by PCR amplification. For Library A, a master mix was made containing: 350 μL FluMag buffer (0.2 M Tris-HCl pH 9, 0.1 M KCl, 2% Triton™ X-100), 260 μL deionized water, 56 μL MgCl$_2$, 14 μL dNTPs, 10.5 μL forward primer, 10.5 μL reverse primer, and 7 μL Taq. The master mix was mixed well and 95 μL was removed for a PCR control. To the rest of the master mix, template was added (6 μL of the original pool, or 36 μL of a SELEX round library) and divided into 6 reactions. The PCR conditions were as described in Example 3, using a gradient annealing temperature from 54.1° C. to 56.4° C. and a total of 20 cycles. For Library C, the same master mix was used, with 20 μL of template added (6 μL of the round 1 pool) and divided into 6 reactions. The cycle used was as described in Example 3 with a gradient of annealing temperatures from 49-59° C. For Library B, a master mix was made containing: 350 μL FluMag buffer, 266 μL deionized water, 56 μL MgCl$_2$, 14 μL dNTPs, 15 μL forward primer, 15 μL reverse primer, and 7 μL Taq. After removing 95 μL for a PCR control, 20-28 μL of each template was added, and divided in 6 reactions. The cycle used was as described in Example 3 with gradient annealing temperatures from 49-59° C. for 20 cycles.

After each PCR, like reactions were combined and dried down on a Savant™ AE2010 SpeedVac. The DNA libraries including attached Illumina adapters were purified and extracted from denaturing PAGE gels as described in Example 2, using 8% gels to accommodate the longer sequence length. The 8% gels were composed of 8 mL acrylamide (acrylamide/bis-acrylamide 40% solution), 15.25 g Urea, 7.5 mL 5×TBE buffer, and 21.5 mL deionized water for one gel. After purification and extraction from the 8% denaturing PAGE gels, each DNA library was quantified using a Nanodrop spectrophotometer. The adapters used with each DNA pool are identified in Table 4-2.

All DNA libraries were diluted to a concentration of 5 ng/μL, and 40 ng of each library was added to a microwell plate. Libraries A and C were sequenced simultaneously, while Library B was sequenced in a separate procedure. The percentages of each pool included in each high throughput sequencing experiment are listed in Table 4-2.

TABLE 4-2

Adapters attached to individual DNA pools

| Library | DNA pool | Percentage of total (%) | Adapters |
|---|---|---|---|
| Library A | original starting DNA pool prior to selection (round 0) | 31.8 | F3 + R5 |
| | DNA pool eluted with L-serine after elution with glycine and L-threonine (round 10) | 17.37 | F3 + R6 |
| | DNA pool eluted with L-serine after incubation in soil solution (round 11) | 25.98 | F4 + R8 |
| | combined DNA pools from elution with glycine and L-threonine and the subsequent wash (round 10), and from elution of the negative column (round 11) | 24.86 | F4 + R7 |
| Library B | original starting DNA pool prior to selection (round 0) | 20.5 | F1 + R1 |
| | DNA pool eluted with L-serine after elution with glycine and L-threonine (round 4) | 23.12 | F1 + R2 |
| | DNA pool eluted with L-serine after incubation in soil solution (round 5) | 27.08 | F2 + R3 |
| | combined DNA pools from elution with glycine and L-threonine and the subsequent wash (round 4), and from elution of the negative column (round 5) | 29.29 | F2 + R4 |
| Library C | original starting DNA pool prior to selection (round 0) | 13.66 | F1 + R1 |
| | DNA pool eluted with L-serine after elution with glycine and L-threonine (round 7) | 22.19 | F1 + R2 |
| | DNA pool eluted with L-serine after incubation in soil solution (round 8) | 26.33 | F2 + R3 |
| | combined DNA pools from elution with glycine and L-threonine and the subsequent wash (round 7), and from elution of the negative column (round 8) | 37.82 | F2 + R4 |

Example 5: Analysis of High Throughput Sequencing Data

Sequencing data in the form of .fastq files was analyzed with AptaCluster software (Hoinka, J. et al, *Res. Comput. Mol. Biol.* 2014, 8394, 115-128; Hoinka, J. et al, *Nucleic Acids Res.* 2015, 43 (12), 5699-5707). A configuration file was made for each SELEX experiment, outlining the selection-specific parameters such as: template length, primer sequences, and the number of selection rounds. The quality control parameters, locality sensitive hashing options, and the cluster relations settings were not changed from the program's default settings. For Library C, the lsh_sequence_similarity parameter was reduced from the default 6 to 4, as this library was expected to contain much more sequence similarity than the other selection libraries. Though the experimental design of the sequencing experiment allowed multiple selection libraries to be sequenced at once, the configuration files for each selection experiment were run individually in AptaCluster, and the data was examined using AptaGUI.

Base Distribution and Sequence Diversity

Table 5-1 shows the base distribution in each DNA pool selected for high throughput sequencing.

TABLE 5-1

Base distribution in DNA pools

| Library | DNA pool | A | T | C | G |
|---|---|---|---|---|---|
| Library A | original starting DNA pool prior to selection (round 0) | 27.4 | 30.4 | 23.4 | 18.7 |
| | DNA pool eluted with L-serine after elution with glycine and L-threonine (round 10) | 29.1 | 25.6 | 33.2 | 12.2 |
| | DNA pool eluted with L-serine after incubation in soil solution (round 11) | 29.4 | 25.8 | 32.7 | 12.0 |
| Library B | original starting DNA pool prior to selection (round 0) | 32.6 | 20.5 | 21.6 | 25.3 |
| | DNA pool eluted with L-serine after elution with glycine and L-threonine (round 4) | 32.7 | 20.5 | 21.4 | 25.4 |
| | DNA pool eluted with L-serine after incubation in soil solution (round 5) | 32.6 | 20.8 | 21.3 | 25.3 |
| Library C | original starting DNA pool prior to selection (round 0) | 27.9 | 21.5 | 16.4 | 34.2 |
| | DNA pool eluted with L-serine after elution with glycine and L-threonine (round 7) | 30.2 | 22.2 | 16.1 | 31.5 |
| | DNA pool eluted with L-serine after incubation in soil solution (round 8) | 30.5 | 22.1 | 16.9 | 30.6 |

Figure 4A:
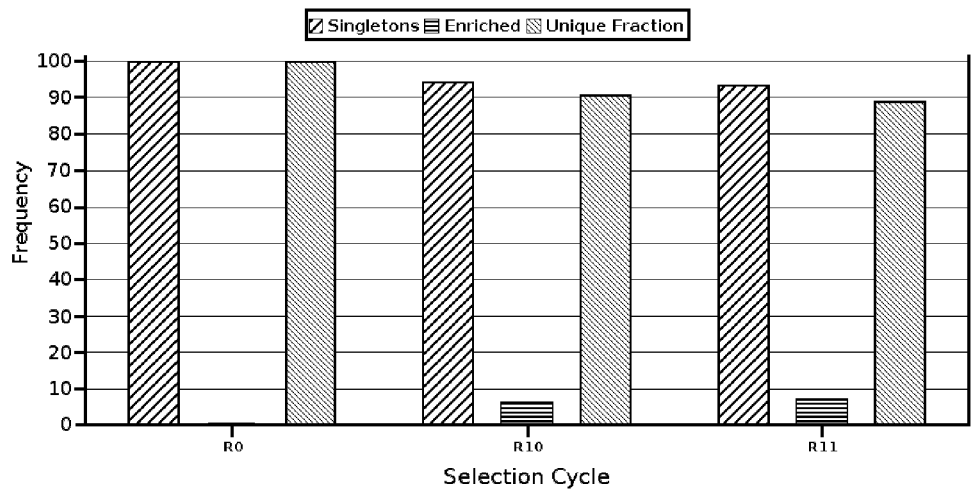
FIG. 4A is a bar graph showing the frequencies of singleton sequences (singletons) and enriched sequences (enriched), and the unique fraction at each of selection rounds 0, 10 and 11 of a SELEX (Systematic Evolution of Ligands by EXponential enrichment) procedure for a first DNA library (Library A)
Figure 4B:
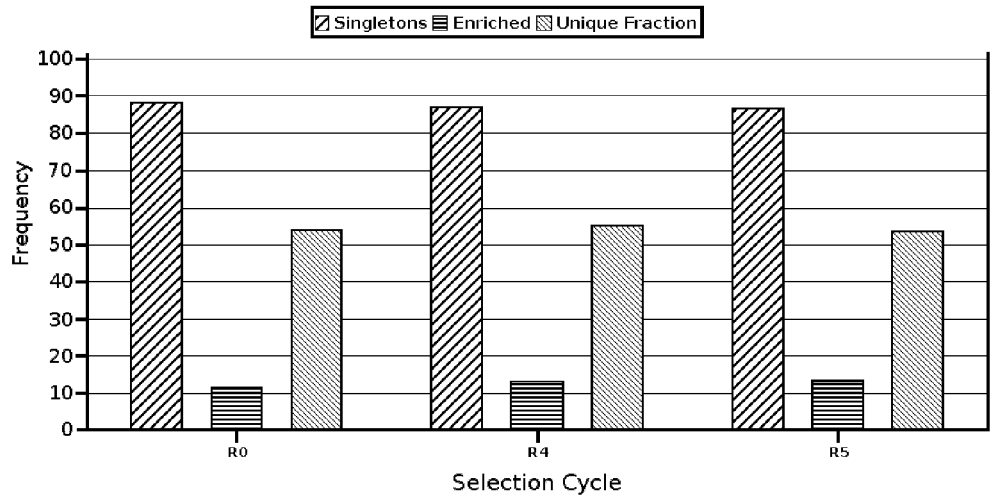
FIG. 4B is a bar graph showing the frequencies of singleton sequences (singletons) and enriched sequences (enriched), and the unique fraction at each of selection rounds 0, 4 and 5 of a SELEX procedure for a second DNA library (Library B)
Figure 4C:
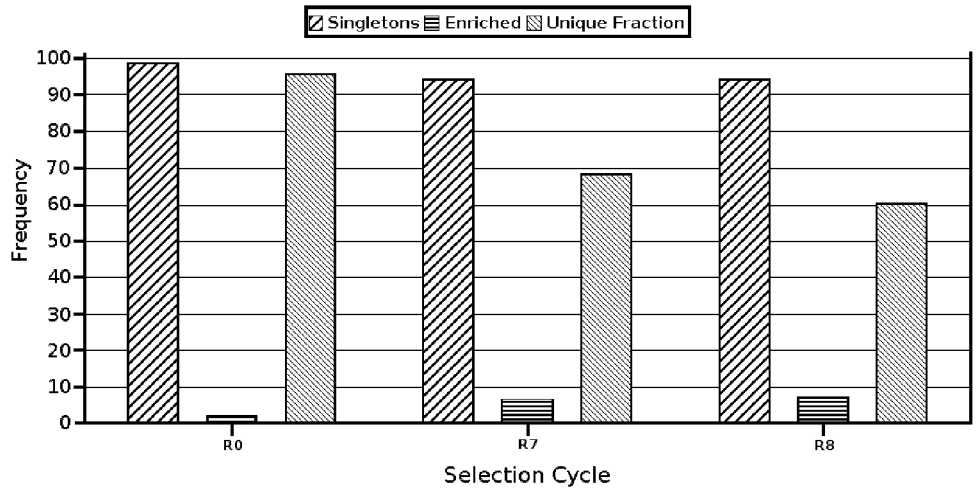
FIG. 4C is a bar graph showing the frequencies of singleton sequences (singletons) and enriched sequences (enriched), and the unique fraction at each of selection rounds 0, 7 and 8 of a SELEX procedure for a third DNA library (Library C)

FIGS. 4A-C show a comparison of the sequence diversity at various rounds of selection for Libraries A, B and C, respectively, by comparing the frequencies in percent of singleton sequences and enriched sequences, and by calculating the unique fraction for each round of selection.

As used herein, the term "unique sequence" is intended to refer to a specific polynucleotide sequence represented in a given polynucleotide pool. As used herein, the term "count" is intended to refer to the number of polynucleotide molecules in a given polynucleotide pool which have a particular unique sequence. As used herein, the term "singleton sequence" is intended to refer to a unique sequence having a count of 1 in a given pool. As used herein, the term "enriched sequence" is intended to refer to a unique sequence having a count greater than 1 in a given pool. As used herein, the term "frequency" when used in reference to a particular unique sequence is intended to refer to the number of polynucleotides having that particular unique sequence in a given pool divided by the total number of polynucleotides in that pool, multiplied by 100%. Similarly, the frequency of singleton sequences in a given pool is calculated as the number of polynucleotides having singleton sequences in the pool divided by the total number of polynucleotides in the pool, multiplied by 100%. Likewise, the frequency of enriched sequences in a given pool is calculated as the number of polynucleotides having enriched sequences in the pool divided by the total number of polynucleotides in the pool, multiplied by 100%.

Thus, for example, in a polynucleotide pool containing 10 polynucleotides, one of which has unique sequence A, one of which has unique sequence B, one of which has unique sequence C, two of which have unique sequence D and five of which have unique sequence E, there exist five unique sequences (A, B C, D and E). The pool includes three singleton sequences (A, B and C) and two enriched sequences (D and E). The frequency of each of unique sequences A, B and C is 10% (one polynucleotide having sequence A, B or C divided by ten polynucleotides×100%). Likewise, the frequency of unique sequence D is 20% (two polynucleotides having sequence D divided by ten polynucleotides×100%), and the frequency of unique sequence E is 50% (five polynucleotides having sequence E divided by ten polynucleotides×100%). The frequency of singleton sequences is 30% (three polynucleotides having singleton sequences (A, B or C) divided by ten polynucleotides× 100%) and the frequency of enriched sequences is 70% (seven polynucleotides having enriched sequences (D or E) divided by ten polynucleotides×100%).

As used herein, the term "unique fraction" is intended to refer to the number of unique sequences in a given pool divided by the total number of polynucleotides in that pool, multiplied by 100%. In the example given above, the unique fraction can be calculated as 50% (five unique sequences divided by ten polynucleotides×100%). The unique fraction in a pool can range from 100% for a more diverse or more heterogeneous polynucleotide pool, in which each polynucleotide has a different unique sequence, to a very small number that depends on pool size for a less diverse or more homogeneous polynucleotide pool, in which most or all polynucleotides have a single unique sequence. In a successful SELEX experiment, fewer unique sequences will be present in each subsequent round as the stringency of the selection increases, such that the unique fraction of the pool, and its diversity, is expected to decrease over the course of the selection. In addition, more of the polynucleotides present in the selected pool from each subsequent round will have the same selected sequence as target-binding sequences are amplified and re-selected in subsequent rounds of selection, such that the frequency of enriched sequences is expected to increase.

As seen in FIG. 4A, for Library A, the unique fraction of the starting round (R0) was 99.92%, giving a good indication that the starting library was diverse, with very few repeated sequences. After ten rounds of selection, this unique fraction decreased to 90.33%, and after the final round (R11) to 88.69%. The frequency of enriched sequences increased from nearly zero (0.08%) in the starting pool, to 7.01% in round 11. Both the decreasing unique fraction and increasing enriched portion of the SELEX pools suggested that L-serine-binding sequences were becoming enriched, while non-binding sequences were being removed from the pool. As shown in Table 5-1, in the starting pool of the original SELEX, T was slightly over-represented at 30.4%, while G was slightly under-represented at 18.7%. The frequency of G and T continued to decrease over the selection, while the frequency of A and C increased.

As seen in FIG. 4B, for Library B, the unique fraction of the starting pool (R0) was 54.00% which was the lowest diversity of the starting pools of the three libraries. This starting pool was obtained by combining DNA pools from the final two rounds of a selection against L-homocysteine, and was therefore already enriched in sequences selective for binding to L-homocysteine. Over four additional rounds of selection (R4) for L-serine, the unique fraction of the pool actually increased to 55.28% before reaching 53.80% in round 5 (R5), only slightly less diverse than the starting pool. As seen in Table 5-1, the base distribution remained largely unchanged throughout the selection. However, the enriched fraction showed a slight increase from 11.63% to 13.26% over the five selection rounds.

As seen in FIG. 4C, for Library C, the unique fraction of the starting round (R0) was 95.58% which was less diverse than the starting round (R0) of Library A. This lower diversity of the starting pool might be attributed to bias of this pool towards SEQ ID NO:5, as all the sequences were derived by randomizing nucleotides 19 to 79 inclusive of SEQ ID NO:5 by 15%. After seven rounds of selection (R7), the unique fraction decreased to 68.12%, and to 59.91% by the final round (R8). This was the largest drop in the unique fraction observed for the three libraries. As seen in Table 5-1, the base distribution did not show a large change over the 8 selection rounds. There was a slight decrease in the proportion of G, and a slight increase in the proportion of A represented in these sequences by the final round.

Identification of Aptamer Candidates

Using the software AptaCluster, DNA sequences identified in the final two rounds of selection were sorted by count and by enrichment score. As used herein, the term "enrichment score" is intended to refer to the ratio between the frequency of a particular unique sequence in a polynucleotide pool resulting from a given round of selection to the frequency of that sequence in the starting polynucleotide pool or in a polynucleotide pool resulting from a previous round of selection.

The aptamer candidates with the highest enrichment scores, rather than those with the highest count, were selected from each library to minimize possible bias due to varying efficiency of amplification of different sequences during PCR.

Aptamer A-1 is the candidate having the best enrichment score from the final round of selection of Library A (round 11) after incubation with soil solution. Aptamer A-2 is the candidate having the best enrichment score from the penultimate round of selection of Library A (round 10) after pre-elution with glycine and L-threonine.

Aptamer B-1 is the candidate having the best enrichment score from the final round of selection of Library B (round 5) after incubation with soil solution. Aptamer B-2 is the candidate having the best enrichment score from the penultimate round of selection of Library B (round 4) after pre-elution with glycine and L-threonine.

Aptamer C-1 is the candidate having the best enrichment score from the final round of selection of Library C (round 8) after incubation with soil solution. Aptamer C-2 is the candidate having the best enrichment score from the penultimate round of selection of Library C (round 7) after pre-elution with glycine and L-threonine. The count and enrichment scores of each selected candidate are shown in Table 5-2.

TABLE 5-2

Count and enrichment scores of selected aptamer candidates

| Aptamer | DNA pool | Count | Enrichment |
|---|---|---|---|
| A-1 | DNA pool eluted with L-serine after elution with glycine and L-threonine (round 10) | ND* | ND |
|  | DNA pool eluted with L-serine after incubation in soil solution (round 11) | 320 | 210 |
|  | combined DNA pools from elution with glycine and L-threonine and the subsequent wash (round 10), and from elution of the negative column (round 11) | 240 | 170 |
| A-2 | DNA pool eluted with L-serine after elution with glycine and L-threonine (round 10) | 4700 | 9600 |
|  | DNA pool eluted with L-serine after incubation in soil solution (round 11) | 8300 | 1.2 |
|  | combined DNA pools from elution with glycine and L-threonine and the subsequent wash (round 10), and from elution of the negative column (round 11) | 9100 | 1.3 |
| B-1 | DNA pool eluted with L-serine after elution with glycine and L-threonine (round 4) | 1.0 | ND |
|  | DNA pool eluted with L-serine after incubation in soil solution (round 5) | 79,000 | 67,000 |
|  | combined DNA pools from elution with glycine and L-threonine and the subsequent wash (round 4), and from elution of the negative column (round 5) | 2.0 | 1.6 |
| B-2 | DNA pool eluted with L-serine after elution with glycine and L-threonine (round 4) | 20,000 | 18,000 |
|  | DNA pool eluted with L-serine after incubation in soil solution (round 5) | 1.0 | 0 |
|  | combined DNA pools from elution with glycine and L-threonine and the subsequent wash (round 4), and from elution of the negative column (round 5) | 1.0 | 0 |
| C-1 | DNA pool eluted with L-serine after elution with glycine and L-threonine (round 7) | 2.0 | 0.18 |
|  | DNA pool eluted with L-serine after incubation in soil solution (round 8) | 630,000 | 260,000 |
|  | combined DNA pools from elution with glycine and L-threonine and the subsequent wash (round 7), and from elution of the negative column (round 8) | 83 | 24 |
| C-2 | DNA pool eluted with L-serine after elution with glycine and L-threonine (round 7) | 5200 | 3200 |
|  | DNA pool eluted with L-serine after incubation in soil solution (round 8) | 6200 | 1.0 |
|  | combined DNA pools from elution with glycine and L-threonine and the subsequent wash (round 7), and from elution of the negative column (round 8) | 4300 | 0.49 |

*ND = not detected

The sequences of these aptamer candidates are shown in Table 5-3.

TABLE 5-3

Sequences of selected aptamer candidates

| Aptamer | Sequence | Identifier |
|---|---|---|
| A-1 | AGCAGCACAGAGGTCAGATGCCTATGCGTGCTACCG TGAAACCGATCGGAAGAGCACACGCCTATGCGTGCT ACCGTGAA | SEQ ID NO: 20 |
| A-2 | AGCAGCACAGAGGTCAGATGCGATCTGGATATTATTT TTGATACCCCTTTGGGGAGACATCCTATGCGTGCTAC CGTGAA | SEQ ID NO: 21 |
| B-1 | ATACCAGCTTATTCAATTAGATAGTAAGTGCAATCTAG ATCGGAAGAGCACACGTCTGAACTCCAGTCACTTAG GCATCAGATAGTAAGTGCAATCT | SEQ ID NO: 22 |

TABLE 5-3-continued

Sequences of selected aptamer candidates

| Aptamer | Sequence | Identifier |
|---|---|---|
| B-2 | ATACCAGCTTATTCAATTGGCCGTGTAGATAGTAAGT GCAATCTGATCGGAAGAGCACACGTCTGAACTCCAG TCACCGAGATAGTAAGTGCAATCT | SEQ ID NO: 23 |
| C-1 | ATACCAGCTTATTCAATTAGATAGTAAGTGCAATCTTG ATCGGAAGAGCACACGTCTGAACTCCAGTCACTTAG GCATCAGATAGTAAGTGCAATCT | SEQ ID NO: 24 |
| C-2 | ATACCAGCTTATTCAATTGTATACGGAGTGGATATCG ATCTGTAACGTGAGTGAGATAATGTGATGCATAGTCG TGGAGAGATAGTAAGTGCAATCT | SEQ ID NO: 25 |

Identification of Common Sequence Motifs in Aptamer Candidates

Common sequence motifs were identified using a pairwise sequence alignment tool (EMBOSS Needle), available from the European Molecular Biology Laboratory—European Bioinformatics Institute (EMBL-EBI) web site at http://www.ebi.ac.uk/Tools/psa/emboss_needle/nucleotide-.html and all sequences were manually screened for common motifs. Identified common motifs containing more than 10 nucleotides (excluding forward primer binding regions located at the 5' end of each aptamer and reverse primer binding regions located at the 3' end of each aptamer) are shown in Table 5-4.

TABLE 5-4

Common long (>10 nucleotides) sequence motifs identified from selected aptamer candidates

| Sequence of motif (5' to 3') | Identifier | Aptamer (starting position within sequence) |
|---|---|---|
| CCTATGCGTGCTACCGTGAA | SEQ ID NO: 2 | A-1 (position 21) |
| AGATAGTAAGTGCAATCT | SEQ ID NO: 26 | B-1 (position 19) B-2 (position 27) C-1 (position 19) |
| GGAAGAGCACACGTCTGA ACTCCAGTCACTTAGGCA TC | SEQ ID NO: 27 | B-1 (position 42) B-2 (position 49) C-1 (position 42) |
| GGAAGAGCACACG | SEQ ID NO: 28 | A-1 (position 47) B-1 (position 42) B-2 (position 49) C-1 (position 42) |

The reverse primer binding site of Library A (5'-CCTATGCGTGCTACCGTGAA-3'; SEQ ID NO:2) was found within the central sequence of aptamer candidate A-1, immediately following the forward primer binding site, shown in Table 5-3. In addition, the reverse primer binding site from Libraries B and C (5'-AGATAGTAAGTGCAATCT-3'; SEQ ID NO:26) also appeared immediately following the forward primer binding sites in aptamer candidates B-1 and C-1, and slightly shifted towards the 3' end of the sequence of aptamer candidate B-2. It was unexpected to observe this appearance of the reverse primer binding site sequence in three separate SELEX experiments with two different sets of primers. Both primer sets were examined for their likelihood to form primer-dimers using the Multiple Primer Analyzer tool (ThermoFisher Scientific), and no primer-dimers were found. In addition, no change in library size which could indicate mis-priming was observed.

Appreciable sequence homology was observed among the aptamer candidates. The sequences of aptamers B-1 (SEQ ID NO:22) and C-1 (SEQ ID NO:24) are identical except for nucleotide 37, despite arising from different libraries. The sequence of candidate B-2 (SEQ ID NO:23) is also very similar to that of candidates B-1 and C-1, each of which contain a conserved motif of 38 nucleotides (5'-GGAAGAGCACACGTCTGAACTCCAGTCACTTAGG-CATC-3'; SEQ ID NO:27). A 13-nucleotide portion of this motif (5'-GGAAGAGCACACG-3'; SEQ ID NO:28) is also found in sequence A-1.

The percentage of unique sequences containing conserved sequence motifs in the starting library and final selection round for each library is shown in Table 5-5.

TABLE 5-5

Persistence of conserved sequence motifs during selection

| | | % of unique sequences | | |
|---|---|---|---|---|
| Library | Conserved motif | Starting library | Final selection round | Fold increase |
| A | Reverse primer-binding region CCTATGCGTGCTACCGTGAA (SEQ ID NO: 2) | 0.0021 | 0.23 | 110 |
| | Forward primer-binding region AGCAGCACAGAGGTCAGATG (SEQ ID NO: 1) | 0.000071 | 0.00014 | 2 |
| | GGAAGAGCACACG (SEQ ID NO: 28) | 0.00017 | 0.0033 | 28 |

TABLE 5-5-continued

Persistence of conserved sequence motifs during selection

| Library | Conserved motif | % of unique sequences | | Fold increase |
|---|---|---|---|---|
| | | Starting library | Final selection round | |
| B | Reverse primer-binding region AGATAGTAAGTGCAATCT (SEQ ID NO: 26) | 7.1 | 14 | 2 |
| | Forward primer-binding region ATACCAGCTTATTCAATT (SEQ ID NO: 29) | 4.3 | 9.5 | 2 |
| | GGAAGAGCACACG (SEQ ID NO: 28) | 2.1 | 3.8 | 2 |
| C | Reverse primer-binding region AGATAGTAAGTGCAATCT (SEQ ID NO: 26) | 0.025 | 1.7 | 68 |
| | Forward primer-binding region ATACCAGCTTATTCAATT (SEQ ID NO: 29) | 0.0077 | 0.68 | 88 |
| | GGAAGAGCACACG (SEQ ID NO: 28) | 0.0086 | 0.42 | 49 |

In Library A, the conserved motifs made up a very small percentage of the starting library, demonstrating the large diversity that was present in the original pool starting library. Over the course of the selection, the presence of the sequence motif corresponding to the reverse primer-binding region (SEQ ID NO:2), including in locations other than at the 3' end of the aptamer sequence, increased by 110 times. In contrast, the presence of the sequence motif corresponding to the forward primer-binding region (SEQ ID NO:1), including in locations other than at the 5' end of the aptamer sequence, only increased by 2 times by the final round. The motif 5'-GGAAGAGCACACG-3' (SEQ ID NO:28) was also shown to be 28 times more abundant by the final round. Library C also showed the persistence of this motif, as it became 49 times more abundant by the final selection round. In addition, sequence motifs corresponding to both primer-binding regions became more abundant throughout the selection.

Each of these conserved motifs was found to be very abundant in starting Library B. The reverse primer-binding site, the forward primer-binding site, and the motif 5'-GGAAGAGCACACG-3' (SEQ ID NO:28) were found in 7.1%, 4.3%, and 2.1%, respectively, of the sequences, which was at least three orders of magnitude higher than in Library A. This was indicative of lower sequence diversity for Library B, which came from the final rounds of an L-homocysteine selection, so it was likely these motifs were enriched during the L-homocysteine selection. Nevertheless, the motifs became two times more abundant by the final L-serine selection round.

Shorter (4-10 nucleotides) regions of homology between the aptamer candidates were also identified using the pairwise sequence alignment tool (EMBOSS Needle) described above. Common motifs located solely in the randomized regions of at least two of the aptamer candidate sequences are shown in Table 5-6, while common motifs located also in the primer-binding regions of at least two of the sequences are shown in Table 5-7. As noted above, reverse primer-binding sequences were found to have been repeated in aptamer candidates A-1, B-1, B-2 and C-1, and it is possible that the primer-binding sequences could be involved in L-serine-binding.

TABLE 5-6

Conserved short sequence motifs (4-10 nucleotides) located only in randomized regions of at least two aptamer candidates

| Motif | Nucleotide Position in DNA Sequence from 5' end | | | | | |
|---|---|---|---|---|---|---|
| | A-1 | A-2 | B-1 | B-2 | C-1 | C-2 |
| CGATCTG | — | 21 | — | — | — | 36 |
| CGATC | 43 | 21 | — | — | — | 36 |
| -GATC-- | — | 44 | 22 | 38 | 45 | 38 | 37 |
| -TGGATAT | — | 26 | — | — | — | 29 |
| -TGGA--- | — | 26 | — | — | — | 29, 75 |
| GGAGA | — | 53 | — | — | — | 76 |
| TGAA | 37, 77 | 77 | 57 | 64 | 57 | — |
| GAAG | 49 | — | 43 | 50 | 43 | — |
| TGAT | — | 39 | — | 44 | 37 | 62 |
| ACGT | — | — | 52 | 59 | 52 | 45 |
| CTGA | — | — | 56 | 63 | 56 | — |
| CATC | — | 58 | 76 | — | 76 | — |

TABLE 5-7

Conserved short sequence motifs (4-10 nucleotides) included in primer-binding regions of at least two aptamer candidates

| | Nucleotide Position in DNA Sequence from 5' end | | | | | |
|---|---|---|---|---|---|---|
| Motif | A-1 | A-2 | B-1 | B-2 | C-1 | C-2 |
| AGTG-- | — | — | 27, 88* | 35, 88* | 27, 88* | 27, 88* |
| AGCACA | 4*, 53 | 4* | 47 | 54 | 47 | — |
| GTGC | 28, 68* | 68* | 28, 89* | 36, 89* | 28, 89* | 89* |
| TACC | 32, 72* | 41, 72* | 2* | 2* | 2* | 2* |
| ATCT | — | 23 | 33, 94* | 41, 94* | 33, 94* | 38, 94* |
| GATA | — | 28, 40 | 20, 81* | 28, 81* | 20, 81* | 31, 55, 80* |
| TATT | — | 30 | 10* | 10* | 10* | 10* |
| CGTG | 27, 35, 67*, 75* | 67*, 75* | — | 22 | — | 46, 73 |
| GTGA | 36, 76* | 76* | — | — | — | 47, 51 |
| ACCG | 33, 41, 73* | 73* | — | 76 | — | — |

*motif present in primer-binding region

Many shorter sequence motifs were common among several aptamer candidates. Interestingly, motif GATC was identified in all aptamer candidates but was not present in the L-homocysteine-binding aptamer used as the starting sequence for generating library C (SEQ ID NO:5). This motif was thus selected during selection of each of the three libraries A, B and C, and it is possible that this motif could be implicated in L-serine binding. The 6-nucleotide motif AGCACA was present in the forward primer-binding region in Library A, and the motif was repeated within the sequence of aptamer candidate A-1 from this same selection, as well as appearing within the sequences of the aptamer candidates B-1, B-2 and C-1, which used different primers. The shorter motif GATA, found in the reverse primer-binding site of Libraries B and C, was repeated once in the sequences of the aptamer candidates B-1, B-2 and C-1, and repeated twice within the sequence of the aptamer candidate C-2. This motif also appeared twice within the sequence of the aptamer candidate A-2, which used a different set of primers. The appearance of common motifs from the primer-binding regions within aptamer candidates from each selection experiment indicated a likely interaction between the primer-binding sequences and the target L-serine.

Example 6: Serine Binding Affinity of Aptamer Candidates

Aptamer candidates were synthesized and modified with fluorescein at the 5'-end as described in Example 2. The fluorescein-modified aptamers were purified by PAGE as described in Example 2 and the structures confirmed by electrospray ionization liquid chromatography/mass spectrometry (ESI/LC/MS).

Binding to L-Serine Immobilized on Sepharose™ Beads

Figure 5:
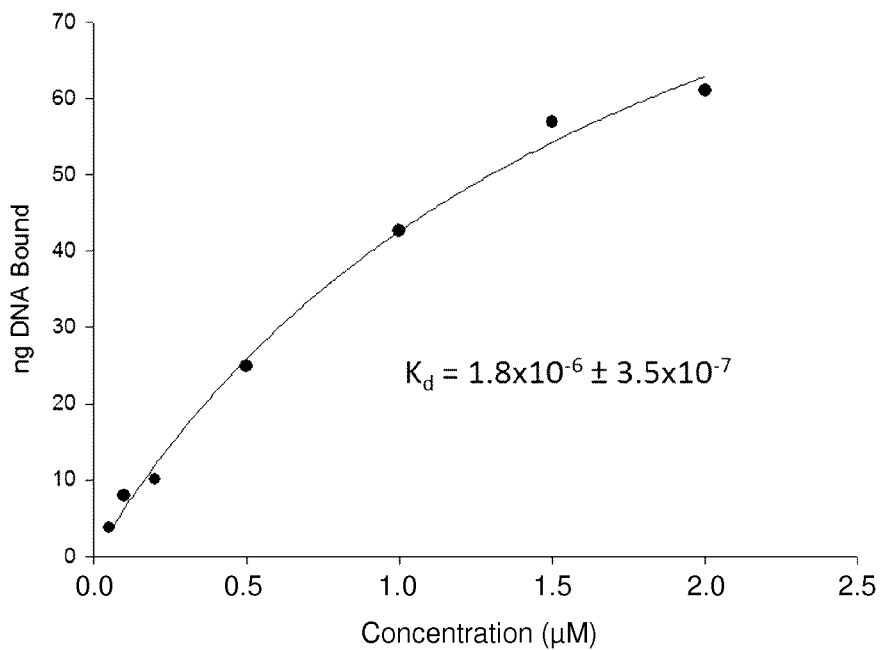
FIG. 5 is a graph of the amount of aptamer candidate B-1 bound to L-serine conjugated to Sepharose™ beads versus the concentration of candidate B-1.

Aptamer candidates were diluted in phosphate buffered saline (PBS) buffer over a range of concentrations (2 μM-50 nM, for example). L-serine-coupled beads prepared as described in Example 3 were diluted 1:1 in PBS buffer, and 20 μL of the bead slurry was added to 0.22 μm Costar™ Spin-X™ cellulose acetate centrifuge filters (Corning Incorporated), for each aptamer concentration to be tested. The beads were washed by adding 100 μL of PBS buffer, and centrifuging at 13000×g. The DNA was heated at 90° C. for 5 minutes, cooled at 4° C. for 10 minutes, and left at room temperature for 15 minutes. 100 μL of each DNA concentration were added to L-serine-coupled beads, and placed on a shaker at room temperature for 45 minutes. Unbound DNA was removed by centrifuging at 5000×g for 1 minute, followed by 3 washes using 100 μL of PBS buffer each. For elution of bound DNA, 100 μL of 7 M urea was added to the beads, and the mixture was vortexed, and incubated at 90° C. for 10 minutes. The eluate was collected after centrifugation at 13000×g for 1 minute. This was repeated for 3 elutions per test concentration. The fluorescence intensity of the elutions was measured using a Fluorolog™ Fluorescence Spectrophotometer (Horiba Jobin Yvon, USA) with an excitation wavelength of 490 nm, emission wavelength of 520 nm, and slit widths 5 nm. The amount of DNA eluted at each concentration was calculated by comparing to a standard curve of fluorescence intensity at known concentrations. A representative binding isotherm for aptamer candidate B-1 is shown in FIG. 5 and the apparent $K_d$ values for each aptamer candidate for Sepharose™ beads conjugated to L-serine, Tris or L-glycine are shown in Table 6-1. SigmaPlot simple ligand binding was used to calculate $K_d$ values, and the error represents the standard deviation between trials (N=3).

TABLE 6-1

Apparent $K_d$ values for binding of aptamer candidates to L-serine, Tris, or L-glycine immobilized on Sepharose ™ beads

| | Apparent $K_d$ (μM) | | |
|---|---|---|---|
| Aptamer | L-Serine | Tris | L-Glycine |
| A-1 | 3.0 ± 2.7 | 0.85 ± 0.68 | 2.3 ± 0.13 |
| A-2 | ND* | 2.0 ± 1.0 | 4.7 ± 5.9 |
| B-1 | 2.8 ± 2.0 | 4.0 ± 2.7 | 2.6 ± 1.3 |
| B-2 | 3.5 ± 2.9 | 0.72 ± 0.057 | ND |

TABLE 6-1-continued

Apparent $K_d$ values for binding of aptamer candidates to
L-serine, Tris, or L-glycine immobilized on Sepharose™ beads

| Aptamer | Apparent $K_d$ (μM) | | |
|---|---|---|---|
| | L-Serine | Tris | L-Glycine |
| C-1 | ND | ND | ND |
| C-2 | 2.9 ± 3.2 | ND | NB** |

*ND indicates a possible $K_d$ value outside the range of the concentrations tested or possible non-specific binding to sepharose.
**NB indicates no binding trend is observed.

As seen in Table 6-1, all aptamer candidates showed binding to immobilized L-serine in the low micromolar range, except for A-2 and C-1 which showed binding to L-serine but had an apparent $K_d$ outside the range of test concentrations. Candidate B-1 showed the highest affinity for immobilized L-serine with an apparent $K_d$ of 2.8±2.0 μM. Despite attempts to counter select against Tris by exposing the DNA pools to Sepharose™-immobilized Tris prior to every selection round, some affinity for Tris remained, and all of the aptamer candidates showed binding to Tris ranging from 0.85 to 4.0 μM, except C-1 and C-2 which showed weak binding outside the range of tested concentrations. Aptamers A-1, A-2, and B-1 showed affinity for L-glycine with apparent $K_d$ values ranging from 2.3 to 4.7 μM, while C-1 and B-2 showed weak binding outside the range of tested concentrations. C-2 was the most selective of all the aptamer candidates, showing no binding to L-glycine, and the weakest binding to Tris of all the aptamer candidates. As a control, a random 81-nucleotide aptamer selected for binding to an unrelated target showed minimal binding to Sepharose™ beads conjugated to L-serine when compared to aptamer candidate C-2, indicating that binding of aptamer candidate C-2 is specific for L-serine.

Binding to L-Serine in Solution Using Microscale Thermophoresis (MST)

Microscale thermophoresis analysis was carried out by 2bind GmbH (Regensburg, Germany) on 10 μL samples of aptamers labeled with Cy5 at the 5' end in solution (10 μM in PBS buffer) and 1 mL samples of L-serine solution (10 mM in PBS buffer). A range of L-serine concentrations (7.6 nM-250 μM in PBS buffer) was incubated with 20 nM of labeled aptamer and analyzed on a Monolith™ NT system at 25° C., with 15% LED power and 80% laser power.

Figure 6A:
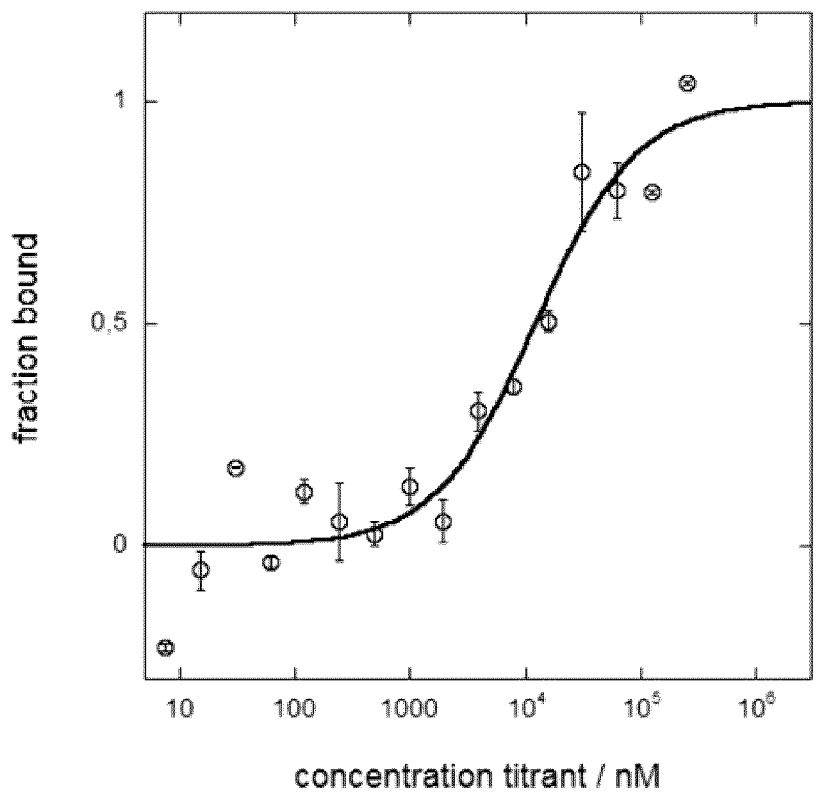
FIG. 6A is a graph showing the fraction of L-serine bound to aptamer candidate A-1 as measured by microscale thermophoresis versus the concentration of L-serine.
Figure 6B:
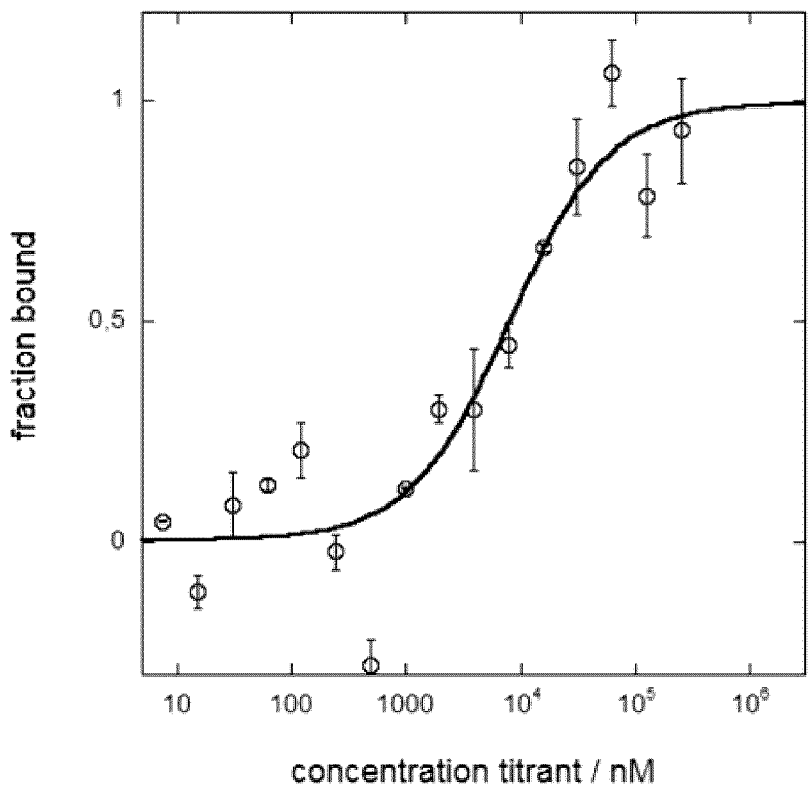
FIG. 6B is a graph showing the fraction of L-serine bound to aptamer candidate B-1 as measured by microscale thermophoresis versus the concentration of L-serine.
Figure 6C:
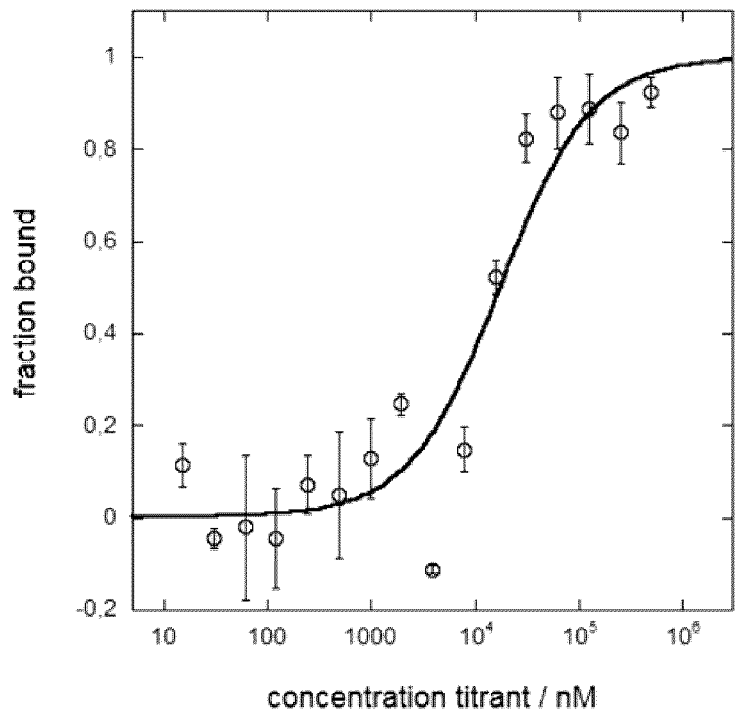
FIG. 6C is a graph showing the fraction of L-serine bound to aptamer candidate C-2 as measured by microscale thermophoresis versus the concentration of L-serine.
Figure 7A:
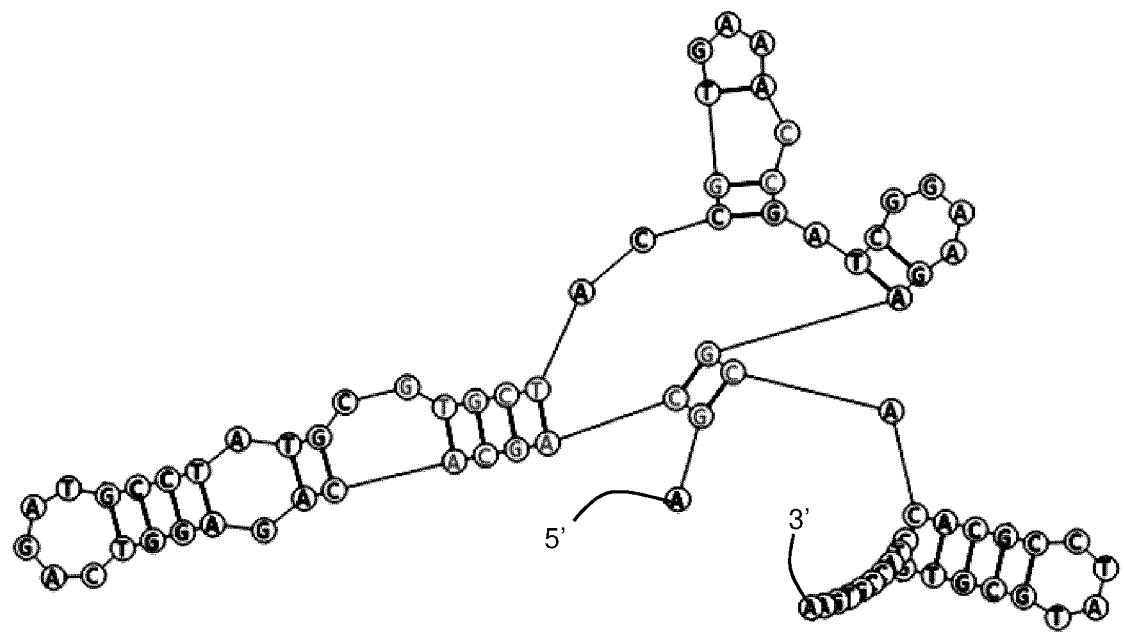
FIG. 7A is a diagrammatic illustration of a predicted structure of aptamer candidate A-1, determined using RNAstructure software.
Figure 7B:
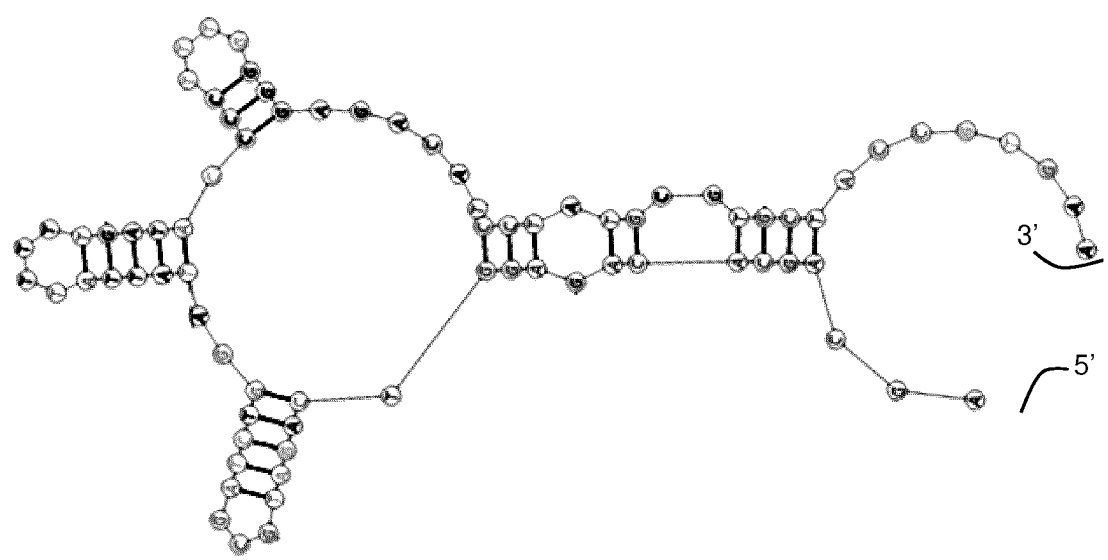
FIG. 7B is a diagrammatic illustration of a predicted structure of aptamer candidate A-2, determined using RNAstructure software.
Figure 7C:
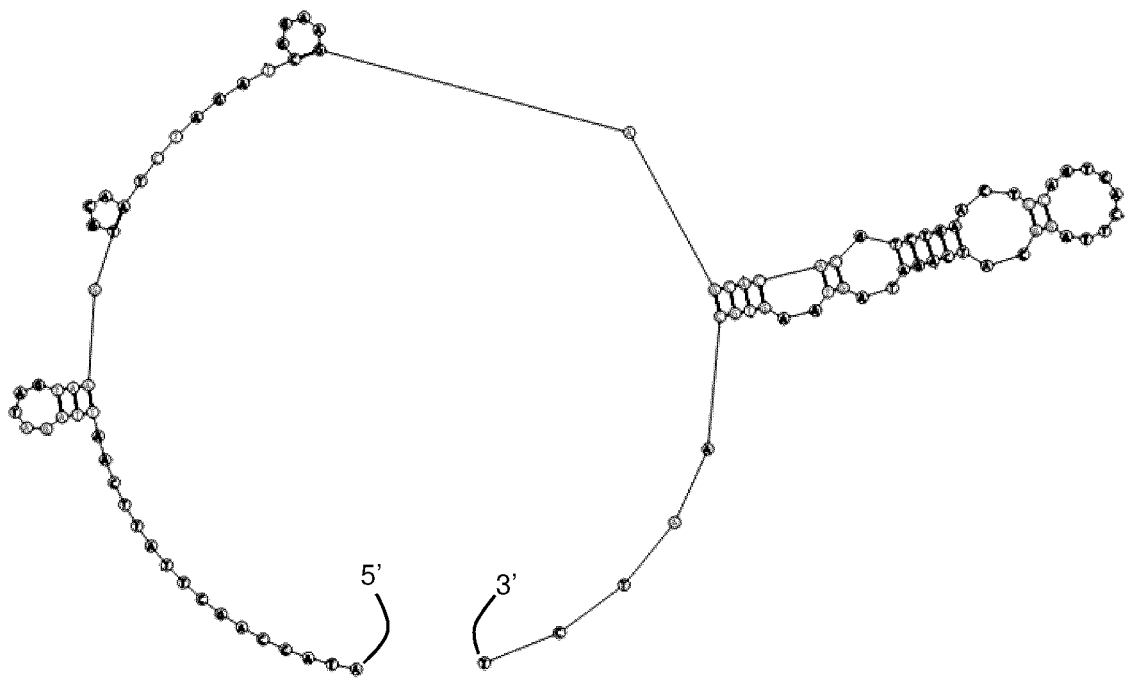
FIG. 7C is a diagrammatic illustration of a predicted structure of aptamer candidate B-1, determined using RNAstructure software.
Figure 7D:
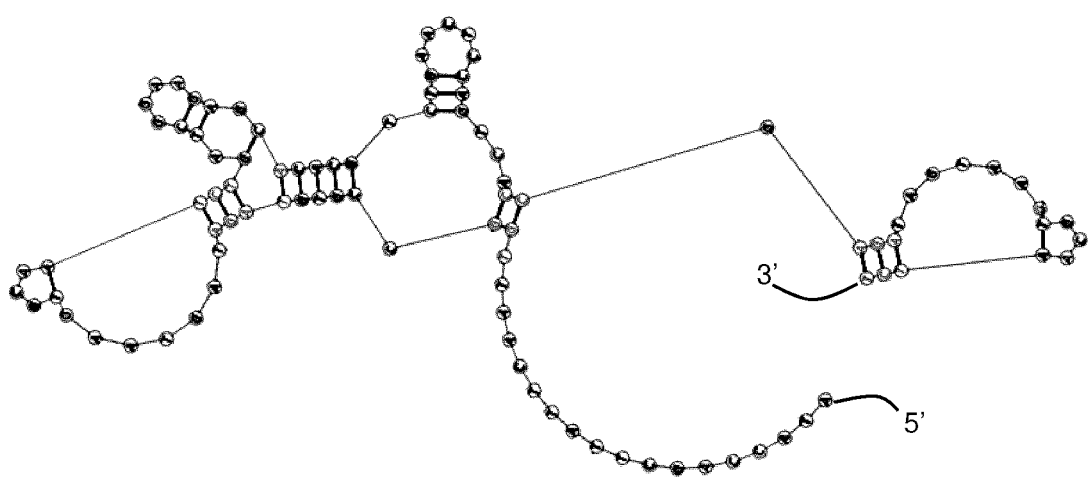
FIG. 7D is a diagrammatic illustration of a predicted structure of aptamer candidate B-2, determined using RNAstructure software.
Figure 7E:
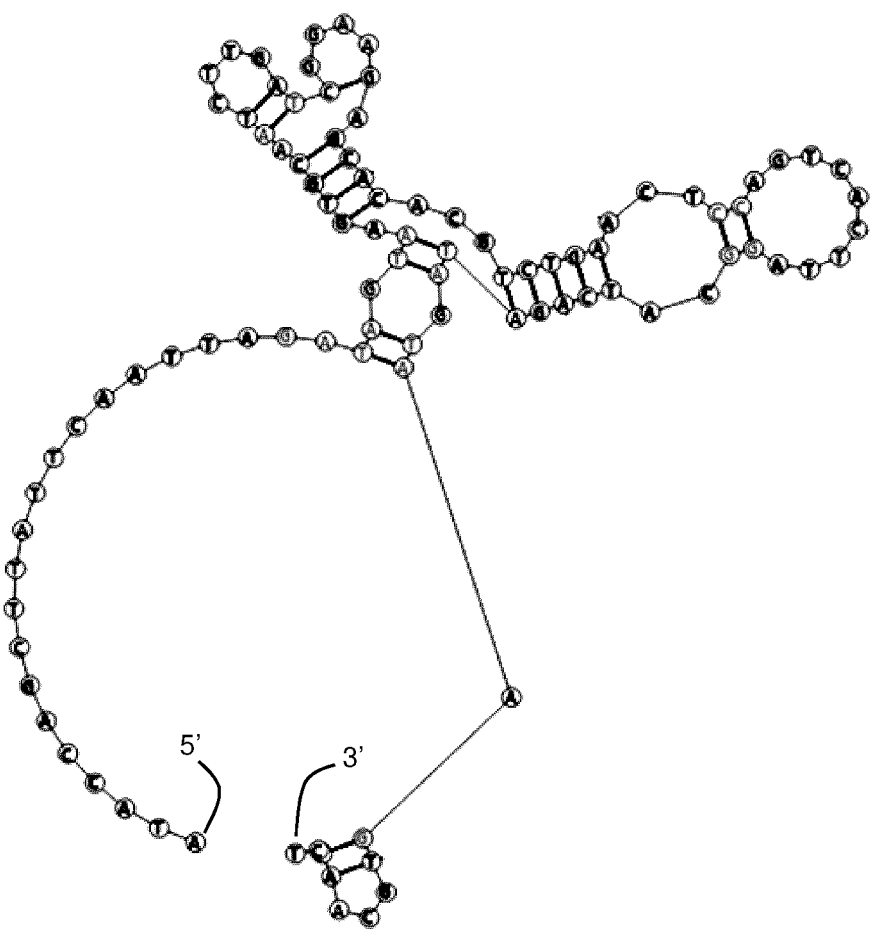
FIG. 7E is a diagrammatic illustration of a predicted structure of aptamer candidate C-1, determined using RNAstructure software.
Figure 7F:
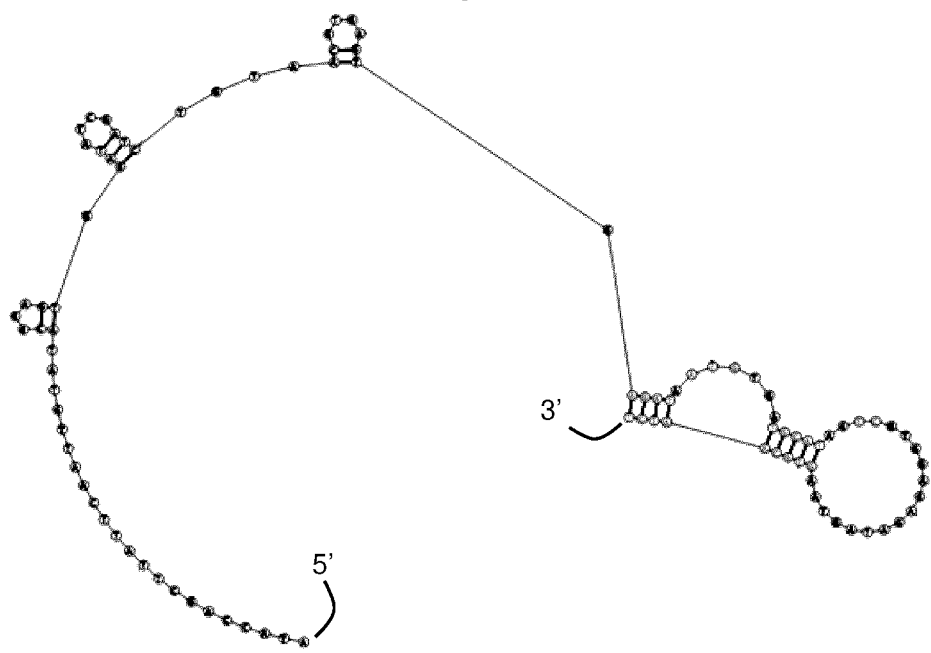
FIG. 7F is a diagrammatic illustration of a predicted structure of aptamer candidate C-2, determined using RNAstructure software.

As seen FIGS. 6A-C, aptamer candidates A-1, B-1 and C-2 showed binding to L-serine in solution, with $K_d$ values of 14.9±5.9 μM, 7.9±3.6 μM and 17.2±7.3 μM, respectively. In contrast, aptamer candidates A-2, B-2 and C-1 showed no binding to L-serine in solution.

Example 7: Computational Structural Analysis

The predicted structure of each aptamer candidate was determined using the RNAstructure software (Reuter, J. S.; Mathews, D. H. BMC Bioinformatics 2010, 11(1), 129), using the default settings. The predicted structures of the aptamer candidates included stem-loop secondary structures as shown in FIGS. 7A-F. Such stem-loop secondary structures have been found to be implicated in binding to target molecules.

In addition, to identify possible G-quadruplex-forming domains, the aptamer sequences were examined using QGRS Mapper software (Ramapo College), and the the aptamer candidates were studied using variable-temperature UV-visible spectroscopy, to measure any hypochromicity at 295 nm, which could be indicative of the presence of a G-quartet chromophore. However, no evidence of G-quadruplex domains was found in any of the aptamer candidates.

Example 8: Design and Preparation of Additional Aptamer Candidates

Preparation and Characterization of Minimers

Minimers (smaller sequences representing predicted secondary sub-structures) of the B-1 aptamer candidate were designed from the aptamer B-1 full length sequence (SEQ ID NO:22) by selecting portions of the sequence predicted to have smaller secondary structures by computational analysis. The selected minimer sequences and the corresponding portions of the aptamer B-1 sequence (SEQ ID NO:22) are shown in Table 8-1. DNA polynucleotides comprising each minimer sequence were synthesized and purified by PAGE as described in Example 2, and their structure was confirmed by mass spectrometry. Analysis of each polynucleotide was carried out by microscale thermophoresis as described in Example 6.

TABLE 8-1

Sequences of minimers

| Aptamer | Sequence | Positions in aptamer B-1 sequence | Identifier |
|---|---|---|---|
| B-1A | ATACCAGCTTATTCAATTAGATAGTAA GTGCAATCTAGATCGGAAGA | 1 to 47 | SEQ ID NO: 30 |
| B-1B | GCACACGTCTGAACTCCAGTCACTTA GGCATCAGATAGTAAGTGCAATCT | 48 to 97 | SEQ ID NO: 31 |
| B-1C | AGATAGTAAGTGCAATCTAGATCGGAA GAGCACACGTCTGAACTCCAGTCACT TAGGCATC | 19 to 79 | SEQ ID NO: 32 |
| B-1D | ATACCAGCTTATTCAATTAGATAGTAA GTGCAATCTAGATCGGAAGAGCACAC GTCTGAACTCCAGTCACTTAGGCATC | 1 to 79 | SEQ ID NO: 33 |

Binding of minimers B-1A, B-1B, B-1C and B-1D to L-serine was measured by microscale thermophoresis as described in Example 6, except that the concentration of each minimer was 5 nM and the concentration of L-serine in PBS ranged from 15 nM to 500 μM in PBS buffer. The apparent $K_d$ value for minimer B-1A was determined to be 9.6±4.4 µM and the apparent $K_d$ value for minimer B-1C was determined to be 5.2±2.8 µM. Minimers B-1B and B-1D showed no detectable binding to L-serine under these conditions. In comparison, as noted in Example 6 above, the apparent $K_d$ value for aptamer candidate B-1 was found to be 7.9±3.6 µM.

Figure 8B:
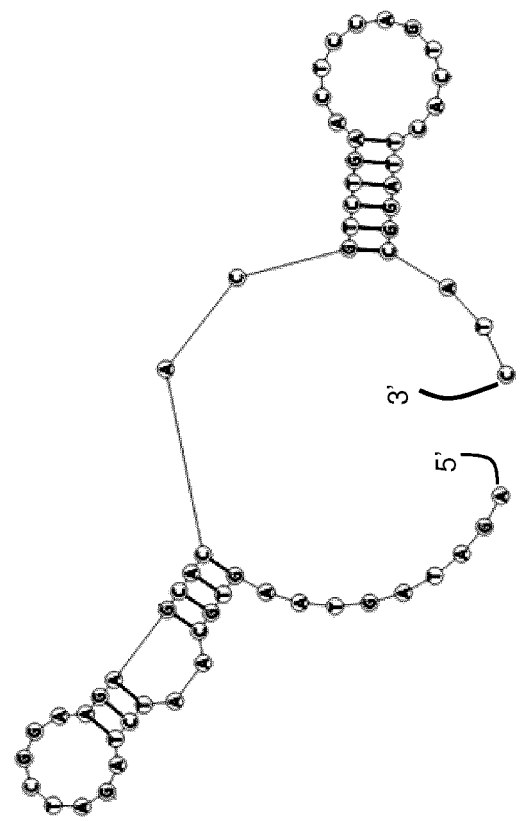
FIG. 8B is a diagrammatic illustration of a predicted structure of minimer B-1C, determined by comparison to the predicted structure of FIG. 8A for aptamer candidate B-1, using RNAstructure software.
Figure 8A:
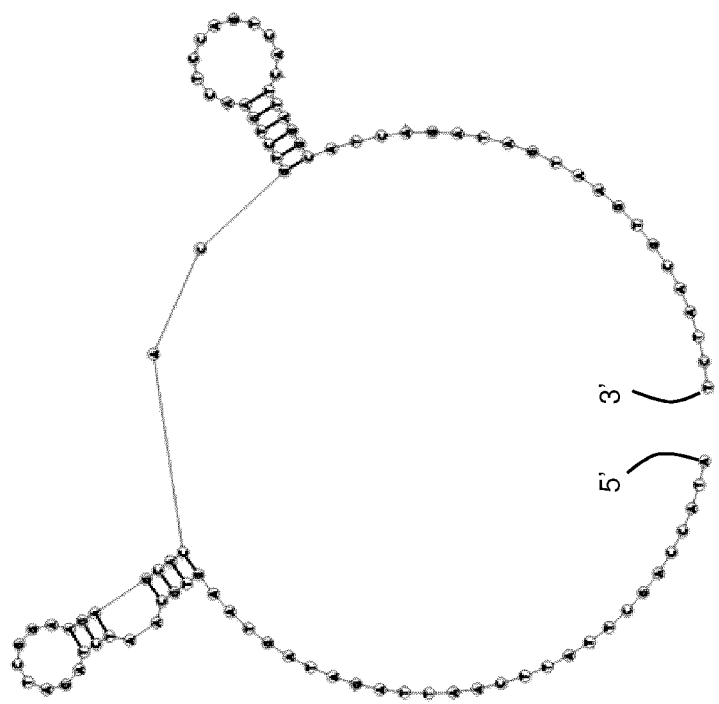
FIG. 8A is a diagrammatic illustration of a second predicted structure of aptamer candidate B-1, determined by comparison to a predicted structure for minimer B-1C, using RNAstructure software.

Because minimer B-1C and aptamer candidate B-1 both showed strong binding to L-serine in solution, further computational analysis was carried out using the RNAstructure software described in Example 7 to predict secondary structural features which might be shared by these aptamers. The predicted structures are seen in FIGS. 8A (aptamer candidate B-1) and 8B (minimer B-1C).

It is notable that minimer B-1C and aptamer candidate B-1 share a number of sequence motifs which are conserved with other aptamers found to bind L-serine, and that these conserved sequence motifs are found at least partially in the stem loop structure closest to the 5' end of both polynucleotides, which spans positions 10 to 33 of minimer B-1C and positions 28 to 51 of aptamer candidate B-1. Conserved sequence motif 5'-GATC-3' is found starting at positions 20 to 23 of minimer B-1C and at positions 38 to 41 of aptamer candidate B-1 and is located at the outer tip of the stem loop structure. Conserved sequence motif 5'-AGA-TAGTAAGTGCAATCT-3' (SEQ ID NO:26) is found at positions 1 to 18 of minimer B-1C and at positions 19 to 36 of aptamer candidate B-1. Conserved sequence motif 5'-GGAAGAGCACACG-3' (SEQ ID NO:28) is found at positions 24 to 36 of minimer B-1C and at positions 42 to 54 of aptamer candidate B-1.

Preparation and Characterization of a Spiegelmer

Spiegelmers are polynucleotides prepared from L-deoxyribonucleotides rather than the natural D-deoxyribonucleotides. A spiegelmer (designated B-1CL) based on the sequence of the minimer B-1C (SEQ ID NO:32) was prepared having the sequence AGATAGTAAGTGCAATCTA-GATCGGAAGAGCACACGTCTGAACTCCAGTCACT-TAGGCAT C (SEQ ID NO:34), in which the 5' nucleoside is labeled with the fluorescent dye Cy5. Beta-L-deoxy Adenosine (n-bz) 2-cyanoethyl-N,N-diisopropylamino (CED) phosphoramidite, Beta-L-deoxy Cytidine (n-acetyl) CED phosphoramidite, Beta-L-deoxy Guanosine (n-ibu) CED phosphoramidite, Beta-L-Thymidine CED phosphoramidite, as well as beta-L deoxy Cytidine (N—Ac) 3'-lcaa CPG (long chain alkylamine controlled pore glass) 1000A support columns, were obtained from ChemGenes. DNA synthesis and purification by PAGE was carried out as described in Example 2, and the structure was confirmed by mass spectroscopy.

Binding of spiegelmer B-1CL to L-serine was measured by microscale thermophoresis as described in Example 6, except that the concentration of L-serine in PBS ranged from 15 nM to 500 µM in PBS buffer. The apparent $K_d$ value for spiegelmer B-1CL was determined to be 2.0±0.8 µM.

Determination of Nuclease Resistance

Figures 9A, 9B:
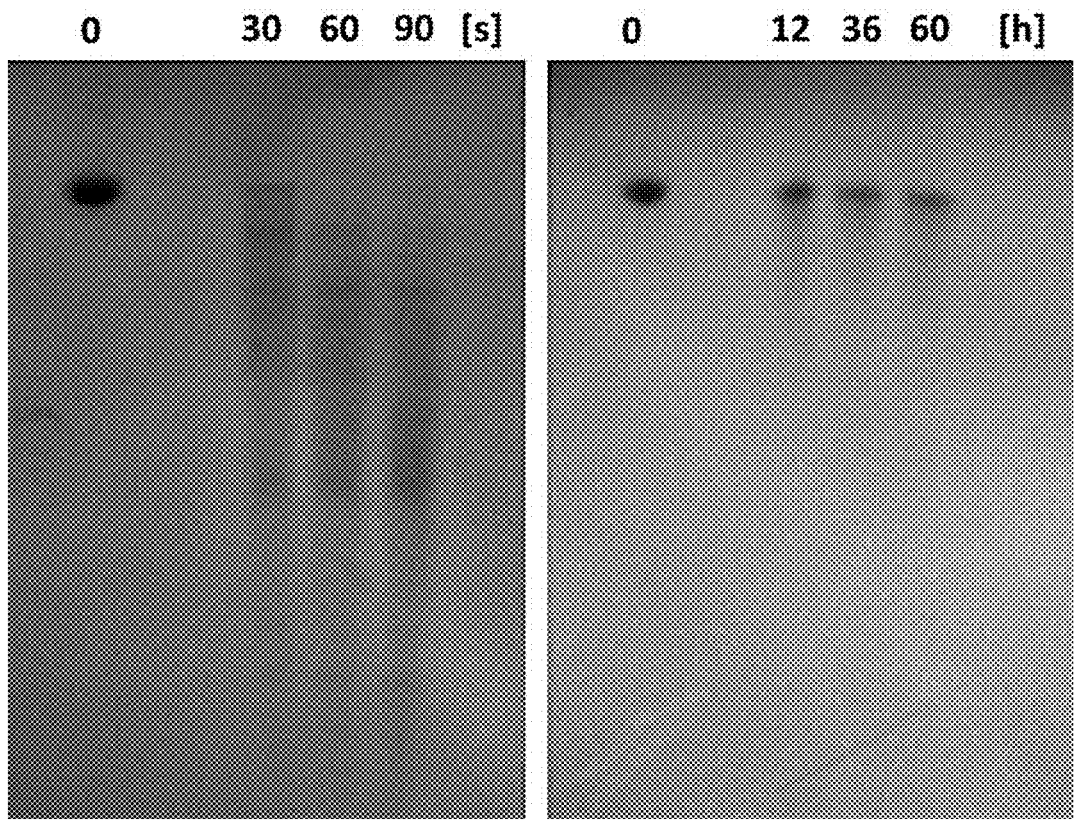
FIG. 9A is a photograph of a gel showing an analysis by denaturing polyacrylamide gel electrophoresis (PAGE) of exposure of minimer B-1C to DNAse I over a period of 90 seconds.
FIG. 9B is a photograph of a gel showing an analysis by denaturing PAGE of exposure of spiegelmer B-1CL to DNAse I over a period of 60 hours.

Minimer B-1C and spiegelmer B-1CL were each diluted to 50 µM in deionized water. 10 µL of each solution was mixed separately with 90 µL of DNase I reaction buffer (10 mM Tris-HCl, 2.5 mM $MgCl_2$, 0.5 mM $CaCl_2$, pH 7.0) for each time point to be tested. To each DNA solution, 1 µL of DNase I was added, and the tubes were incubated at 37° C. For minimer B-1C, the DNase I was incubated with the DNA for 0, 30, 60, and 90 seconds. For spiegelmer B-1CL, the DNase I was incubated with the DNA for 0, 12, 36, and 60 hours. The reaction was stopped by adding 1 µL 0.5 M EDTA and incubating tubes at 90° C. for 10 minutes. The reactions were then analyzed using denaturing PAGE as described in Example 2, except that a 19% gel was used instead of 12%, and run ~300 volts for 2.5 hours. The results show that the minimer B-1C (FIG. 9A) was degraded completely after exposure to DNAse I for 1 minute, while the spiegelmer B-1CL (FIG. 9B) showed little degradation after exposure to DNAse I for 60 hours.

Example 9: Colorimetric Test for Binding of Aptamer Candidates to L-Serine

A solution of dispersed gold nanoparticles appears wine red in colour, while a solution of gold nanoparticles which have aggregated (for example, in the presence of NaCl) appears blue. Single-stranded DNA polynucleotides, such as aptamers, can adsorb onto the surface of the gold nanoparticles, protecting them from salt-induced aggregation.

This observation has led to development of a colorimetric test for binding of the present aptamer candidates to their target binding partner L-serine. Gold nanoparticles are added to a mixture of L-serine (at a variety of test concentrations) and an aptamer candidate as described herein, followed by addition of salt. If the concentration of L-serine is too low to bind completely with the aptamer candidate, the aptamer will adsorb on the surface of the gold nanoparticles, and addition of salt will cause no aggregation of the nanoparticles. In contrast, if the concentration of L-serine is high enough that the aptamer candidate has bound completely, the aptamer candidate will not adsorb on the surface of the gold nanoparticles, and addition of salt will cause aggregation of the gold nanoparticles, as evidenced by a colour change. The concentration of the L-serine target molecule required to prevent aptamer binding to the gold nanoparticles and allow salt-induced aggregation can indicate the strength of binding between L-serine and the aptamer candidate.

Synthesis of Gold Nanoparticles

All glassware was washed with aqua regia (3:1 mixture of $HCl/HNO_3$) for 15 minutes, and thoroughly rinsed with deionized water. A 100 mL solution of 1 mM $HAuCl_4$ in deionized water was stirred and heated until boiling, and a 10 mL solution of 38.8 mM sodium citrate was quickly added. The suspension changed in colour from pale yellow to dark blue, finally reaching a wine red colour. This solution was cooled to room temperature, and the presence of gold nanoparticles was confirmed by transmission electron microscopy (TEM).

Detection of Aptamer Binding to L-Serine

As a representative procedure, 3 µL of a solution (10 µM in deionized water) of aptamer candidate B-1 (Example 5) is added to 243 µL of a L-serine solution having one of a range of test concentrations, and the mixture is incubated for 30 minutes at room temperature. After incubation, 135 µL of a 12 nM solution of gold nanoparticles prepared as described above is added, and the mixture is incubated for an additional 30 minutes. 72 µL of 0.75M NaCl solution is added, and a colour change can be observed by eye after 5 minutes. It was found that, at a serine concentration of 53 mM, salt-induced aggregation of gold nanoparticles was observed, as evidenced by a colour change from red to blue.

In an alternative representative procedure, 3 µL of a solution (10 µM in deionized water) of aptamer candidate B-1 (Example 7) is added to 243 µL of a L-serine solution having one of a range of test concentrations, and the mixture is incubated for 45 minutes. After incubation, 135 µL of a 12 nM solution of gold nanoparticles prepared as described above is added, and the mixture is incubated for an additional 30 minutes. 72 μL of a 0.5M NaCl solution is added, and incubation is continued until a colour change is observed by eye (1 week). It was found that, at a serine concentration of 546 μM, salt-induced aggregation of gold nanoparticles was observed, as evidenced by a colour change from red to blue.

Example 10: Preparation and Characterization of Coated Fertilizer Particles

Characterization of Ethyl Cellulose by Inverse Gas Chromatography

Inverse gas chromatography (IGC) was used to measure the solubility, diffusivity and permeability (the product of solubility and diffusivity) of water vapour in ethyl cellulose, as described in Bayati et al, *ACS Sustainable Chemistry & Engineering* (2014), 2(5), 1305-1311; Bayati et al, *ACS Sustainable Chemistry & Engineering* (2015) 3(12), 3114-3122 and Bayati et al, *ACS Sustainable Chemistry & Engineering* (2016) 4(5), 2578-2583. The results are shown in Table 10-1:

TABLE 10-1

Properties of ethyl cellulose measured by IGC

| Temperature (° C.) | $w_p/w_g$ | Diffusivity ($10^{-9}$ cm$^2$/s) | Solubility (cm$^3$[STP]/ cm$^3$ · atm) | Permeability ($10^{-8}$ cm$^3$[STP]/ cm · atm · s) |
|---|---|---|---|---|
| 140 | 0.005 | 0.36 ± 0.044 | 45.5 ± 3.43 | 1.65 |
|  | 0.015 | 3.2 ± 0.04 | 15.18 ± 1.14 | 4.9 |
| 150 | 0.005 | 0.42 ± 0.19 | 32.5 ± 3.2 | 1.35 |
|  | 0.015 | 3.75 ± 0.17 | 10.8 ± 1.1 | 4.07 | where $w_g/w_g$ is the ratio of the weight of the polymer (ethyl cellulose) to the weight of the glass beads on which the polymer is coated.

Extrapolation of the results in Table 10-1 to ambient temperature indicate that the values of permeability of water vapour through ethyl cellulose are in the desired range of $10^{-9}$-$10^{-10}$ cm$^3$ [STP]/cm·atm·s, as described in Bayati et al, *ACS Sustainable Chemistry & Engineering* (2016) 4(5), 2578-2583, such that ethyl cellulose is suitable for a coating as described herein. Other suitable polymers can be identified and selected by the skilled person using this or similar techniques, or otherwise in view of this teaching.

Coating of Fertilizer Particles

A coating mixture containing ethyl cellulose (1% by weight) and palmitic acid (0.1% or 0.5% by weight) in butanol is introduced into the atomizing injector of a coating apparatus as described herein. Pellets of commercial urea fertilizer (synAgri) are coated with the coating mixture using a coating apparatus as diagrammatically shown in FIG. 13.

Figure 10A:
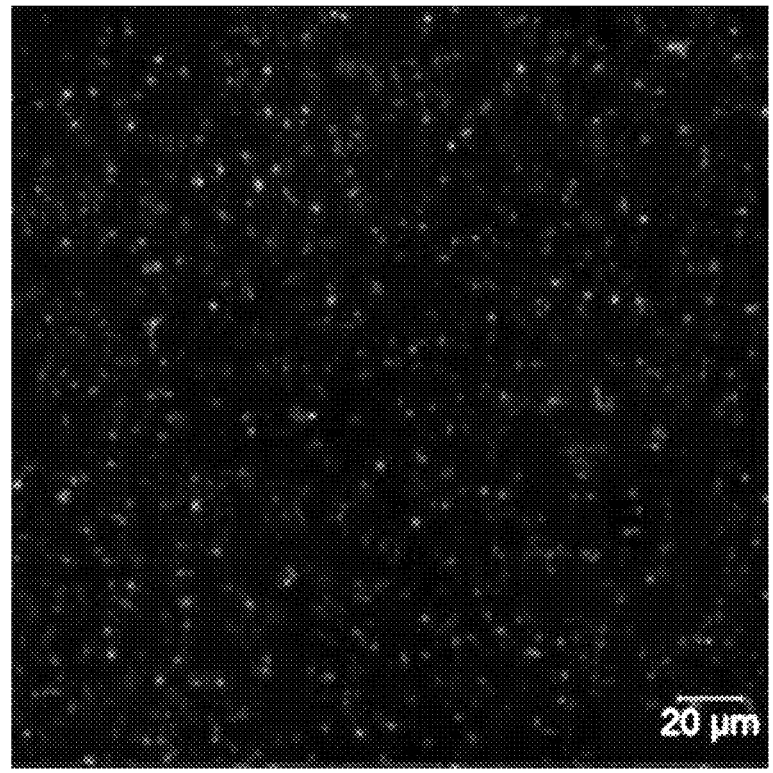
FIG. 10A is a fluorescence microscopy image of an embodiment of the present coating, showing the location of fluorescence (red) due to the fluorescent dye sulforhodamine B which binds non-covalently to an aptamer specific to sulforhodamine B.
Figure 10B:
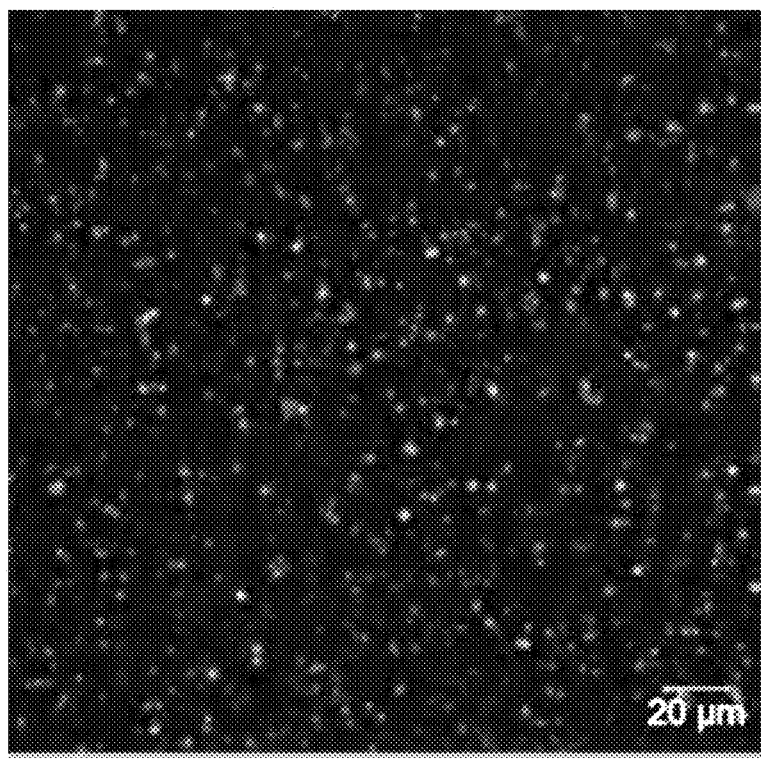
FIG. 10B is a fluorescence microscopy image of an embodiment of the present coating, showing the location of fluorescence (green) due to a 6-carboxyfluorescein fluorescent tag covalently bound to the aptamer of FIG. 10A.
Figure 10C:
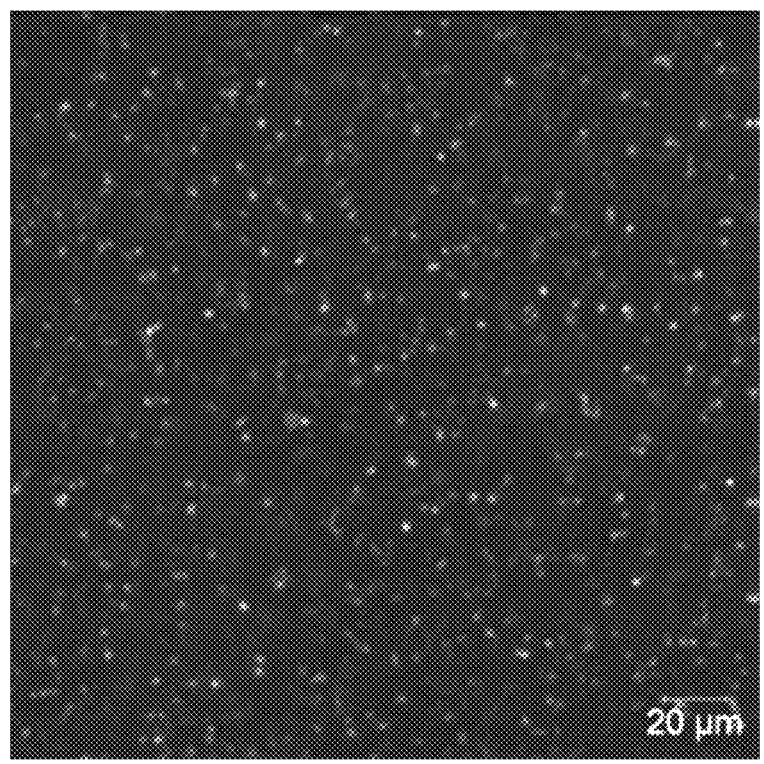
FIG. 10C is a fluorescence microscopy image of an embodiment of the present coating, showing the location of fluorescence when the fluorescence microscopy images of FIG. 10A and FIG. 10B are superimposed. Yellow fluorescence indicates where the red fluorescent portions of FIG. 10A coincide with the green fluorescent portions of FIG. 10B.

FIGS. 10A-C are fluorescence microscopy images of a coating prepared as described above containing an aptamer specific for sulforhodamine B comprising a 6-carboxyfluorescein fluorescent tag and exposed to sulforhodamine B. FIG. 10A shows the location of fluorescence due to the sulforhodamine B target (red), FIG. 10B shows the location of fluorescence due to the fluorescently tagged aptamer (green) and FIG. 10C shows the co-localization of both the fluorescence due to the target and the fluorescence due to the aptamer (yellow). As can be seen from FIGS. 10A-C, the aptamer is evenly distributed throughout the coating, and selectively binds to the target, as evidenced by the co-localization of fluorescence from the target and the aptamer.

Example 11: Application of Coated Fertilizer Particles to Canola Plants

Canola plants (*Brassica napus*) were grown from seed as described in Example 1. Various treatments as shown below were applied to the plants. Fertilizers were applied at the time of seeding in an amount equivalent to 100 kg N/ha.

A Urea fertilizer (synAgri) coated with an embodiment of the present coating containing ethyl cellulose: palmitic acid (1:0.1 by weight);

B Urea fertilizer (synAgri) coated with an embodiment of the present coating containing ethyl cellulose: palmitic acid (1:0.5 by weight);

C Urea fertilizer (synAgri) coated with palmitic acid;

D Uncoated urea fertilizer (synAgri);

E ESN™ Environmental Smart Nitrogen fertilizer (Agrium);

F No fertilizer (soil planted with canola);

G Urea fertilizer (synAgri) coated with an embodiment of the present coating containing ethyl cellulose: palmitic acid (1:0.1 by weight) and a short random strand of DNA;

H Urea fertilizer (synAgri) coated with an embodiment of the present coating containing ethyl cellulose: palmitic acid (1:0.5 by weight) and a short random strand of DNA;

I Urea fertilizer (synAgri) coated with palmitic acid and a short random strand of DNA; and J No fertilizer (soil alone, not planted).

The plants were watered once per week with a total of six 250 mL portions of water (a total of 1500 mL of water over 53 days of growth) to simulate rainfall events. As a control, canola was grown with no added nitrogen source, but with addition of phosphorus-potassium-sulfur (PKS) and micronutrient supplements.

Biomass Productivity and Nitrogen Use Efficiency

Biomass productivity is calculated as:

$$\text{Biomass productivity (g/mg)} = \frac{(\text{biomass in treatment (g)} - \text{biomass in control (g)})}{\text{mass of nitrogen added from urea (mg)}}$$

Biomass is measured as the mass of the entire plant from which soil has been removed and which was oven dried at 60° C.

Nitrogen use efficiency (NUE) is calculated as:

$$NUE\ (\%) = \frac{(\text{nitrogen uptake in treatment (mg)} - \text{nitrogen uptake in control (g)})}{\text{mass of nitrogen added from urea (mg)}}$$

Nitrogen uptake was measured as described in Example 1. The results are shown in Table 11-1 below.

TABLE 11-1

Biomass productivity and nitrogen use efficiency of canola plants

| Treatment | Biomass productivity (g/mg) | Nitrogen use efficiency (%) |
| --- | --- | --- |
| A | 7.0 | 64 |
| B | 7.4 | 87 |
| C | 8.4 | 76 |
| D | 6.3 | 55 |
| E | 4.6 | 55 |
| G | 7.5 | 64 |
| H | 6.6 | 61 |
| I | 8.4 | 72 |

As seen from the results in Table 11-1, plants treated with the coated fertilizer particles (treatments A, B, C, G, H and I) showed similar or increased biomass productivity and nitrogen use efficiency compared to plants treated with uncoated urea (treatment D) or ESN™ Smart Nitrogen fertilizer (treatment E).

Leaching of Nitrogen from Fertilizer Particles

The total amount of nitrogen (from urea, ammonium ions and nitrate ions) leached from the soil was measured by the colorimetric method of Mulvaney and Bremner (R. L. Mulvaney & J. M. Bremner (1979) "A modified diacetyl monoxime method for colorimetric determination of urea in soil extracts", *Communications in Soil Science and Plant Analysis*, 10:8, 1163-1170). The results are shown in FIG. 11.

As seen from FIG. 11, in the absence of an aptamer which specifically targets a soil exudate, the present coatings (treatments A, B, C, G, H and I) significantly prevent leaching of nitrogen from coated urea fertilizer particles, as compared to nitrogen release from uncoated urea particles (treatment D), and release no more nitrogen into the soil than is released by soil itself, either planted with canola (treatment F) or unplanted (treatment J). In addition, the present coatings show a similar efficacy in preventing leaching of nitrogen from urea fertilizer in soil to that of a commercially available slow release nitrogen fertilizer, ESN™ Smart Nitrogen fertilizer (treatment E). The presence (treatments G, H and I) or absence (treatments A, B and C) of a short random strand of DNA which is not an aptamer for a soil exudate does not show a significant effect on leaching of nitrogen from the coated urea fertilizer particles.

Formation of Root-Ball Mats

Canola plants receiving treatments A (fertilizer particles coated with an embodiment of the present coating containing ethyl cellulose: palmitic acid (1:0.1 by weight)) or C (fertilizer particles coated with palmitic acid) showed formation of root-ball mats, while the control canola plants receiving no nitrogen fertilizer and canola plants receiving uncoated urea fertilizer (treatment D) showed no root-ball mat formation, as seen in FIG. 12. Without being bound by theory, it is contemplated that the coated fertilizer particles enhance the production of root-ball mats around the fertilizer particles, resulting in improved synchronization of release of nitrogen from the fertilizer with uptake of nitrogen by the roots.

Example 12: Preparation and Characterization of Aptamer-Coated Urea Granules

Preparation of Aptamer-Coated Urea Granules

Pellets of commercial urea fertilizer (synAgri) are coated with a coating mixture containing ethyl cellullose (1% by weight), aptamer B-1C (SEQ ID NO:32) and optionally palmitic acid (0.1% or 0.5% by weight) in butanol as described in Example 10.

Aptamer Extractions

Aptamer-coated urea granules were incubated individually in Milli-Q deionized water (500 µL) for 10 minutes to solubilize urea, then centrifuged at 18,000×g for 10 minutes at room temperature. The supernatant, containing the urea fraction, was frozen for subsequent analyses, while the polymer pellet was dissolved in 1-butanol (500 µL). To separate the aptamers from the butanol, an equal volume (500 µL) of Milli-Q water was added, and samples were homogenized using FastPrep-24™ (MP-Biomedicals) at an intensity of 5.5 M/S for 45 seconds. The samples were then incubated 10 minutes at room temperature, then centrifuged at 18,000×g for 10 minutes at room temperature. The organic phase containing the dissolved polymer film in 1-butanol was removed and transferred to a new microcentrifuge tube. The aqueous phase was frozen for subsequent analyses. An equal volume (500 µL) of Milli-Q water was once again added to the organic phase, the mixture was homogenized once more, incubated and centrifuged as described above. The organic phase was discarded while the aqueous phase was frozen at −20° C. for further analyses.

Generating M13-Aptamer Fragments

Aliquots of extracted aptamer sequences were used as templates to generate pJET cloning vector compatible sequences by means of polymerase chain reaction (PCR). Each reaction was performed using the generated templates mixed with a PCR Master Mix consisting of a 2× dilution of the Hotstart™ Taq Plus Master Mix (Invitrogen), and aptamer-M13 forward (5'-CGCCAGGGTTTTCCCAGT-CACGACAGATAGTAAGTGCAATCTAG-3'; SEQ ID NO:35) and reverse (5'-AGCGGATAACAATTT-CACACAGGAGATGCCTAAGTGACTG-3'; SEQ ID NO:36) primers. Reagent quantities and concentrations were added in accordance with the manufacturer's instructions.

All PCR reactions were performed using an Eppendorf nexus GSX1 Mastercycler™, with the following conditions: The initial activation step was performed at 95° C. for 5 minutes, followed by the denaturing step at 94° C. for 30 seconds, annealing at 60° C. for 30 seconds and the extension step at 72° C. for 30 seconds. Each cycle (denaturation, annealing and extension) was repeated 40 times. One final extension step was performed at 72° C. for 10 minutes. An aliquot of the resulting PCR products was run on agarose gels to confirm the expected fragment size of 109 base pairs. All samples were loaded on 1% agarose gels and run at 110 volts for 45 minutes using a Horizon™ 58 (BRL Gibco) gel electrophoresis apparatus connected to a PowerPac™ 300 power supply (Bio-Rad). Once samples were confirmed to be the right size, the remaining PCR products were purified using a DNA Clean & Concentrator™5 kit (Zymo Research), according to the manufacturer's instructions.

Ligation/Transformation of PCR Products

Purified PCR products were ligated into pJET 1.2 cloning vectors using the cloneJET™ cloning kit (Fermentas/Thermo-Fisher), in accordance with the manufacturer's specifications. In summary, a mixture of purified PCR products, reaction buffer, cloning vector and T4 ligase were incubated at 22° C. for 5 minutes in an Eppendorf nexus GSX1 Mastercycler™. The ligation mixture was then used to transform Alpha-Select Gold competent *E. coli* cells (Bioline). 50 µL of the ligation mixture was added to thawed competent cells and incubated on ice for 30 minutes. The tubes were then transferred to a Labnet Accublock™ Digital Dry bath (Mandel) set at 42° C. for 40 seconds, then placed back on ice for 2 minutes. The transformations were then diluted to 1 mL by adding 950 µL of SOC broth (SOC medium: 2% tryptone, 0.5% yeast extract, 0.4% glucose, 10 mM NaCl, 2.5 mM KCl, 10 mM $MgCl_2$ & 10 mM $MgSO_4$), and shaken at 250 rpm for 60 minutes at 37° C. using a Barnstead Max-Q 4000 incubator/shaker. 50 µL or 200 µL of the cell transformation mixture was spread on LB agar plates containing 100 µg/mL of ampicillin and incubated overnight at 37° C. using a Barnstead Imperial III incubator. Positive colonies that had grown overnight were picked for subsequent liquid cultures in 15 mL LB broth supplemented with 100 µg/mL of ampicillin. Liquid cultures were incubated overnight at 37° C. and shaken at 250 rpm in a Barnstead Max-Q 4000 incubator.

Plasmid Extractions/Screening

To confirm successful transformations, plasmids were extracted from the liquid cultures using QIAGEN's QIA-Quick™ plasmid extraction kits, according to the manufacturer's instructions. Plasmid concentrations were assessed using a DeNovix DS-11 FX Spectrophotometer and samples were screened via PCR to confirm the presence of the M13-aptamer fragment, using the PCR and gel electrophoresis conditions described above. Successfully screened samples were subsequently used for sequencing.

Sequencing Reactions

A 1:8 Big dye Terminator master mix, consisting of water, 20% trehalose, 5× sequencing buffer and Big Dye Terminator mix was used in conjunction with either pJET1.2 Forward (5'-CGACTCACTATAGGGAGAGCGGC-3'; SEQ ID NO:37) or pJET1.2 Reverse (5'-AAGAACATCGAT-TTTCCATGGCAG-3'; SEQ ID NO:38) sequencing primers for all sequencing reactions. Samples were incubated in an Eppendorf nexus GSX1 Mastercycler™, using the following conditions: 95° C. for 3 minutes, followed by 40 cycles of 95° C. for 30 seconds, 50° C. for 15 seconds and 60° C. for 2 minutes. Forward and reverse sequencing reads were then aligned against the aptamer sequence (SEQ ID NO:32) using NCBI's megablast (https://blast.ncbi.nlm.nih.gov/Blast.cgi).

Aptamer Quantification

Aptamers loaded onto urea granules were quantified by means of quantitative PCR (qPCR). Aptamers were extracted from aptamer-coated granules as described above, except that the final aqueous phase was run through an analytical evaporator (Organomation N-evap) to remove any remaining 1-butanol that could interfere with qPCR reactions. This was achieved by evaporating the aqueous phase with argon at a flow rate of 2.2 Litres/minute for 15 minutes at a temperature of 50° C.

Aptamer templates were added to a SYBR™ Green qPCR Master Mix consisting of 2×SYBR™ Green Master Mix (Applied Biosciences) and 1 µM of forward (5'-AAGTGCAATCTAGATCGGAAGAG-3'; SEQ ID NO:39) and reverse (5'-GATGCCTAAGTGACTGGAGTTC-3'; SEQ ID NO:40) primers. The standard used to quantify aptamers in extracts consisted of the aptamer sequence (SEQ ID NO:32). The standard used was diluted to a concentration range of $1.28 \times 10^{-6}$ nanomoles/L to $1.64 \times 10^{-11}$ nanomoles/L through 1:5 serial dilutions. The qPCR run conditions consisted of an activation step at 50° C. for 2 minutes, followed by DNA polymerase activation step at 95° C. for 2 minutes. The cycling stages, consisting of the denaturation step at 95° C. for 15 seconds and the annealing/extension steps at 60° C. for one minute, were performed for 40 cycles. All qPCR reactions were done using a StepOnePlus™ Thermocycler (Applied Bioscience). All analyses were performed using StepOnePlus™ software version 2.3. Average values were determined after pooling together aptamer loading values determined for individual urea granules.

Results

Analysis by qPCR indicated that the total average (±standard deviation) amount of extracted aptamer per granule was 107 (±103) pmoles/granule, or 19 ng aptamer per mg aptamer-coated urea.

From these results, two pools of aptamers were identified as being formed during the granule coating and extraction process: a pool that is tightly bound to the polymer film (extractable with 1-butanol) and an aqueous soluble pool obtained when the aptamer-coated granule was placed in water to separate urea from the coating polymer film. On average, 46% of the aptamer was tightly bound to the polymer film and 54% was solubilized in water. For granules coated with ethyl cellulose and the aptamer B-1C only, 84% of the aptamer was bound to the polymer film, while only 16% of the aptamer was bound to the polymer film for granules coated with a mixture of ethyl cellulose, the aptamer B-1C and palmitic acid. Therefore, granules coated with ethyl cellulose and the aptamer B-1C were used in subsequent experiments. The qPCR measurement method used gave reproducible and consistent results of aptamer quantities when extracted granule samples were spiked with a known amount of the aptamer, indicating that variability in aptamer loading is not attributable to the method of extraction and measurement.

Example 13: Urea Release from Aptamer-Coated Urea Granules in Sand

Experimental Protocol

Sand was washed with distilled water, filtered through a 63 µm or 125 µm mesh sieve, dried at 105° C. for several days and autoclaved. The autoclaved sand (80 g) was loaded into a Vivacell™ 70 disposable ultrafiltration unit (Sartorius) and 12.8 mL of Milli-Q (MQ) water was added to reach a field capacity (FC) of 80%. The Vivacell units were then incubated at room temperature overnight. The following day, uncoated urea granules or urea granules coated with a mixture of ethyl cellulose and aptamer B-1C (Example 12) (1 granule (approximately 45-50 mg of urea) per Vivacell unit) were added to the sand at a 2.5 cm depth, then covered. For some experiments with aptamer-coated urea granules, an aqueous solution (25 µL) containing 0.09 nanomoles of L-serine was added to the granule before covering. Samples were incubated for 5 minutes, then 9.95 mL of Milli-Q water was added. Each sample was then centrifuged at 4° C. for 2 minutes at 1000×g. The leachate, located at the bottom of the Vivacell units, was collected and stored at 4° C. for further analyses. Each sand sample was brought back to 80% FC and the incubation/leachate collection steps were repeated after 15 minutes, 30 minutes, 45 minutes, 60 minutes and 120 minutes. Leachates from each sampling time were stored at 4° C. for subsequent analyses.

Colorimetric Assay

The method of Page, A. L., R. H. Miller and D. R. Keeney. 1982. 34-3.1 Diacetyl Monoxime Method (Douglas and Bremner, 1970b) In: Methods of Soil Analysis Part 2—Chemical and Microbiological Properties Second Edition p. 702-703 was modified. Stock solutions of reagents were prepared as follows. 2M KCl solution is prepared by dissolving 150 g of KCl in 1 L of water. Diacetyl monoxime (DAM) solution is prepared by dissolving 2.5 g of DAM in 100 mL of MQ water. Thiosemicarbazide (TSC) solution is prepared by dissolving 0.25 g of TSC in 100 mL of MQ water. Acid reagent solution is prepared by mixing 30 mL of 85% (w/w) orthophosphoric acid and 1 mL of concentrated sulfuric acid, then diluting with water to 50 mL. Colour reagent is prepared immediately before use by adding 2.5 mL of DAM solution and 1 mL TSC solution to 50 mL of acid reagent. Standard urea-N solutions are prepared by dissolving 0.2144 g of pure dry urea in 1 L of 2M KCl solution to make a stock solution containing 100 μg/mL of urea-N. Dilution of this stock solution with 2M KCl solution provides standard urea-N solutions containing concentrations of 0.2 μg/mL, 0.8 μg/mL, 1.4 μg/mL, 2 μg/mL, 2.6 μg/mL, 3.2 μg/mL and 3.8 μg/mL of urea-N, respectively.

A 100 μL aliquot of each sample of leachate solution or standard urea-N solution prepared as described above was added to a 5 mL volumetric flask, then diluted to a total volume of 1 mL with 2M KCl solution. Colour reagent (3 mL) prepared as described above was then added to each sample, and each sample was placed for 27 minutes in a water bath (VWR) set at a temperature of 95° C. Samples were then left to cool under running water for 15 minutes. Samples were then diluted to 5 mL with MQ water and mixed, and the absorbance was measured at 527 nm using a Beckman-Coulter DU-530 UV/Vis spectrophotometer. Urea-N concentrations were determined by comparison with a standard curve obtained from absorbance values measured using standard urea-N solutions.

Statistical Analysis

The experimental design was a two-factor system (i.e., time of incubation and granule coating system) with five replicates. Experimental data was transformed using the Logo function before statistical analysis to conform to a normal distribution. The 2-way analysis of variance (ANOVA) module of XLSTAT was used to test for the effects of time and granule coating system on the release of urea in the sand microcosm. Tukey's test was used to test for significant differences between the effects of various times of incubation and granule coating system on the release of urea.

Statistical analysis of the data showed that the release of urea-N from the uncoated and aptamer-coated urea particles over 120 minutes was significantly influenced by the type of coating system and time of incubation (each at p<0.0001); and also by the interaction between the type of coating system and time of incubation (p=0.003). The type of coating system accounted for 52% of the total variability in the experimental data and time of incubation was responsible for 31% of the total data variability. The interaction between both factors was responsible for 17% of the total data variability.

Results

As seen in FIG. 14, the average rate of release of urea nitrogen from the aptamer-coated granules in the presence of L-serine at 15 minutes after incubation of the granules in the sand was higher than the average rate of release of urea nitrogen from the uncoated particles, which was in turn higher than the average rate of release of urea nitrogen from the aptamer-coated granules in the absence of L-serine. In general, 50% to 60% of the urea was released from the tested granules at a total incubation time between 30 and 40 minutes, and more than 90% of the urea was released from the granules after 60 minutes of incubation.

Table 13-1 below shows kinetic parameters (half-life, rate constant and turnover time) determined for a single pool kinetics, using the approach described in Shipley, R. A. and R. E. Clark. 1972. Tracer methods for in vivo kinetics. Theory and applications. Academic Press, New York, New York 10003, USA., 238 p.

TABLE 13-1

Kinetic parameters of urea nitrogen release from aptamer-coated and uncoated urea granules

| Granule treatment | Average initial amount of urea (mg) | Half-life (s) | Rate constant (k, s$^{-1}$) | Turnover time (1/k, s) |
|---|---|---|---|---|
| Uncoated granules | 26.4 | 34 | 0.020 | 50 |
| Aptamer-coated granules in the absence of L-serine | 20.6 | 45 | 0.015 | 67 |
| Aptamer-coated granules in the presence of L-serine | 19.7 | 30 | 0.023 | 43 |

The measured kinetic parameters further indicate that the rate of release of urea nitrogen was fastest from the aptamer-coated granules in the presence of L-serine and slowest from the aptamer-coated granules in the absence of L-serine. The data indicates that the presence of the coating alone reduces the rate of urea release from the granules compared to uncoated granules. However, in the presence of L-serine, which binds to the aptamer present in the coating, the permeability of the coating is increased, such that the rate of release of urea nitrogen is increased by about 53% over the rate of release from aptamer-coated granules in the absence of L-serine.

The effects of time of incubation and presence or absence of coating and L-serine on the rate of urea nitrogen release in sand were determined by two-way ANOVA. Data measured at 120 minutes did not provide additional information and was omitted. Significant effects on the urea release rate of incubation time (<0.0001) and the presence or absence of coating and L-serine (p=0.019) were seen, using logo transformed data. The interaction between incubation time and the presence or absence of coating and L-serine was not significant (p=0.68).

As seen in FIG. 15, the average rate of urea release was highest after 15 min incubation and decreased in the following order: 15 min>30 min=45 min>60 min, according to Tukey's HSD (Honest Significant Difference) test. The time of incubation accounted for 88% of the total variability of the experimental data and the presence or absence of coating and L-serine accounted for 8% of the total variability of the experimental data. In addition, as seen in FIG. 16, the average rate of urea nitrogen release from aptamer-coated granules in the presence of L-serine (2,002 mg urea-N/kg urea/min) was significantly higher than average rate of urea nitrogen release from aptamer-coated granules in the absence of L-serine (1392 mg urea-N/kg urea/min), but not significantly different from the release rate from uncoated granules (1,930 mg urea-N/kg urea/min).

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples but should be given the broadest interpretation consistent with the description as a whole.

The invention claimed is:

1. A delivery system for delivering an agrochemical to a root of a plant, the system comprising particles configured to release the agrochemical, the particles comprising a coating, wherein the coating comprises an aptamer configured to bind specifically to a root exudate, wherein the root exudate comprises L-serine,
and wherein exposure of the particles to the root exudate results in an increase in permeability of the coating, so as to increase a rate of release of the agrochemical from the particles.

2. The delivery system of claim 1 wherein the particles are particles of a fertilizer configured to release one or more nutrients to the root of the plant,
wherein exposure of the particles to the root exudate results in an increase in permeability of the coating, so as to increase a rate of release of the one or more nutrients from the particles.

3. The delivery system of claim 2 wherein the one or more nutrients comprise nitrogen.

4. The delivery system of claim 3, wherein the fertilizer is urea.

5. The delivery system of claim 2 wherein the aptamer has a sequence selected from the group consisting of SEQ ID NO:20, SEQ ID NO:21, SEQ ID NO:22, SEQ ID NO:23, SEQ ID NO:24, SEQ ID NO:25, SEQ ID NO:30, SEQ ID NO:31, SEQ ID NO:32, SEQ ID NO:33 and SEQ ID NO:34.

6. The delivery system of claim 2 wherein the plant is a canola plant.

7. The delivery system of claim 1 wherein the coating comprises a cellulose derivative.

8. The delivery system of claim 7 wherein the coating additionally comprises a fatty acid.

9. The delivery system of claim 8 wherein the fatty acid is palmitic acid.

10. The delivery system of claim 7 wherein the cellulose derivative is ethyl cellulose.

11. A method of preparing the delivery system of claim 1, the method comprising coating the particles with the coating.

12. An aptamer configured to bind specifically to a root exudate, wherein the root exudate comprises L-serine and wherein the aptamer has a sequence selected from the group consisting of SEQ ID NO:20, SEQ ID NO:21, SEQ ID NO:22, SEQ ID NO:23, SEQ ID NO:24, SEQ ID NO:25, SEQ ID NO:30, SEQ ID NO:31, SEQ ID NO:32, SEQ ID NO:33 and SEQ ID NO:34.

13. A coating for particles of an agrochemical, the coating comprising a cellulose derivative and an aptamer configured to bind specifically to a root exudate, wherein the root exudate comprises L-serine.

14. The coating of cla

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Library A 5' sequence

<400> SEQUENCE: 1
agcagcacag aggtcagatg                                                    20

<210> SEQ ID NO 2
<211> LENGTH: 20
<212> TYPE: DNA
<213> ORGANISM: Artificial Sequence
<220> FEATURE:
<223> OTHER INFORMATION: Library A 3' sequence

<400> SEQUENCE: 2
cctatgcgtg ctaccgtgaa                                                    20

<210> SEQ ID NO 3
<211> LENGTH: 20
<212> TYPE: DNA
<213> ORGANISM: Artificial Sequence
<220> FEATURE:
<223> OTHER INFORMATION: Library A forward primer

<400> SEQUENCE: 3
agcagcacag aggtcagatg                                                    20

<210> SEQ ID NO 4
<211> LENGTH: 20
<212> TYPE: DNA
<213> ORGANISM: Artificial Sequence
<220> FEATURE:
<223> OTHER INFORMATION: Library A reverse primer

<400> SEQUENCE: 4
ttcacggtag cacgcatagg                                                    20

<210> SEQ ID NO 5
<211> LENGTH: 97
<212> TYPE: DNA
<213> ORGANISM: Artificial Sequence
<220> FEATURE:
<223> OTHER INFORMATION: Library C starting nucleotide

<400> SEQUENCE: 5
ataccagctt attcaattgt ggaaagccga atgtgattag ggaccagtgg agaagtagta        60
cggactgacc tcgcgtgtaa gatagtaagt gcaatct                                 97

<210> SEQ ID NO 6
<211> LENGTH: 18
<212> TYPE: DNA
<213> ORGANISM: Artificial Sequence
<220> FEATURE:
<223> OTHER INFORMATION: Library C 5' forward primer

<400> SEQUENCE: 6
ataccagctt attcaatt                                                      18

<210> SEQ ID NO 7
<211> LENGTH: 18
```

```
<212> TYPE: DNA
<213> ORGANISM: Artificial Sequence
<220> FEATURE:
<223> OTHER INFORMATION: Library C 3' reverse primer

<400> SEQUENCE: 7
agattgcact tactatct                                                      18

<210> SEQ ID NO 8
<211> LENGTH: 76
<212> TYPE: DNA
<213> ORGANISM: Artificial Sequence
<220> FEATURE:
<223> OTHER INFORMATION: Adapter F1

<400> SEQUENCE: 8
aatgatacgg cgaccaccga gatctacact ctttccctac acgacgctct tccgatctat        60
accagcttat tcaatt                                                        76

<210> SEQ ID NO 9
<211> LENGTH: 77
<212> TYPE: DNA
<213> ORGANISM: Artificial Sequence
<220> FEATURE:
<223> OTHER INFORMATION: Adapter F2
<220> FEATURE:
<221> NAME/KEY: misc_feature
<222> LOCATION: (59)..(59)
<223> OTHER INFORMATION: A, C, T or G

<400> SEQUENCE: 9
aatgatacgg cgaccaccga gatctacact ctttccctac acgacgctct tccgatctna        60
taccagctta ttcaatt                                                       77

<210> SEQ ID NO 10
<211> LENGTH: 80
<212> TYPE: DNA
<213> ORGANISM: Artificial Sequence
<220> FEATURE:
<223> OTHER INFORMATION: Adapter F3
<220> FEATURE:
<221> NAME/KEY: misc_feature
<222> LOCATION: (59)..(59)
<223> OTHER INFORMATION: A, C, T or G
<220> FEATURE:
<221> NAME/KEY: misc_feature
<222> LOCATION: (60)..(60)
<223> OTHER INFORMATION: A, C, T or G

<400> SEQUENCE: 10
aatgatacgg cgaccaccga gatctacact ctttccctac acgacgctct tccgatctnn        60
agcagcacag aggtcagatg                                                    80

<210> SEQ ID NO 11
<211> LENGTH: 81
<212> TYPE: DNA
<213> ORGANISM: Artificial Sequence
<220> FEATURE:
<223> OTHER INFORMATION: Adapter F4
<220> FEATURE:
<221> NAME/KEY: misc_feature
<222> LOCATION: (59)..(59)
<223> OTHER INFORMATION: A, C, T or G
<220> FEATURE:
<221> NAME/KEY: misc_feature
<222> LOCATION: (60)..(60)
<223> OTHER INFORMATION: A, C, T or G
<220> FEATURE:
```

```
<221> NAME/KEY: misc_feature
<222> LOCATION: (61)..(61)
<223> OTHER INFORMATION: A, C, T or G

<400> SEQUENCE: 11
aatgatacgg cgaccaccga gatctacact ctttccctac acgacgctct tccgatctnn    60
nagcagcaca gaggtcagat g                                              81

<210> SEQ ID NO 12
<211> LENGTH: 81
<212> TYPE: DNA
<213> ORGANISM: Artificial Sequence
<220> FEATURE:
<223> OTHER INFORMATION: Adapter R1

<400> SEQUENCE: 12
caagcagaag acggcatacg agatcgtgat gtgactggag ttcagacgtg tgctcttccg    60
atcagattgc acttactatc t                                              81

<210> SEQ ID NO 13
<211> LENGTH: 81
<212> TYPE: DNA
<213> ORGANISM: Artificial Sequence
<220> FEATURE:
<223> OTHER INFORMATION: Adapter R2

<400> SEQUENCE: 13
caagcagaag acggcatacg agatacatcg gtgactggag ttcagacgtg tgctcttccg    60
atcagattgc acttactatc t                                              81

<210> SEQ ID NO 14
<211> LENGTH: 82
<212> TYPE: DNA
<213> ORGANISM: Artificial Sequence
<220> FEATURE:
<223> OTHER INFORMATION: Adapter R3
<220> FEATURE:
<221> NAME/KEY: misc_feature
<222> LOCATION: (64)..(64)
<223> OTHER INFORMATION: A, C, T or G

<400> SEQUENCE: 14
caagcagaag acggcatacg agatgcctaa gtgactggag ttcagacgtg tgctcttccg    60
atcnagattg cacttactat ct                                             82

<210> SEQ ID NO 15
<211> LENGTH: 82
<212> TYPE: DNA
<213> ORGANISM: Artificial Sequence
<220> FEATURE:
<223> OTHER INFORMATION: Adapter R4
<220> FEATURE:
<221> NAME/KEY: misc_feature
<222> LOCATION: (64)..(64)
<223> OTHER INFORMATION: A, C, T or G

<400> SEQUENCE: 15
caagcagaag acggcatacg agattggtca gtgactggag ttcagacgtg tgctcttccg    60
atcnagattg cacttactat ct                                             82

<210> SEQ ID NO 16
<211> LENGTH: 85
<212> TYPE: DNA
<213> ORGANISM: Artificial Sequence
```

```
<220> FEATURE:
<223> OTHER INFORMATION: Adapter R5
<220> FEATURE:
<221> NAME/KEY: misc_feature
<222> LOCATION: (64)..(64)
<223> OTHER INFORMATION: A, C, T or G
<220> FEATURE:
<221> NAME/KEY: misc_feature
<222> LOCATION: (65)..(65)
<223> OTHER INFORMATION: A, C, T or G

<400> SEQUENCE: 16
caagcagaag acggcatacg agatcactgt gtgactggag ttcagacgtg tgctcttccg      60
atcnnttcac ggtagcacgc atagg                                            85

<210> SEQ ID NO 17
<211> LENGTH: 85
<212> TYPE: DNA
<213> ORGANISM: Artificial Sequence
<220> FEATURE:
<223> OTHER INFORMATION: Adapter R6
<220> FEATURE:
<221> NAME/KEY: misc_feature
<222> LOCATION: (64)..(64)
<223> OTHER INFORMATION: A, C, T or G
<220> FEATURE:
<221> NAME/KEY: misc_feature
<222> LOCATION: (65)..(65)
<223> OTHER INFORMATION: A, C, T or G

<400> SEQUENCE: 17
caagcagaag acggcatacg agatattggc gtgactggag ttcagacgtg tgctcttccg      60
atcnnttcac ggtagcacgc atagg                                            85

<210> SEQ ID NO 18
<211> LENGTH: 86
<212> TYPE: DNA
<213> ORGANISM: Artificial Sequence
<220> FEATURE:
<223> OTHER INFORMATION: Adapter R7
<220> FEATURE:
<221> NAME/KEY: misc_feature
<222> LOCATION: (64)..(64)
<223> OTHER INFORMATION: A, C, T or G
<220> FEATURE:
<221> NAME/KEY: misc_feature
<222> LOCATION: (65)..(65)
<223> OTHER INFORMATION: A, C, T or G
<220> FEATURE:
<221> NAME/KEY: misc_feature
<222> LOCATION: (66)..(66)
<223> OTHER INFORMATION: A, C, T or G

<400> SEQUENCE: 18
caagcagaag acggcatacg agatgatctg gtgactggag ttcagacgtg tgctcttccg      60
atcnnnttca cggtagcacg catagg                                           86

<210> SEQ ID NO 19
<211> LENGTH: 86
<212> TYPE: DNA
<213> ORGANISM: Artificial Sequence
<220> FEATURE:
<223> OTHER INFORMATION: Adapter R8
<220> FEATURE:
<221> NAME/KEY: misc_feature
<222> LOCATION: (64)..(64)
<223> OTHER INFORMATION: A, C, T or G
<220> FEATURE:
<221> NAME/KEY: misc_feature
<222> LOCATION: (65)..(65)
```

```
<223> OTHER INFORMATION: A, C, T or G
<220> FEATURE:
<221> NAME/KEY: misc_feature
<222> LOCATION: (66)..(66)
<223> OTHER INFORMATION: A, C, T or G

<400> SEQUENCE: 19
caagcagaag acggcatacg agattcaagt gtgactggag ttcagacgtg tgctcttccg    60
atcnnnttca cggtagcacg catagg                                        86

<210> SEQ ID NO 20
<211> LENGTH: 80
<212> TYPE: DNA
<213> ORGANISM: Artificial Sequence
<220> FEATURE:
<223> OTHER INFORMATION: Aptamer A-1

<400> SEQUENCE: 20
agcagcacag aggtcagatg cctatgcgtg ctaccgtgaa accgatcgga agagcacacg    60
cctatgcgtg ctaccgtgaa                                               80

<210> SEQ ID NO 21
<211> LENGTH: 80
<212> TYPE: DNA
<213> ORGANISM: Artificial Sequence
<220> FEATURE:
<223> OTHER INFORMATION: Aptamer A-2

<400> SEQUENCE: 21
agcagcacag aggtcagatg cgatctggat attattttg atacccctttt ggggagacat    60 cctatgcgtg ctaccgtgaa                                               80

<210> SEQ ID NO 22
<211> LENGTH: 97
<212> TYPE: DNA
<213> ORGANISM: Artificial Sequence
<220> FEATURE:
<223> OTHER INFORMATION: Aptamer B-1

<400> SEQUENCE: 22
ataccagctt attcaattag atagtaagtg caatctagat cggaagagca cacgtctgaa    60
ctccagtcac ttaggcatca gatagtaagt gcaatct                            97

<210> SEQ ID NO 23
<211> LENGTH: 97
<212> TYPE: DNA
<213> ORGANISM: Artificial Sequence
<220> FEATURE:
<223> OTHER INFORMATION: Aptamer B-2

<400> SEQUENCE: 23
ataccagctt attcaattgg ccgtgtagat agtaagtgca atctgatcgg aagagcacac    60
gtctgaactc cagtcaccga gatagtaagt gcaatct                            97

<210> SEQ ID NO 24
<211> LENGTH: 97
<212> TYPE: DNA
<213> ORGANISM: Artificial Sequence
<220> FEATURE:
<223> OTHER INFORMATION: Aptamer C-1

<400> SEQUENCE: 24
ataccagctt attcaattag atagtaagtg caatcttgat cggaagagca cacgtctgaa    60
```
ctccagtcac ttaggcatca gatagtaagt gcaatct                                    97

<210> SEQ ID NO 25
<211> LENGTH: 97
<212> TYPE: DNA
<213> ORGANISM: Artificial Sequence
<220> FEATURE:
<223> OTHER INFORMATION: Aptamer C-2

<400> SEQUENCE: 25
ataccagctt attcaattgt atacggagtg gatatcgatc tgtaacgtga gtgagataat          60
gtgatgcata gtcgtggaga gatagtaagt gcaatct                                    97

<210> SEQ ID NO 26
<211> LENGTH: 18
<212> TYPE: DNA
<213> ORGANISM: Artificial Sequence
<220> FEATURE:
<223> OTHER INFORMATION: Common sequence motif

<400> SEQUENCE: 26
agatagtaag tgcaatct                                                         18

<210> SEQ ID NO 27
<211> LENGTH: 38
<212> TYPE: DNA
<213> ORGANISM: Artificial Sequence
<220> FEATURE:
<223> OTHER INFORMATION: common sequence motif

<400> SEQUENCE: 27
ggaagagcac acgtctgaac tccagtcact taggcatc                                   38

<210> SEQ ID NO 28
<211> LENGTH: 13
<212> TYPE: DNA
<213> ORGANISM: Artificial Sequence
<220> FEATURE:
<223> OTHER INFORMATION: common sequence motif

<400> SEQUENCE: 28
ggaagagcac acg                                                              13

<210> SEQ ID NO 29
<211> LENGTH: 18
<212> TYPE: DNA
<213> ORGANISM: Artificial Sequence
<220> FEATURE:
<223> OTHER INFORMATION: Forward primer binding site libraries B and C

<400> SEQUENCE: 29
ataccagctt attcaatt                                                         18

<210> SEQ ID NO 30
<211> LENGTH: 47
<212> TYPE: DNA
<213> ORGANISM: Artificial Sequence
<220> FEATURE:
<223> OTHER INFORMATION: Aptamer B-1A

<400> SEQUENCE: 30
ataccagctt attcaattag atagtaagtg caatctagat cggaaga                         47

<210> SEQ ID NO 31

```
<211> LENGTH: 50
<212> TYPE: DNA
<213> ORGANISM: Artificial Sequence
<220> FEATURE:
<223> OTHER INFORMATION: Aptamer B-1B

<400> SEQUENCE: 31
gcacacgtct gaactccagt cacttaggca tcagatagta agtgcaatct            50

<210> SEQ ID NO 32
<211> LENGTH: 61
<212> TYPE: DNA
<213> ORGANISM: Artificial Sequence
<220> FEATURE:
<223> OTHER INFORMATION: Aptamer B-1C

<400> SEQUENCE: 32
agatagtaag tgcaatctag atcggaagag cacacgtctg aactccagtc acttaggcat  60
c                                                                 61

<210> SEQ ID NO 33
<211> LENGTH: 79
<212> TYPE: DNA
<213> ORGANISM: Artificial Sequence
<220> FEATURE:
<223> OTHER INFORMATION: Aptamer B-1D

<400> SEQUENCE: 33
ataccagctt attcaattag atagtaagtg caatctagat cggaagagca cacgtctgaa  60
ctccagtcac ttaggcatc                                              79

<210> SEQ ID NO 34
<211> LENGTH: 61
<212> TYPE: DNA
<213> ORGANISM: Artificial Sequence
<220> FEATURE:
<223> OTHER INFORMATION: Aptamer B-1CL
<220> FEATURE:
<221> NAME/KEY: misc_feature
<222> LOCATION: (1)..(61)
<223> OTHER INFORMATION: L-deoxyribose

<400> SEQUENCE: 34
agatagtaag tgcaatctag atcggaagag cacacgtctg aactccagtc acttaggcat  60
c                                                                 61

<210> SEQ ID NO 35
<211> LENGTH: 44
<212> TYPE: DNA
<213> ORGANISM: Artificial Sequence
<220> FEATURE:
<223> OTHER INFORMATION: Forward primer

<400> SEQUENCE: 35
cgccagggtt ttcccagtca cgacagatag taagtgcaat ctag                  44

<210> SEQ ID NO 36
<211> LENGTH: 40
<212> TYPE: DNA
<213> ORGANISM: Artificial Sequence
<220> FEATURE:
<223> OTHER INFORMATION: Reverse primer

<400> SEQUENCE: 36
agcggataac aatttcacac aggagatgcc taagtgactg                       40
```

```
<210> SEQ ID NO 37
<211> LENGTH: 23
<212> TYPE: DNA
<213> ORGANISM: Artificial Sequence
<220> FEATURE:
<223> OTHER INFORMATION: Forward primer

<400> SEQUENCE: 37
cgactcacta tagggagagc ggc                                           23

<210> SEQ ID NO 38
<211> LENGTH: 24
<212> TYPE: DNA
<213> ORGANISM: Artificial Sequence
<220> FEATURE:
<223> OTHER INFORMATION: Reverse primer

<400> SEQUENCE: 38
aagaacatcg attttccatg gcag                                          24

<210> SEQ ID NO 39
<211> LENGTH: 23
<212> TYPE: DNA
<213> ORGANISM: Artificial Sequence
<220> FEATURE:
<223> OTHER INFORMATION: Forward primer

<400> SEQUENCE: 39
aagtgcaatc tagatcggaa gag                                           23

<210> SEQ ID NO 40
<211> LENGTH: 22
<212> TYPE: DNA
<213> ORGANISM: Artificial Sequence
<220> FEATURE:
<223> OTHER INFORMATION: Reverse primer

<400> SEQUENCE: 40
gatgcctaag tgactggagt tc                                            22
```